United States Patent
Hsu et al.

(10) Patent No.: US 12,187,687 B2
(45) Date of Patent: Jan. 7, 2025

(54) COMPOSITIONS AND USES THEREOF

(71) Applicant: University of Virginia Patent Foundation, Charlottesville, VA (US)

(72) Inventors: Ku-Lung Hsu, Charlottesville, VA (US); Caroline Elise Franks, Charlottesville, VA (US); Heung Sik Hahm, Charlottesville, VA (US); Jeffrey W. Brulet, Glen Allen, VA (US); Tao Huang, Charlottesville, VA (US)

(73) Assignee: University of Virginia Patent Foundation, Charlottesville, VA (US)

( * ) Notice: Subject to any disclaimer, the term of this patent is extended or adjusted under 35 U.S.C. 154(b) by 0 days.

(21) Appl. No.: 16/621,585

(22) PCT Filed: Jun. 26, 2018

(86) PCT No.: PCT/US2018/039615
§ 371 (c)(1),
(2) Date: Dec. 11, 2019

(87) PCT Pub. No.: WO2019/005883
PCT Pub. Date: Jan. 3, 2019

(65) Prior Publication Data
US 2020/0231551 A1    Jul. 23, 2020

Related U.S. Application Data

(60) Provisional application No. 62/524,738, filed on Jun. 26, 2017.

(51) Int. Cl.
| | |
|---|---|
| C07D 241/04 | (2006.01) |
| A61P 35/00 | (2006.01) |
| C07D 211/18 | (2006.01) |
| C07D 401/06 | (2006.01) |
| C07D 401/14 | (2006.01) |
| C07D 403/06 | (2006.01) |
| C07D 471/08 | (2006.01) |
| C07D 513/04 | (2006.01) |

(52) U.S. Cl.
CPC ............ *C07D 241/04* (2013.01); *A61P 35/00* (2018.01); *C07D 401/06* (2013.01); *C07D 403/06* (2013.01); *C07D 471/08* (2013.01); *C07D 513/04* (2013.01)

(58) Field of Classification Search
CPC .. C07D 211/18; C07D 403/06; C07D 471/08; C07D 401/06; C07D 401/14; C07D 241/04; C07D 513/04; A61P 35/00
See application file for complete search history.

(56) References Cited

U.S. PATENT DOCUMENTS 4,853,387 A    8/1989 Manoury et al.

FOREIGN PATENT DOCUMENTS

| WO | WO-9206970 A1 | 4/1992 |
|---|---|---|
| WO | WO-2015080949 A1 | 6/2015 |
| WO | WO-2019005883 A1 | 1/2019 |

OTHER PUBLICATIONS

RN2061979-72-2, registry database compound, 2017.*
RN93076-09-6, registry database compound, entry date 1984.*
RN4878-88-0, registry database compound, entry date 1984.*
"International Application Serial No. PCT/US2018/039615, International Search Report mailed Oct. 18, 2018", 8 pgs.
"International Application Serial No. PCT/US2018/039615, Written Opinion mailed Oct. 18, 2018", 8 pgs.
Boroda, Salome, et al., "Dual activities of ritanserin and R59022 as DGK DGK inhibitors and serotonin receptor Antagonists", Biochemical Pharmacology Elsevier US vol. 123, (Oct. 28, 2016), 11 pgs.
Claudi, et al., "Simplified analogues of ritanserin and their affinity at 5-HT2A 5-HT2B and 5-HT2C serotonin receptors", 9 pgs.
Ekwall, Bjorn, et al., "Preliminary studies on the validity of in vitro measurement of drug toxicity using Hela cells II Drug toxicity in the MIT-24 system compared with mouse and human lethal dosage of 52 drugs", Toxicology Letters Elsevier Biomedical Press, Amsterdam, NL, vol. 5 No. 5, (Apr. 1, 1980), 9 pgs.
Matthew, D Hall, et al., "Fluorescence polarization assays in high-throughput screening and drug discovery a review", Methods and Applications in Fluorescence vol. 4 No. 2, (Apr. 28, 2016), 21 pgs.
Narendra, Sharath Chandra, et al., "Synthesis and in vitro antimicrobial studies of medicinally important novelN-alkyl andN-sulfonyl derivatives of 1-s4-fluorophenyl-methylpiperazjne", Bioorganic Medicinal Chemistry vol. 14 No. 19, (Oct. 1, 2006), 7 pgs.
Ruth, Regan, et al., "Effects of the Antiestrogens Tamoxifen Toremifene and ICI 182780 on Endometrial Cancer Growth", Journal of the National Cancer Institute vol. 90 No. 20, (Oct. 21, 1998), 7 pgs.
Shanklin, J R, et al., "Synthesis Calcium-Channel-Blocking Activity And Antihypertensive Activity Of 4-Diarylmethyl-1-3-Aryloxy Propyl Pipe Ridines And Structurally Related Compounds", Journal of Medicinal Chemistry American Chemical Society, vol. 34 No. 10, (Jan. 1, 1991), 12 pgs.
Tsuneji, Suzuki, et al., "Structure-Activity Relationship of Newly Synthesized Quinoline Derivatives for Reversal of Multidrug Resistance in Cancer1", Journal of Medicinal Chemistry American Chemical Society, vol. 40 No. 13, (Jan. 1, 1997), 6 pgs.
"International Application Serial No. PCT/US2018/039615, International Preliminary Report on Patentability mailed Jan. 9, 2020", 10 pgs.

* cited by examiner

*Primary Examiner* — Sun Jae Yoo
(74) *Attorney, Agent, or Firm* — Schwegman Lundberg & Woessner, P.A.

(57) ABSTRACT

The disclosure is directed to compounds of the formula (1A), (I)—(V) and others disclosed herein and uses of such compounds.

3 Claims, 17 Drawing Sheets

Specification includes a Sequence Listing.

DAGKc subdomain

DAGKa subdomain

FIG. 13

SEQUENCE LISTING

```
<160> NUMBER OF SEQ ID NOS: 83

<210> SEQ ID NO 1
<211> LENGTH: 4
<212> TYPE: PRT
<213> ORGANISM: Artificial Sequence
<220> FEATURE:
<223> OTHER INFORMATION: A synthetic amino acid sequence

<400> SEQUENCE: 1

Glu Pro Ala Pro
1

<210> SEQ ID NO 2
<211> LENGTH: 21
<212> TYPE: PRT
<213> ORGANISM: Homo sapiens

<400> SEQUENCE: 2

Ile Glu Pro Val Ser Asn Thr His Pro Leu Leu Val Phe Ile Asn Pro
1               5                   10                  15

Lys Ser Gly Gly Lys
            20

<210> SEQ ID NO 3
<211> LENGTH: 8
<212> TYPE: PRT
<213> ORGANISM: Homo sapiens
```

```
<400> SEQUENCE: 3

Tyr Pro Glu Lys Phe Asn Ser Arg
1               5

<210> SEQ ID NO 4
<211> LENGTH: 19
<212> TYPE: PRT
<213> ORGANISM: Homo sapiens

<400> SEQUENCE: 4

Gln Gly Leu Ser Cys Asn Leu Cys Lys Tyr Ile Val His Asp His Cys
1               5                   10                  15

Ala Met Lys

<210> SEQ ID NO 5
<211> LENGTH: 13
<212> TYPE: PRT
<213> ORGANISM: S. aureus

<400> SEQUENCE: 5

Ala Arg Ile Ile Tyr Asn Pro Thr Ser Gly Lys Glu Gln
1               5                   10

<210> SEQ ID NO 6
<211> LENGTH: 13
<212> TYPE: PRT
<213> ORGANISM: Rattus norvegicus

<400> SEQUENCE: 6

Leu Leu Val Phe Ile Asn Pro Lys Ser Gly Gly Lys Gln
1               5                   10

<210> SEQ ID NO 7
<211> LENGTH: 58
<212> TYPE: PRT
<213> ORGANISM: Homo sapiens

<400> SEQUENCE: 7

Thr Thr Asp Val Thr Ser Leu Cys Thr Pro Glu Ala Phe Arg Ile Glu
1               5                   10                  15

Pro Val Ser Asn Thr His Pro Leu Leu Val Phe Ile Asn Pro Lys Ser
                20                  25                  30

Gly Gly Lys Gln Gly Gln Ser Val Leu Trp Lys Phe Gln Tyr Ile Leu
                35                  40                  45

Asn Pro Arg Gln Val Phe Asn Leu Lys Asp
                50                  55

<210> SEQ ID NO 8
<211> LENGTH: 47
<212> TYPE: PRT
<213> ORGANISM: Homo sapiens

<400> SEQUENCE: 8

Asn Leu Asp Trp Ser Ser Ala Cys Ser Cys Pro Leu Leu Ile Phe Ile
1               5                   10                  15

Asn Ser Lys Ser Gly Asp His Gln Gly Ile Val Phe Leu Arg Lys Phe
                20                  25                  30

Lys Gln Tyr Leu Asn Pro Ser Gln Val Phe Asp Leu Leu Lys Gly
                35                  40                  45

<210> SEQ ID NO 9
```

```
<211> LENGTH: 55
<212> TYPE: PRT
<213> ORGANISM: Homo sapiens

<400> SEQUENCE: 9

Asp Lys Lys Thr Asp Tyr Glu Val Leu Ala Ser Lys Leu Gly Lys Gln
1               5                   10                  15

Trp Thr Pro Leu Ile Ile Leu Ala Asn Ser Arg Ser Gly Thr Asn Met
            20                  25                  30

Gly Glu Gly Leu Leu Gly Glu Phe Arg Ile Leu Leu Asn Pro Val Gln
        35                  40                  45

Val Phe Asp Val Thr Lys Thr
    50                  55

<210> SEQ ID NO 10
<211> LENGTH: 59
<212> TYPE: PRT
<213> ORGANISM: Homo sapiens

<400> SEQUENCE: 10

Lys Gly Pro Glu Glu Gly Arg Trp Arg Pro Phe Ile Ile Arg Pro Thr
1               5                   10                  15

Pro Ser Pro Leu Met Lys Pro Leu Leu Val Phe Val Asn Pro Lys Ser
            20                  25                  30

Gly Gly Asn Gln Gly Ala Lys Ile Ile Gln Ser Phe Leu Trp Tyr Leu
        35                  40                  45

Asn Pro Arg Gln Val Phe Asp Leu Ser Gln Gly
    50                  55

<210> SEQ ID NO 11
<211> LENGTH: 60
<212> TYPE: PRT
<213> ORGANISM: Homo sapiens

<400> SEQUENCE: 11

Arg Gly Arg Leu Leu Thr Ala Leu Val Leu Pro Asp Leu Leu His Ala
1               5                   10                  15

Lys Leu Pro Pro Asp Ser Cys Pro Leu Leu Val Phe Val Asn Pro Lys
            20                  25                  30

Ser Gly Gly Leu Lys Gly Arg Asp Leu Leu Cys Ser Phe Arg Lys Leu
        35                  40                  45

Leu Asn Pro His Gln Val Phe Asp Leu Thr Asn Gly
    50                  55                  60

<210> SEQ ID NO 12
<211> LENGTH: 93
<212> TYPE: PRT
<213> ORGANISM: Homo sapiens

<400> SEQUENCE: 12

Glu Lys Ser Asp Pro Val Pro Ser Gln Ile Ile Asn Asn Tyr Phe Ser
1               5                   10                  15

Ile Gly Val Asp Ala Ser Ile Ala His Arg Phe His Leu Met Arg Glu
            20                  25                  30

Lys Tyr Pro Glu Lys Phe Asn Ser Arg Met Lys Asn Lys Leu Trp Tyr
        35                  40                  45

Leu Glu Phe Ala Thr Ser Glu Ser Ile Phe Ser Ser Thr Cys Lys Lys
    50                  55                  60

Leu Glu Glu Ser Val Thr Val Glu Ile Cys Gly Lys Leu Leu Asp Leu
```

```
                65                  70                  75                  80
Ser Asp Leu Ser Leu Glu Gly Ile Ala Val Leu Asn Ile
                    85                  90

<210> SEQ ID NO 13
<211> LENGTH: 116
<212> TYPE: PRT
<213> ORGANISM: Homo sapiens

<400> SEQUENCE: 13

Gly Thr Leu Ser Ser Ile Ser Ser Leu Lys Ser Glu Asp Leu Asp Asn
1               5                   10                  15

Leu Asn Leu Asp His Leu His Phe Thr Pro Glu Ser Ile Arg Phe Lys
                20                  25                  30

Glu Lys Cys Val Met Asn Asn Tyr Phe Gly Ile Gly Leu Asp Ala Lys
            35                  40                  45

Ile Ser Leu Asp Phe Asn Thr Arg Arg Asp Glu His Pro Gly Gln Tyr
        50                  55                  60

Asn Ser Arg Leu Lys Asn Lys Met Trp Tyr Gly Leu Leu Gly Thr Lys
65                  70                  75                  80

Glu Leu Leu Gln Arg Ser Tyr Arg Lys Leu Glu Glu Arg Val His Leu
                85                  90                  95

Glu Cys Asp Gly Glu Thr Ile Ser Leu Pro Asn Leu Gln Gly Ile Val
            100                 105                 110

Val Leu Asn Ile
        115

<210> SEQ ID NO 14
<211> LENGTH: 90
<212> TYPE: PRT
<213> ORGANISM: Homo sapiens

<400> SEQUENCE: 14

Tyr Asn Leu Arg Lys Pro Lys Glu Phe Thr Met Asn Asn Tyr Phe Ser
1               5                   10                  15

Val Gly Pro Asp Ala Leu Met Ala Leu Asn Phe His Ala His Arg Glu
                20                  25                  30

Lys Ala Pro Ser Leu Phe Ser Ser Arg Ile Leu Asn Lys Ala Val Tyr
            35                  40                  45

Leu Phe Tyr Gly Thr Lys Asp Cys Leu Val Gln Glu Cys Lys Asp Leu
        50                  55                  60

Asn Lys Lys Val Glu Leu Glu Leu Asp Gly Glu Arg Val Ala Leu Pro
65                  70                  75                  80

Ser Leu Glu Gly Ile Ile Val Leu Asn Ile
                85                  90

<210> SEQ ID NO 15
<211> LENGTH: 94
<212> TYPE: PRT
<213> ORGANISM: Homo sapiens

<400> SEQUENCE: 15

Gly Ala Thr Asp Arg Leu Pro Leu Asp Val Phe Asn Asn Tyr Phe Ser
1               5                   10                  15

Leu Gly Phe Asp Ala His Val Thr Leu Glu Phe His Glu Ser Arg Glu
                20                  25                  30

Ala Asn Pro Glu Lys Phe Asn Ser Arg Phe Arg Asn Lys Met Phe Tyr
            35                  40                  45
```

```
Ala Gly Thr Ala Phe Ser Asp Phe Leu Met Gly Ser Ser Lys Asp Leu
 50                  55                  60

Ala Lys His Ile Arg Val Val Cys Asp Gly Met Asp Leu Thr Pro Lys
 65                  70                  75                  80

Ile Gln Asp Leu Lys Pro Gln Cys Val Val Phe Leu Asn Ile
                 85                  90
```

```
<210> SEQ ID NO 16
<211> LENGTH: 88
<212> TYPE: PRT
<213> ORGANISM: Homo sapiens

<400> SEQUENCE: 16

Ala Asp Ala Glu Pro Pro Lys Ile Val Gln Met Ser Asn Tyr Cys Gly
 1               5                  10                  15

Ile Gly Ile Asp Ala Glu Leu Ser Leu Asp Phe His Gln Ala Arg Glu
                 20                  25                  30

Glu Glu Pro Gly Lys Phe Thr Ser Arg Leu His Asn Lys Gly Val Tyr
             35                  40                  45

Val Arg Val Gly Leu Gln Lys Ile Ser His Ser Arg Ser Leu His Lys
 50                  55                  60

Gln Ile Arg Leu Gln Val Glu Arg Gln Glu Val Glu Leu Pro Ser Ile
 65                  70                  75                  80

Glu Gly Leu Ile Phe Ile Asn Ile
                 85
```

```
<210> SEQ ID NO 17
<211> LENGTH: 19
<212> TYPE: PRT
<213> ORGANISM: Rattus norvegicus

<400> SEQUENCE: 17

Gln Gly Leu Ser Cys Asn Leu Cys Lys Tyr Ile Val His Asp His Cys
 1               5                  10                  15

Ala Met Lys
```

```
<210> SEQ ID NO 18
<211> LENGTH: 21
<212> TYPE: PRT
<213> ORGANISM: Rattus norvegicus

<400> SEQUENCE: 18

Ile Glu Pro Val Ser Asn Thr His Pro Leu Leu Val Phe Ile Asn Pro
 1               5                  10                  15

Lys Ser Gly Gly Lys
                 20
```

```
<210> SEQ ID NO 19
<211> LENGTH: 8
<212> TYPE: PRT
<213> ORGANISM: Rattus norvegicus

<400> SEQUENCE: 19

Tyr Pro Glu Lys Phe Asn Ser Arg
 1               5
```

```
<210> SEQ ID NO 20
<211> LENGTH: 11
<212> TYPE: PRT
<213> ORGANISM: Homo sapiens
```

```
<400> SEQUENCE: 20

Asn Lys Met Trp Tyr Gly Leu Leu Gly Thr Lys
1               5                   10

<210> SEQ ID NO 21
<211> LENGTH: 10
<212> TYPE: PRT
<213> ORGANISM: Homo sapiens

<400> SEQUENCE: 21

Glu Lys Ala Pro Ser Leu Phe Ser Ser Arg
1               5                   10

<210> SEQ ID NO 22
<211> LENGTH: 18
<212> TYPE: PRT
<213> ORGANISM: Homo sapiens

<400> SEQUENCE: 22

Cys Ala Ala Cys Lys Ile Val Val His Thr Pro Cys Ile Glu Gln Leu
1               5                   10                  15

Glu Lys

<210> SEQ ID NO 23
<211> LENGTH: 20
<212> TYPE: PRT
<213> ORGANISM: Homo sapiens

<400> SEQUENCE: 23

Ser Gly Gly Asn Gln Gly Ala Lys Ile Ile Gln Ser Phe Leu Trp Tyr
1               5                   10                  15

Leu Asn Pro Arg
            20

<210> SEQ ID NO 24
<211> LENGTH: 10
<212> TYPE: PRT
<213> ORGANISM: Homo sapiens

<400> SEQUENCE: 24

Glu Ala Asn Pro Glu Lys Phe Asn Ser Arg
1               5                   10

<210> SEQ ID NO 25
<211> LENGTH: 13
<212> TYPE: PRT
<213> ORGANISM: Homo sapiens

<400> SEQUENCE: 25

Lys Thr Cys Gly Ser Ser Asp Val Leu Ala Gly Val Arg
1               5                   10

<210> SEQ ID NO 26
<211> LENGTH: 20
<212> TYPE: PRT
<213> ORGANISM: Homo sapiens

<400> SEQUENCE: 26

Leu Pro Pro Asp Ser Cys Pro Leu Leu Val Phe Val Asn Pro Lys Ser
1               5                   10                  15

Gly Gly Leu Lys
            20
```

```
<210> SEQ ID NO 27
<211> LENGTH: 10
<212> TYPE: PRT
<213> ORGANISM: Homo sapiens

<400> SEQUENCE: 27

Glu Glu Glu Pro Gly Lys Phe Thr Ser Arg
1               5                   10

<210> SEQ ID NO 28
<211> LENGTH: 16
<212> TYPE: PRT
<213> ORGANISM: Homo sapiens

<400> SEQUENCE: 28

Asp Leu Lys Pro Glu Asn Val Leu Leu Asp Ala His Met Asn Ala Lys
1               5                   10                  15

<210> SEQ ID NO 29
<211> LENGTH: 16
<212> TYPE: PRT
<213> ORGANISM: Homo sapiens

<400> SEQUENCE: 29

Asp Leu Lys Ser Asn Asn Ile Phe Leu His Glu Asp Leu Thr Val Lys
1               5                   10                  15

<210> SEQ ID NO 30
<211> LENGTH: 16
<212> TYPE: PRT
<213> ORGANISM: Homo sapiens

<400> SEQUENCE: 30

Asp Leu Lys Pro Gln Asn Leu Leu Ile Asp Asp Lys Gly Thr Ile Lys
1               5                   10                  15

<210> SEQ ID NO 31
<211> LENGTH: 16
<212> TYPE: PRT
<213> ORGANISM: Homo sapiens

<400> SEQUENCE: 31

Asp Leu Lys Pro Gln Asn Leu Leu Ile Asn Thr Glu Gly Ala Ile Lys
1               5                   10                  15

<210> SEQ ID NO 32
<211> LENGTH: 11
<212> TYPE: PRT
<213> ORGANISM: Homo sapiens

<400> SEQUENCE: 32

Asp Leu Lys Pro Gln Asn Leu Leu Ile Asn Arg
1               5                   10

<210> SEQ ID NO 33
<211> LENGTH: 8
<212> TYPE: PRT
<213> ORGANISM: Homo sapiens

<400> SEQUENCE: 33

Val Ala Ile Lys Ile Ile Ser Lys
1               5
```

```
<210> SEQ ID NO 34
<211> LENGTH: 22
<212> TYPE: PRT
<213> ORGANISM: Homo sapiens

<400> SEQUENCE: 34

Val Ser Asp Phe Gly Leu Thr Lys Glu Ala Ser Ser Thr Gln Asp Thr
1               5                   10                  15

Gly Lys Leu Pro Val Lys
            20

<210> SEQ ID NO 35
<211> LENGTH: 13
<212> TYPE: PRT
<213> ORGANISM: Homo sapiens

<400> SEQUENCE: 35

Asp Leu Lys Pro Ser Asn Ile Phe Leu Val Asp Thr Lys
1               5                   10

<210> SEQ ID NO 36
<211> LENGTH: 17
<212> TYPE: PRT
<213> ORGANISM: Homo sapiens

<400> SEQUENCE: 36

Thr Ser Val Ala Val Lys Thr Cys Lys Glu Asp Leu Pro Gln Glu Leu
1               5                   10                  15

Lys

<210> SEQ ID NO 37
<211> LENGTH: 27
<212> TYPE: PRT
<213> ORGANISM: Homo sapiens

<400> SEQUENCE: 37

Ala Ile Gln Phe Leu His Gln Asp Ser Pro Ser Leu Ile His Gly Asp
1               5                   10                  15

Ile Lys Ser Ser Asn Val Leu Leu Asp Glu Arg
            20                  25

<210> SEQ ID NO 38
<211> LENGTH: 9
<212> TYPE: PRT
<213> ORGANISM: Homo sapiens

<400> SEQUENCE: 38

Leu Phe Ala Val Lys Cys Ile Pro Lys
1               5

<210> SEQ ID NO 39
<211> LENGTH: 15
<212> TYPE: PRT
<213> ORGANISM: Homo sapiens

<400> SEQUENCE: 39

Ile Pro Thr Gly Gln Glu Tyr Ala Ala Lys Ile Ile Asn Thr Lys
1               5                   10                  15

<210> SEQ ID NO 40
<211> LENGTH: 14
<212> TYPE: PRT
<213> ORGANISM: Homo sapiens
```

```
<400> SEQUENCE: 40

Thr Ser Thr Gln Glu Tyr Ala Ala Lys Ile Ile Asn Thr Lys
1               5                   10

<210> SEQ ID NO 41
<211> LENGTH: 15
<212> TYPE: PRT
<213> ORGANISM: Homo sapiens

<400> SEQUENCE: 41

Leu Thr Asp Phe Gly Leu Ser Lys Glu Ala Ile Asp His Glu Lys
1               5                   10                  15

<210> SEQ ID NO 42
<211> LENGTH: 16
<212> TYPE: PRT
<213> ORGANISM: Homo sapiens

<400> SEQUENCE: 42

Asp Leu Lys Pro Glu Asn Ile Leu Leu Asp Glu Glu Gly His Ile Lys
1               5                   10                  15

<210> SEQ ID NO 43
<211> LENGTH: 14
<212> TYPE: PRT
<213> ORGANISM: Homo sapiens

<400> SEQUENCE: 43

Val Leu Gly Thr Gly Ala Tyr Gly Lys Val Phe Leu Val Arg
1               5                   10

<210> SEQ ID NO 44
<211> LENGTH: 16
<212> TYPE: PRT
<213> ORGANISM: Homo sapiens

<400> SEQUENCE: 44

Asp Leu Lys Pro Glu Asn Ile Met Leu Asn His Gln Gly His Val Lys
1               5                   10                  15

<210> SEQ ID NO 45
<211> LENGTH: 16
<212> TYPE: PRT
<213> ORGANISM: Homo sapiens

<400> SEQUENCE: 45

Asp Leu Lys Pro Glu Asn Ile Met Leu Ser Ser Gln Gly His Ile Lys
1               5                   10                  15

<210> SEQ ID NO 46
<211> LENGTH: 9
<212> TYPE: PRT
<213> ORGANISM: Homo sapiens

<400> SEQUENCE: 46

Ala Leu Tyr Ala Thr Lys Thr Leu Arg
1               5

<210> SEQ ID NO 47
<211> LENGTH: 9
<212> TYPE: PRT
<213> ORGANISM: Homo sapiens

<400> SEQUENCE: 47
```

```
Asp Ile Lys Gly Ala Asn Ile Leu Arg
1               5

<210> SEQ ID NO 48
<211> LENGTH: 16
<212> TYPE: PRT
<213> ORGANISM: Homo sapiens

<400> SEQUENCE: 48

Asp Ile Lys Gly Ala Asn Ile Phe Leu Thr Ser Ser Gly Leu Ile Lys
1               5                   10                  15

<210> SEQ ID NO 49
<211> LENGTH: 16
<212> TYPE: PRT
<213> ORGANISM: Homo sapiens

<400> SEQUENCE: 49

Asp Ile Lys Gly Ala Asn Ile Leu Leu Thr Asp Asn Gly His Val Lys
1               5                   10                  15

<210> SEQ ID NO 50
<211> LENGTH: 16
<212> TYPE: PRT
<213> ORGANISM: Homo sapiens

<400> SEQUENCE: 50

Asp Ile Lys Gly Gln Asn Val Leu Leu Thr Glu Asn Ala Glu Val Lys
1               5                   10                  15

<210> SEQ ID NO 51
<211> LENGTH: 14
<212> TYPE: PRT
<213> ORGANISM: Homo sapiens

<400> SEQUENCE: 51

Asn Val His Thr Gly Glu Leu Ala Ala Val Lys Ile Ile Lys
1               5                   10

<210> SEQ ID NO 52
<211> LENGTH: 16
<212> TYPE: PRT
<213> ORGANISM: Homo sapiens

<400> SEQUENCE: 52

Asp Ile Lys Gly Ala Asn Ile Leu Leu Thr Asp His Gly Asp Val Lys
1               5                   10                  15

<210> SEQ ID NO 53
<211> LENGTH: 9
<212> TYPE: PRT
<213> ORGANISM: Homo sapiens

<400> SEQUENCE: 53

Glu Val Ala Val Lys Ile Ile Asp Lys
1               5

<210> SEQ ID NO 54
<211> LENGTH: 12
<212> TYPE: PRT
<213> ORGANISM: Homo sapiens

<400> SEQUENCE: 54

Asp Val Lys Pro Ser Asn Ile Leu Val Asn Ser Arg
1               5                   10
```

<210> SEQ ID NO 55
<211> LENGTH: 11
<212> TYPE: PRT
<213> ORGANISM: Homo sapiens

<400> SEQUENCE: 55

Asp Val Lys Pro Ser Asn Val Leu Ile Asn Lys
1               5                   10

<210> SEQ ID NO 56
<211> LENGTH: 11
<212> TYPE: PRT
<213> ORGANISM: Homo sapiens

<400> SEQUENCE: 56

Asp Ile Lys Pro Ser Asn Ile Leu Leu Asp Arg
1               5                   10

<210> SEQ ID NO 57
<211> LENGTH: 12
<212> TYPE: PRT
<213> ORGANISM: Homo sapiens

<400> SEQUENCE: 57

His Val Pro Ser Gly Gln Ile Met Ala Val Lys Arg
1               5                   10

<210> SEQ ID NO 58
<211> LENGTH: 11
<212> TYPE: PRT
<213> ORGANISM: Homo sapiens

<400> SEQUENCE: 58

Ser Lys Asn Ile Phe Leu Thr Gln Asn Gly Lys
1               5                   10

<210> SEQ ID NO 59
<211> LENGTH: 12
<212> TYPE: PRT
<213> ORGANISM: Homo sapiens

<400> SEQUENCE: 59

Val Met Asp Pro Thr Lys Ile Leu Ile Thr Gly Lys
1               5                   10

<210> SEQ ID NO 60
<211> LENGTH: 10
<212> TYPE: PRT
<213> ORGANISM: Homo sapiens

<400> SEQUENCE: 60

Phe Lys Glu Tyr Cys Pro Gln Val Phe Arg
1               5                   10

<210> SEQ ID NO 61
<211> LENGTH: 20
<212> TYPE: PRT
<213> ORGANISM: Homo sapiens

<400> SEQUENCE: 61

Cys Phe Glu Ile Ser Asp Ala Asp Thr Lys Glu Val Phe Ala Gly Lys
1               5                   10                  15

Ile Val Pro Lys

```
                20

<210> SEQ ID NO 62
<211> LENGTH: 16
<212> TYPE: PRT
<213> ORGANISM: Homo sapiens

<400> SEQUENCE: 62

Asp Met Lys Ser Asn Asn Ile Phe Leu His Glu Gly Leu Thr Val Lys
1               5                   10                  15

<210> SEQ ID NO 63
<211> LENGTH: 16
<212> TYPE: PRT
<213> ORGANISM: Homo sapiens

<400> SEQUENCE: 63

Asp Leu Lys Ala Gly Asn Ile Leu Phe Thr Leu Asp Gly Asp Ile Lys
1               5                   10                  15

<210> SEQ ID NO 64
<211> LENGTH: 22
<212> TYPE: PRT
<213> ORGANISM: Homo sapiens

<400> SEQUENCE: 64

Asp Thr Val Thr Ile His Ser Val Gly Gly Thr Ile Thr Ile Leu Pro
1               5                   10                  15

Thr Lys Thr Lys Pro Lys
                20

<210> SEQ ID NO 65
<211> LENGTH: 16
<212> TYPE: PRT
<213> ORGANISM: Homo sapiens

<400> SEQUENCE: 65

Asp Leu Lys Ala Gly Asn Val Leu Met Thr Leu Glu Gly Asp Ile Arg
1               5                   10                  15

<210> SEQ ID NO 66
<211> LENGTH: 16
<212> TYPE: PRT
<213> ORGANISM: Homo sapiens

<400> SEQUENCE: 66

Asp Ile Lys Ala Gly Asn Ile Leu Leu Asn Thr Glu Gly His Ala Lys
1               5                   10                  15

<210> SEQ ID NO 67
<211> LENGTH: 12
<212> TYPE: PRT
<213> ORGANISM: Homo sapiens

<400> SEQUENCE: 67

Asp Thr Gly His Val Tyr Ala Met Lys Ile Leu Arg
1               5                   10

<210> SEQ ID NO 68
<211> LENGTH: 10
<212> TYPE: PRT
<213> ORGANISM: Homo sapiens

<400> SEQUENCE: 68
```

```
Glu Val Val Ala Ile Lys Cys Val Ala Lys
1               5                   10
```

```
<210> SEQ ID NO 69
<211> LENGTH: 28
<212> TYPE: PRT
<213> ORGANISM: Homo sapiens

<400> SEQUENCE: 69

Pro Leu Leu Val Phe Ile Asn Pro Lys Ser Gly Gly Lys Gln Gly Gln
1               5                   10                  15

Ser Val Leu Trp Lys Phe Gln Tyr Ile Leu Asn Pro
            20                  25
```

```
<210> SEQ ID NO 70
<211> LENGTH: 28
<212> TYPE: PRT
<213> ORGANISM: Homo sapiens

<400> SEQUENCE: 70

Pro Leu Leu Ile Phe Ile Asn Ser Lys Ser Gly Asp His Gln Gly Ile
1               5                   10                  15

Val Phe Leu Arg Lys Phe Lys Gln Tyr Leu Asn Pro
            20                  25
```

```
<210> SEQ ID NO 71
<211> LENGTH: 28
<212> TYPE: PRT
<213> ORGANISM: Homo sapiens

<400> SEQUENCE: 71

Pro Leu Ile Ile Leu Ala Asn Ser Arg Ser Gly Thr Asn Met Gly Glu
1               5                   10                  15

Gly Leu Leu Gly Glu Phe Arg Ile Leu Leu Asn Pro
            20                  25
```

```
<210> SEQ ID NO 72
<211> LENGTH: 28
<212> TYPE: PRT
<213> ORGANISM: Homo sapiens

<400> SEQUENCE: 72

Pro Leu Leu Val Phe Val Asn Pro Lys Ser Gly Gly Asn Gln Gly Ala
1               5                   10                  15

Lys Ile Ile Gln Ser Phe Leu Trp Tyr Leu Asn Pro
            20                  25
```

```
<210> SEQ ID NO 73
<211> LENGTH: 28
<212> TYPE: PRT
<213> ORGANISM: Homo sapiens

<400> SEQUENCE: 73

Pro Leu Leu Val Phe Val Asn Pro Lys Ser Gly Gly Leu Lys Gly Arg
1               5                   10                  15

Asp Leu Leu Cys Ser Phe Arg Lys Leu Leu Asn Pro
            20                  25
```

```
<210> SEQ ID NO 74
<211> LENGTH: 27
<212> TYPE: PRT
<213> ORGANISM: Homo sapiens
```

```
<400> SEQUENCE: 74

Phe His Leu Met Arg Glu Lys Tyr Pro Glu Lys Phe Asn Ser Arg Met
1               5                   10                  15

Lys Asn Lys Leu Trp Tyr Leu Glu Phe Ala Thr
            20                  25

<210> SEQ ID NO 75
<211> LENGTH: 27
<212> TYPE: PRT
<213> ORGANISM: Homo sapiens

<400> SEQUENCE: 75

Phe Asn Thr Arg Arg Asp Glu His Pro Gly Gln Tyr Asn Ser Arg Leu
1               5                   10                  15

Lys Asn Lys Met Trp Tyr Gly Leu Leu Gly Thr
            20                  25

<210> SEQ ID NO 76
<211> LENGTH: 27
<212> TYPE: PRT
<213> ORGANISM: Homo sapiens

<400> SEQUENCE: 76

Phe His Ala His Arg Glu Lys Ala Pro Ser Leu Phe Ser Ser Arg Ile
1               5                   10                  15

Leu Asn Lys Ala Val Tyr Leu Phe Tyr Gly Thr
            20                  25

<210> SEQ ID NO 77
<211> LENGTH: 27
<212> TYPE: PRT
<213> ORGANISM: Homo sapiens

<400> SEQUENCE: 77

Phe His Glu Ser Arg Glu Ala Asn Pro Glu Lys Phe Asn Ser Arg Phe
1               5                   10                  15

Arg Asn Lys Met Phe Tyr Ala Gly Thr Ala Phe
            20                  25

<210> SEQ ID NO 78
<211> LENGTH: 27
<212> TYPE: PRT
<213> ORGANISM: Homo sapiens

<400> SEQUENCE: 78

Phe His Gln Ala Arg Glu Glu Glu Pro Gly Lys Phe Thr Ser Arg Leu
1               5                   10                  15

His Asn Lys Gly Val Tyr Val Arg Val Gly Leu
            20                  25
```

```
<210> SEQ ID NO 79
<211> LENGTH: 17
<212> TYPE: PRT
<213> ORGANISM: Homo sapiens

<400> SEQUENCE: 79

Thr Ser Val Ala Val Lys Thr Cys Lys Glu Asp Leu Pro Gln Glu Leu
1               5                   10                  15

Lys

<210> SEQ ID NO 80
<211> LENGTH: 10
<212> TYPE: PRT
<213> ORGANISM: Homo sapiens

<400> SEQUENCE: 80

Leu Asp Gly Cys Cys Tyr Ala Val Lys Arg
1               5                   10

<210> SEQ ID NO 81
<211> LENGTH: 11
<212> TYPE: PRT
<213> ORGANISM: Homo sapiens

<400> SEQUENCE: 81

Tyr Val Ala Val Lys Ile His Gln Leu Asn Lys
1               5                   10

<210> SEQ ID NO 82
<211> LENGTH: 12
<212> TYPE: PRT
<213> ORGANISM: Homo sapiens

<400> SEQUENCE: 82

Tyr Ile Lys Tyr Asn Ser Asn Ser Gly Phe Val Arg
1               5                   10

<210> SEQ ID NO 83
<211> LENGTH: 16
<212> TYPE: PRT
<213> ORGANISM: Homo sapiens

<400> SEQUENCE: 83

Asp Met Lys Ser Asn Asn Ile Phe Leu His Glu Gly Leu Thr Val Lys
1               5                   10                  15
```

COMPOSITIONS AND USES THEREOF

CROSS-REFERENCE TO RELATED APPLICATIONS

This application is a U.S. National Stage Filing under 35 U.S.C. 371 from International Application No. PCT/US2018/039615, filed Jun. 26, 2018, which claims the benefit of priority to U.S. Provisional Appl. Ser. No. 62/524,738, filed Jun. 26, 2017, which are incorporated by reference in their entireties.

BACKGROUND

Diacylglycerols (DAGs) and phosphatidic acid (PA) play roles in biology as basic components of membranes, intermediates in lipid metabolism, and secondary messengers in cellular signaling (Carrasco and Merida, 2007; Fang et al., 2001). Cells regulate intracellular DAG and PA levels through metabolic networks that utilize distinct enzymes to produce or consume these secondary messengers/metabolites (Brown et al., 2017; Carrasco and Merida, 2007; Hsu et al., 2012; Shulga et al., 2011). One such enzymatic pathway of signal transduction is adenosine triphosphate . . .

(ATP)-dependent phosphorylation of DAGs to biosynthesize phosphatidic acid (PA) by a set of lipid kinases collectively known as diacylglycerol kinases (Shulga et al., 2011) (DGKs). DAG and PA are lipid messengers that alter localization (Takai et al., 1979), activation (Newton and Koshland, 1989), and protein-protein interactions (Fang et al., 2001) of distinct sets of receptor proteins.

SUMMARY

Provided herein are compounds and uses thereof. For Example, this disclosure relates to at least the following compounds, others disclosed herein and uses thereof:

A compound according to formula (I), formula (II), formula (III), formula (IV), or formula (V):

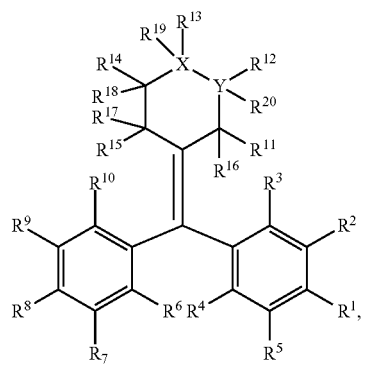

(I)

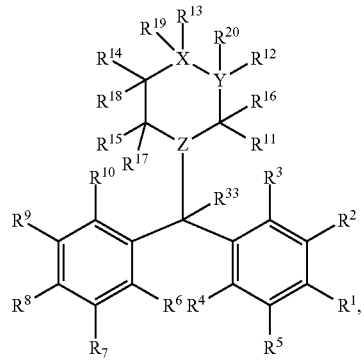

(II)

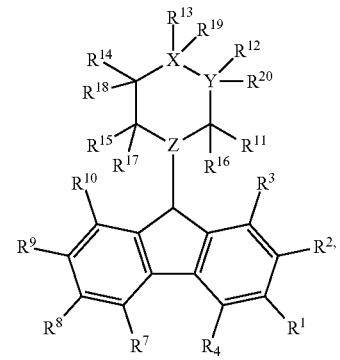

(III)

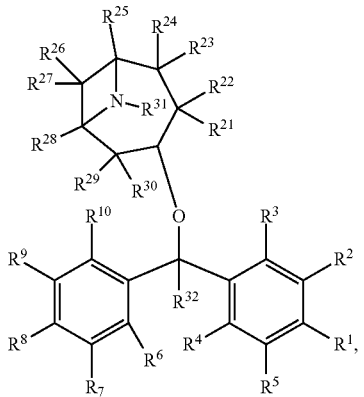

(IV)

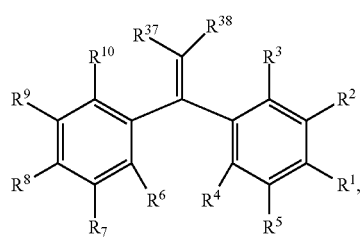

(V)

or a pharmaceutically acceptable salt, polymorph, prodrug, or solvate thereof;

X is selected from the group consisting of: $-CR^{19}R^{13}-$, $-NR^{35}-$;

Y is selected from the group consisting of: $-CR^{12}R^{20}-$, $-NR^{36}-$;

and X is selected from the group consisting of:

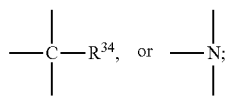

$R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{22}$, $R^{23}$, $R^{24}$, $R^{25}$, $R^{26}$, $R^{27}$, $R^{28}$, $R^{29}$, $R^{30}$, $R^{31}$, $R^{32}$, $R^{33}$, $R^{34}$, $R^{35}$, $R^{36}$, $R^{37}$, and $R^{38}$, independently, are selected from the group consisting of —H, —F, —Cl, —Br and substituted or unsubstituted ($C_1$-$C_{100}$) hydrocarbyl.

DRAWINGS

Figure 1:
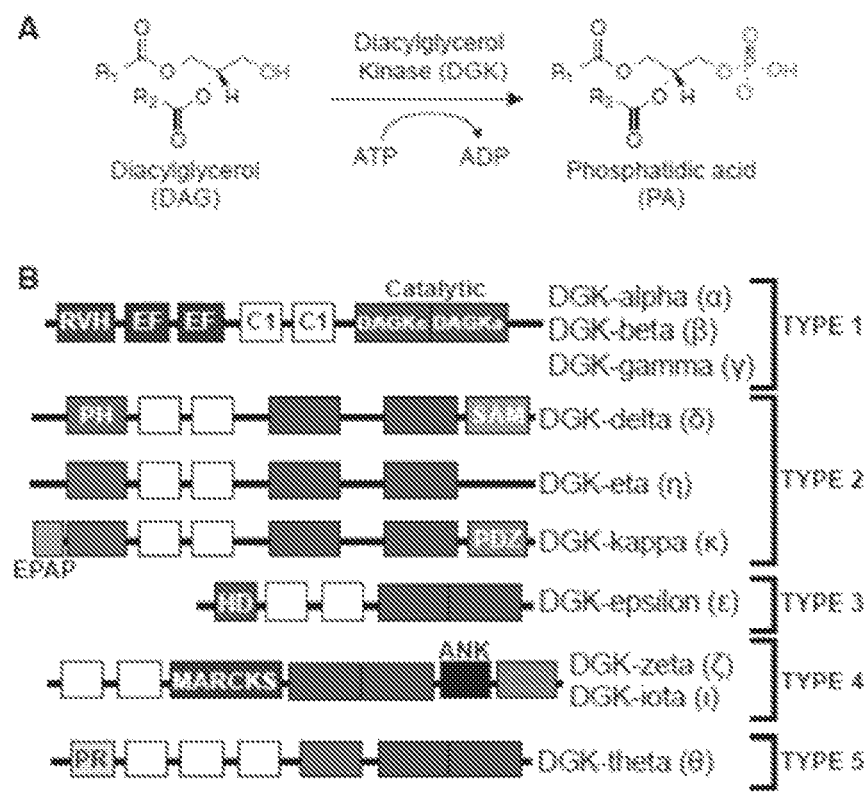

FIGS. 1A-B. Mammalian diacylglycerol kinase (DGK) superfamily. (A) DGK enzymes catalyze transfer of phosphate from ATP to diacylglycerol (DAG) to biosynthesize phosphatidic acid (PA). The molecular structure of fatty acyl chains regulates functional properties of DAG and PA lipids. (B) The ten DGK isoforms identified to date are divided into five principal subtypes based on organization of structural motifs. Alternative splicing of certain DGK subtypes can generate additional structural diversity. RVH: recoverin homology domain; EF: EF Hands motif; C1: atypical/typical C1 domain; PH: pleckstrin homology domain; SAM: sterile alpha motif; EPAP: Glu-Pro-Ala-Pro repeats (SEQ ID NO: 1); PDZ: protein-protein interactions; HD: hydrophobic domain; MARCKS: myristolated alanine-rich C kinase substrate domain; ANK: Ankyrin repeats; PR: proline-rich region.

Figure 2:
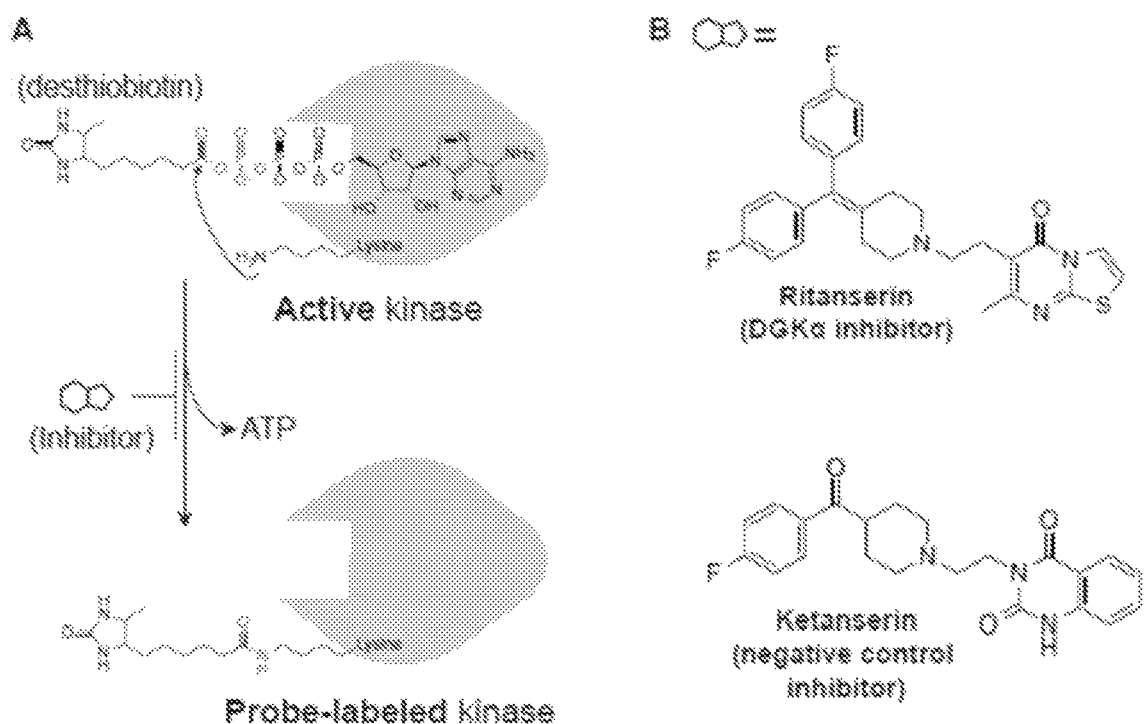

FIGS. 2A-B. Activity-based probes and inhibitors for functional analysis of DGKs. (A) Chemical structure and mechanism of ATP acyl phosphate probe labeling. The ATP binding group mediates interactions with lipid and protein kinases to place the reactive acyl phosphate group in proximity of lysines in the active site. The side chain amino group of lysine covalently reacts with probe, releasing ATP, and covalently attaches desthiobiotin to kinase through an amide bond. (B) The DGKα inhibitor ritanserin and matching negative control inhibitor ketanserin.

Figure 3:
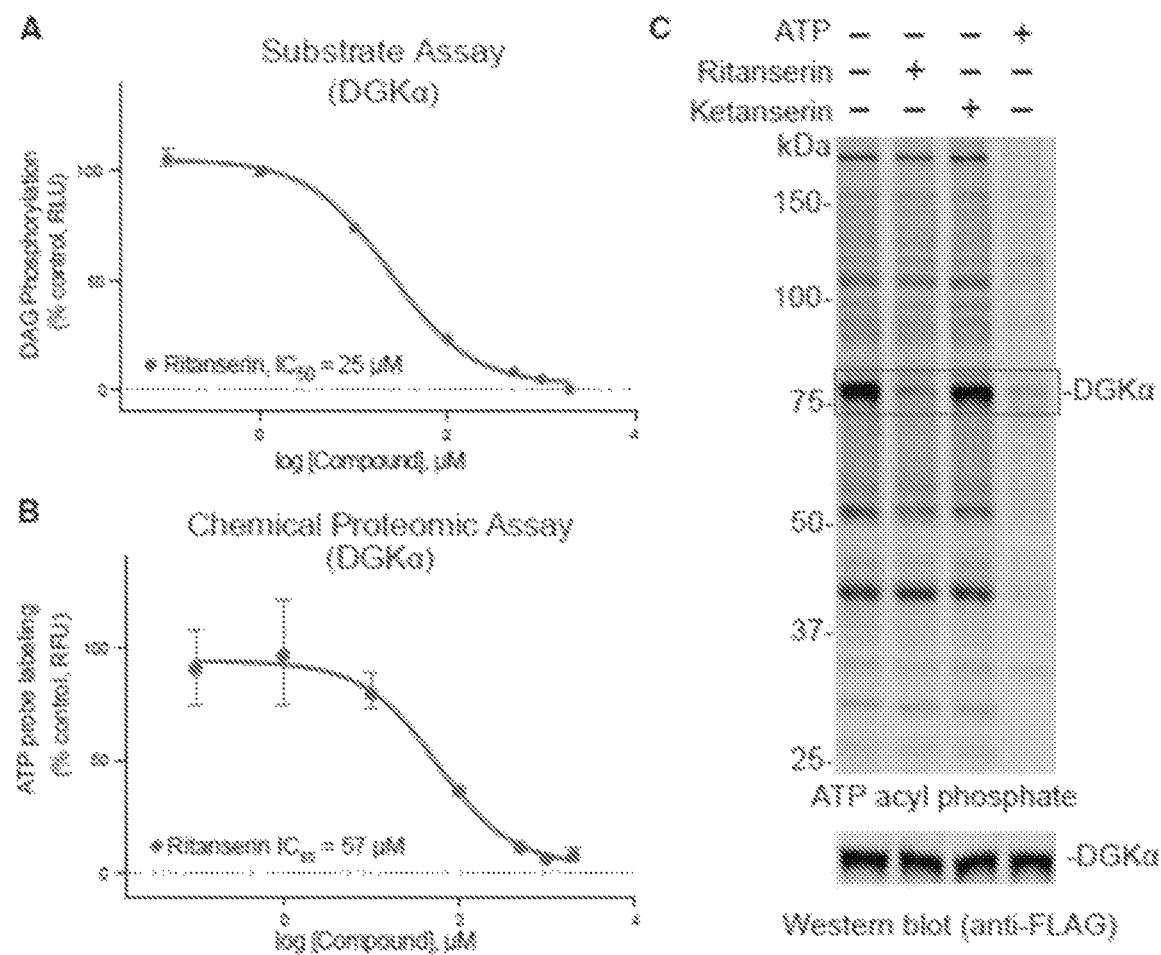

FIGS. 3A-C. ATP acyl phosphates enable gel-based activity-based profiling of DGKα. (A) In vitro $IC_{50}$ values for DGKα inhibition by ritanserin as measured by DAG phosphorylation substrate assay described in FIG. 9. Data shown are mean+/− SEM. for triplicate measurements. Results are representative of two independent biological replicates. 95% confidence intervals for $IC_{50}$ values: 20-30 µM. (B) Gel-based ATP acyl phosphate assay was used to determine in vitro $IC_{50}$ values for DGKα inhibition by ritanserin (95% confidence intervals for $IC_{50}$ values: 17-192 µM). Details of the assay and representative gels used to calculate potency values can be found in FIG. 10. (C) DGKα-HEK293T soluble proteomes were pretreated with ritanserin (10 µM), ketanserin (100 µM), or ATP (1 mM) for 30 min prior to addition of ATP acyl phosphate probe (10 µM, 30 min) and gel-based analysis as described in FIG. 10. Pretreatment with ritanserin but not ketanserin blocked probe labeling of ~80 kDa recombinant DGKα. Western blot analysis (anti-FLAG, 0.8 µg/mL) confirmed equivalent recombinant protein expression across treatment conditions.

Figure 4:
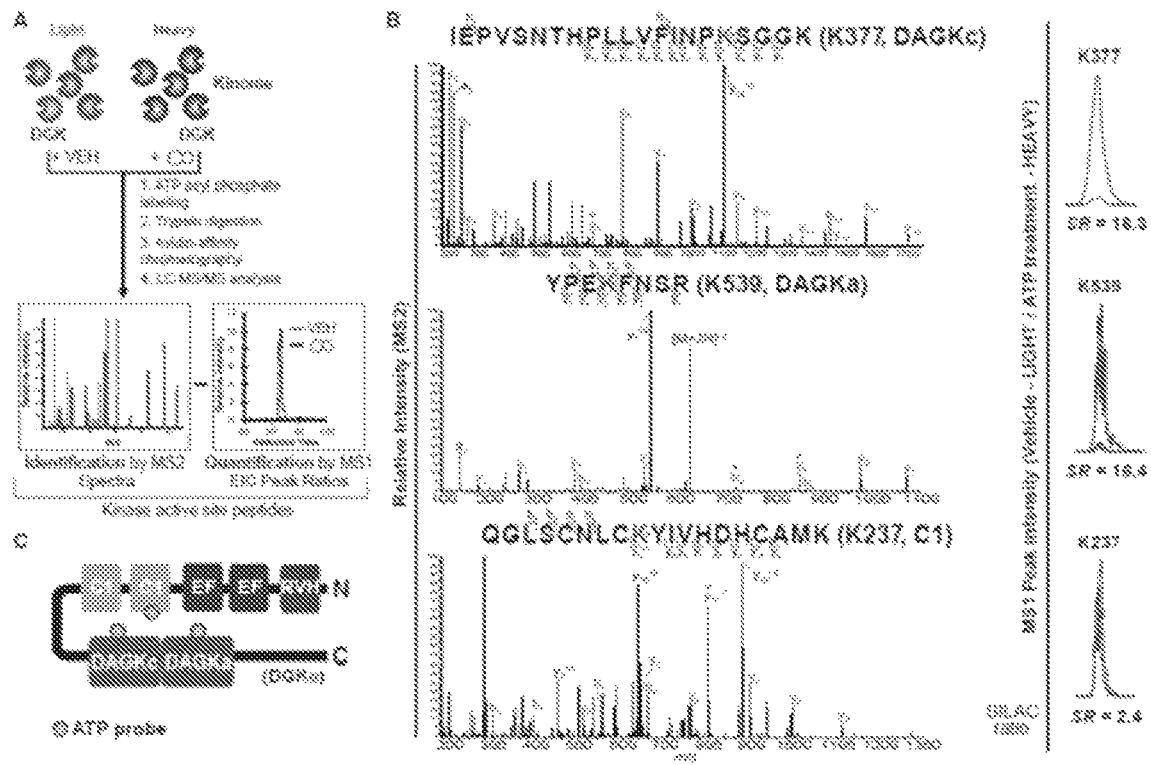

FIGS. 4A-C. Elucidation of ATP and ligand-binding sites of DGKα by quantitative chemical proteomics. (A) Schematic of quantitative LC-MS proteomics workflow to identify ligand binding sites of recombinant DGKs using ATP acyl phosphate probe. See STAR Methods for more details. (B) Left-MS2 spectra of probe-modified peptides corresponding to the active site of DGKα. Major b- and y-ion fragments derived from neutral losses of the precursor (M) are indicated on spectrum in red. An asterisk denotes fragments containing probe-modified lysine residues corresponding to the red-labeled lysine shown in the peptide sequence. Right-MS1 extracted ion chromatograms of probe-modified peptides with corresponding SILAC ratios quantifying vehicle-treated (light): compound-treated (heavy). (C) Schematic of DGKα showing domains where ATP probe binding is detected by quantitative chemical proteomics. Orange circles represent ATP probe binding at K237 of the C1 domain, K377 of the DAGKc domain, and K539 of the DAGKa domain. (SEQ ID NOs: 2-4)

FIGS. 5A-C. Chemical proteomic profiling of the DGK superfamily. (A) Heatmap showing SILAC ratios for probe-binding sites of respective DGK isoforms in ATP (1 mM, 30 min)—versus DMSO vehicle-treated recombinant HEK293T proteomes. DGK ATP binding sites are defined by SR >5. (B-C) Sequence similarity of ATP binding sites of DGK isoforms measured by quantitative proteomics. Multiple sequence alignments of probe-modified peptides were performed using Clustal Omega and results analyzed by sequence logos (See STAR Methods for details) to search for common motifs within the DAGKc (B) and DAGKa (C) ATP-binding sites of DGKs. The height of each stack denotes sequence conservation at the respective position (measured in bits). The height of individual residues within the stack indicates the relative frequency of corresponding amino acids at that position. The numbers in parentheses indicate the number of DGKs that show modification at the respective probe-modified lysine. Color scheme for amino acids in sequence logos is as follows: hydrophilic, blue; neutral, green; hydrophobic, black. Probe modified peptides used for sequence alignment and logo analysis can be found in FIG. 13 and Table 1 and 1A.

Figure 6:
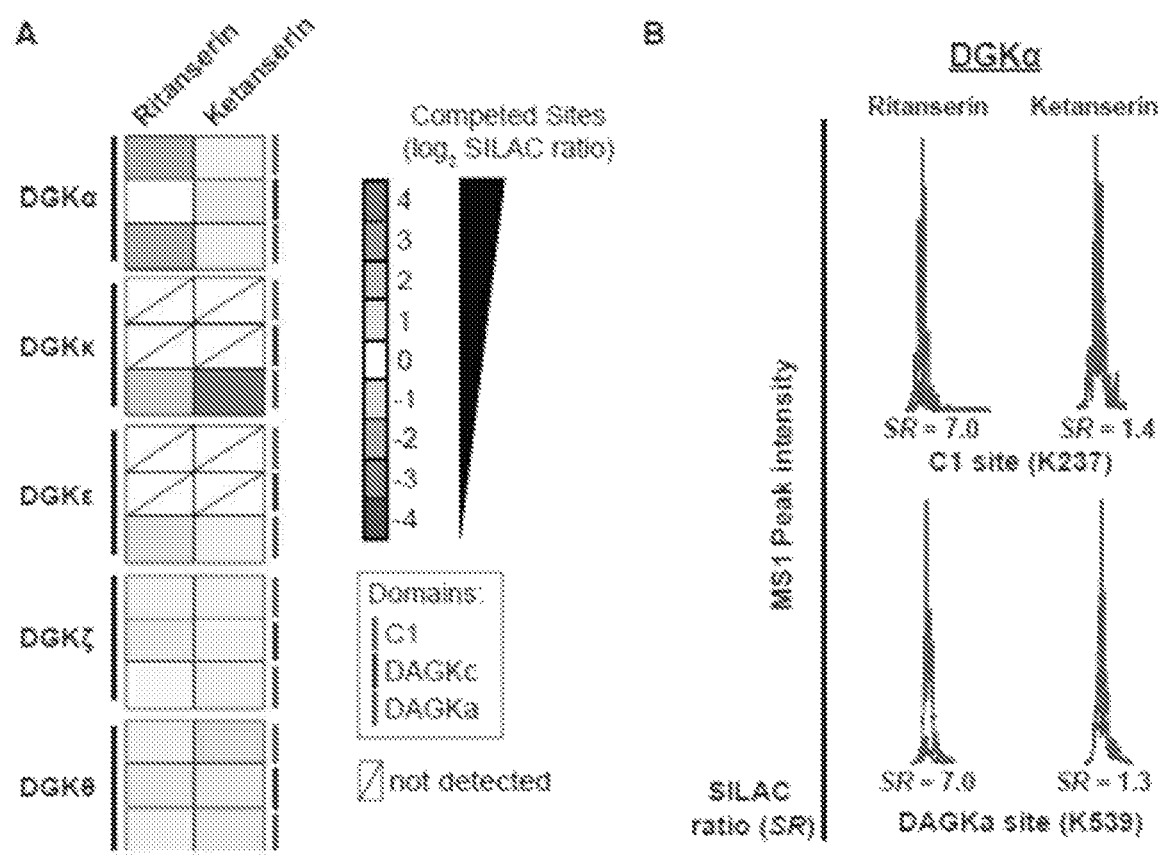
Figure 7:
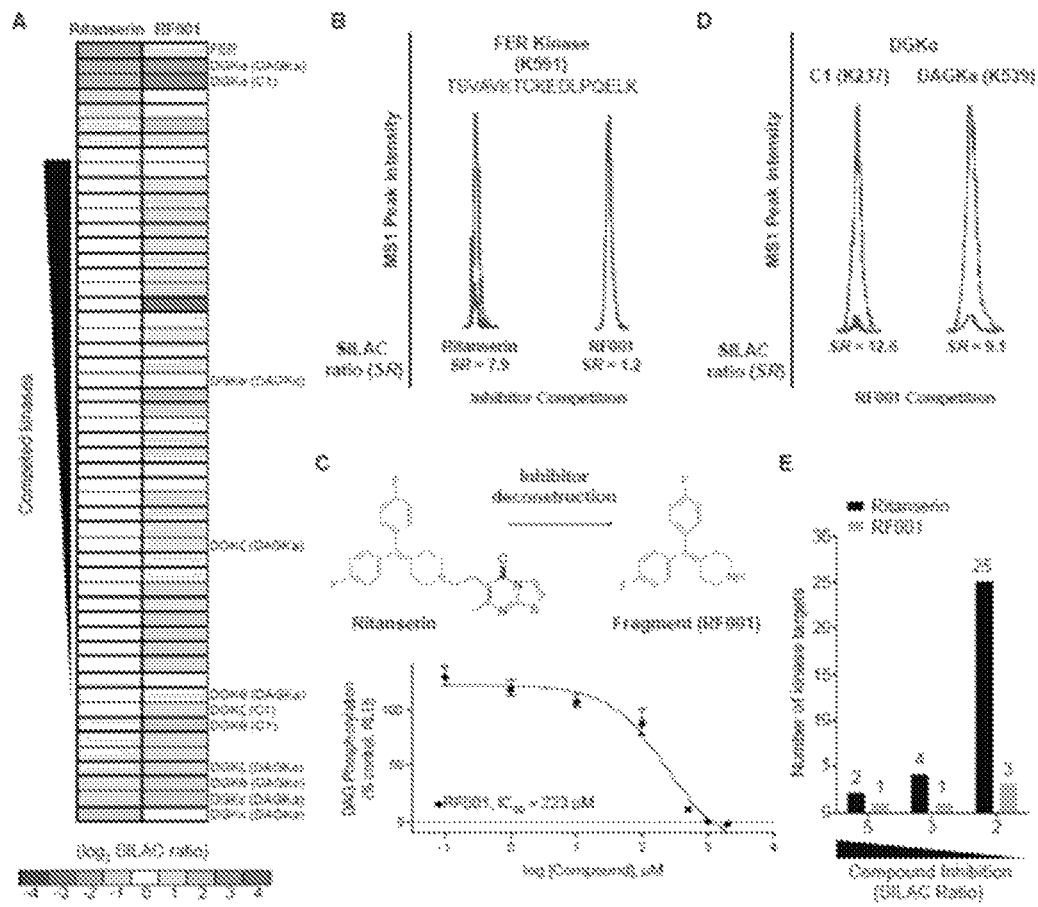

FIGS. 6A-B. Inhibitor profiling of the DGK superfamily. (A) Heat map showing SILAC ratios of DGK probe-binding sites that are competed (SR >5) with ritanserin-versus DMSO vehicle control-treated samples. Lack of competition at respective sites in ketanserin-treated samples indicates ritanserin competition was specific. (B) Representative extracted ion chromatograms (MS1) of probe modified peptides from DGKα C1 and DAGKa domains, which represent the primary sites of binding for ritanserin. Ketanserin is inactive at these same sites. For all studies, proteomes were pretreated with compounds (100 µM) for 30 min prior to labeling with ATP acyl phosphate probe (10 µM, 30 min).

Figure 9:
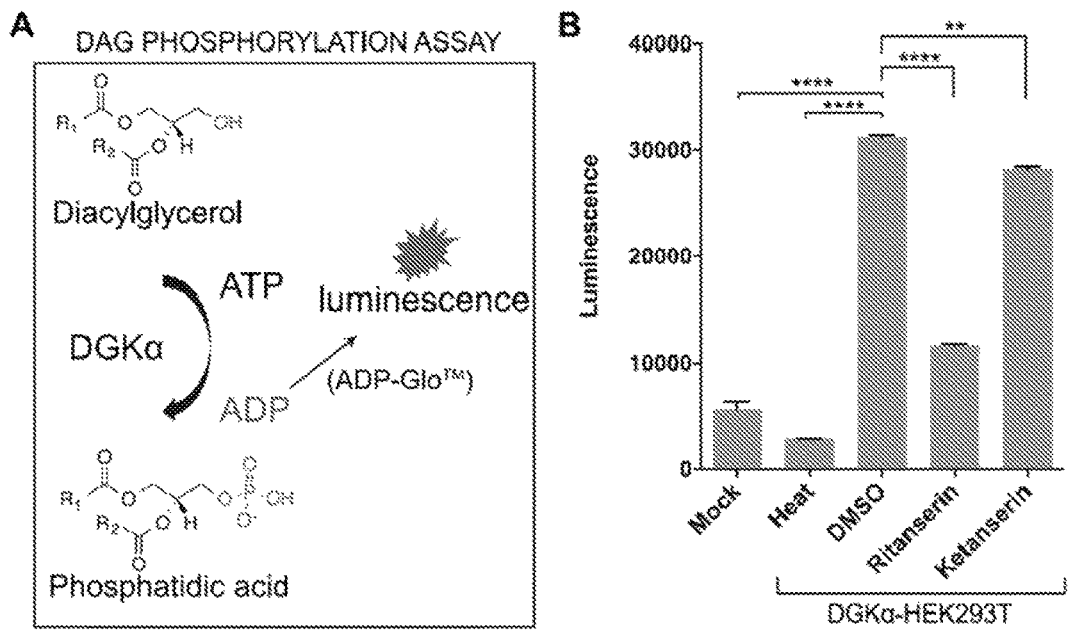
Figure 10:
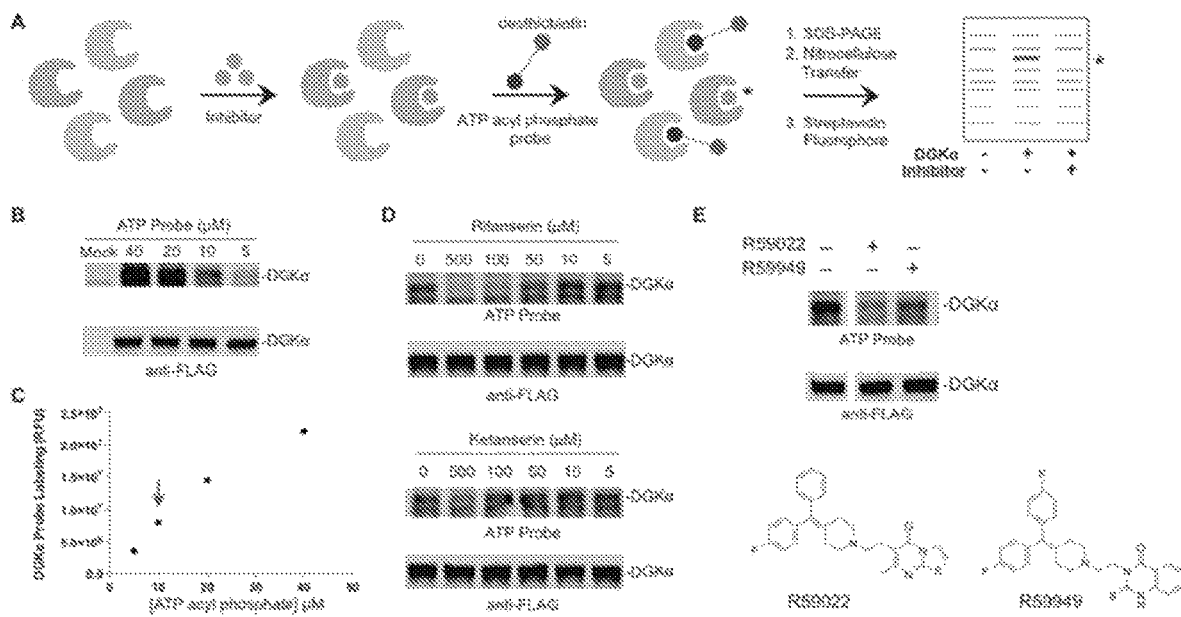

FIGS. 7A-E. Discovery of a lead fragment inhibitor of DGKα by chemical proteomics. (A) Heat map showing potency and selectivity of ritanserin and RF001 against recombinant DGKs and native kinases detected in HEK293T proteomes. (B) Representative extracted ion chromatograms (MS1) of probe modified peptide from FER, showing potent competition with ritanserin but not RF001. (C) Ritanserin deconstruction to identify the fragment RF001, which shows concentration-dependent blockade of recombinant DGKα as measured by substrate assay (FIG. 9). Data shown are mean+/− SEM. for triplicate measurements. Results are representative of two independent biological replicates. 95% confidence intervals for $IC_{50}$ values: 120-414 µM. Dotted line represents background activity detected in non-transfected HEK293T proteomes. (D) Representative extracted ion chromatograms (MS1) showing the primary sites of binding for RF001 against DGKα. Quantified SILAC ratios shown are averages of two biological replicates. (E) Bar graph comparing the total number of kinase targets (recombinant DGKs and native kinases in HEK293T proteomes) observed with potent (SR >5), moderate (SR >3), and weak competition (SR >2) at respective probe-binding sites in ritanserin-versus RF001-treated samples. For quantitative LC-MS experiments, proteomes were pretreated with compounds (100 μM) for 30 min prior to labeling with ATP acyl phosphate probe (10 μM, 30 min).

Figure 8:
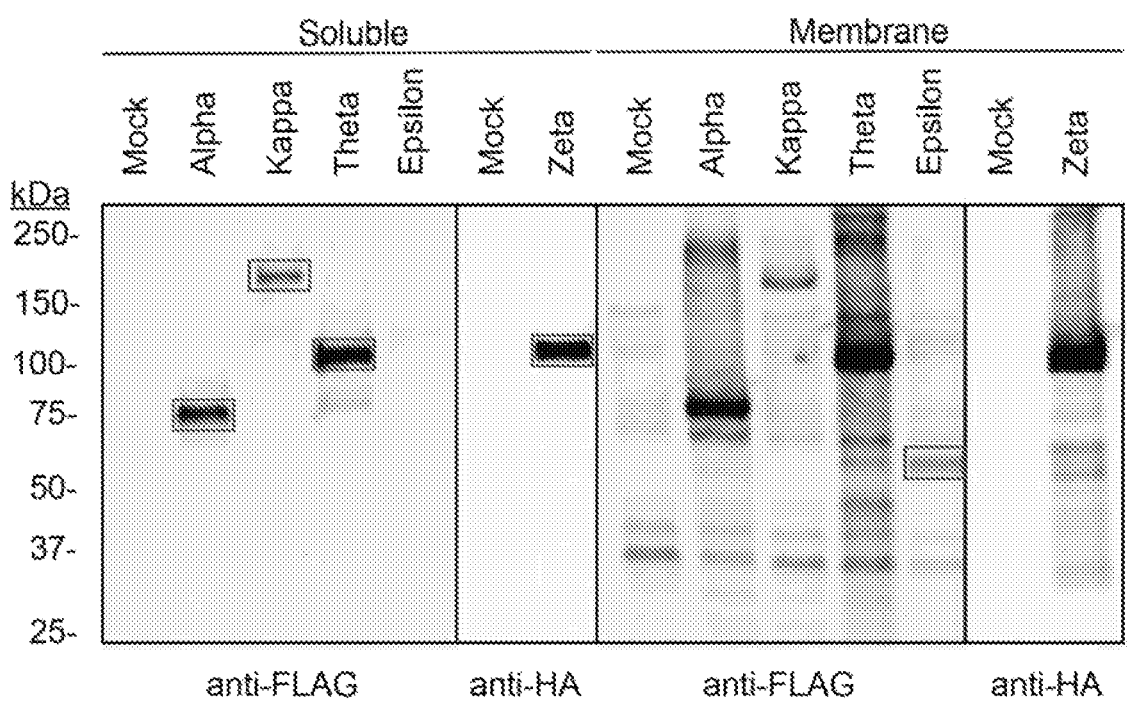

FIG. 8. Related to FIGS. 5-7. Western blot analysis of recombinant overexpressed DGK isoforms. DGK isoforms were recombinantly expressed in HEK293T cells and proteomes subjected to western blot analysis (anti-FLAG, 0.8 μg/mL; anti-HA, 0.1 μg/mL). Soluble fractions were used for analysis with the exception of epsilon, which is expressed predominantly in the membrane fraction (highlighted by red boxes).

FIGS. 9A-B. Related to FIGS. 3 and 7. Measuring activity and inhibition of recombinant DGKα in HEK293T cells by substrate assay. (A) The ADP-glo assay measures ATP that has been converted to ADP by the action of kinases in the cell lysate though production of luminescent signal in proportion to ADP produced. (B) Production of active recombinant DGKα was determined by enhanced activity in DGKα-HEK293T versus mock-transfected soluble proteomes as measured using ADP-glo assay. The lack of activity with heat-denatured (95° C. for 5 min) DGKα-HEK293T proteomes supports that activity was specific for recombinant DGKα. Pretreatment with ritanserin but not ketanserin (100 μM compounds) resulted in ~80% blockade of recombinant DGKα activity. Data shown are mean+s.e.m. for two independent biological replicates; n=2 per group. ** P≤0.0001 for mock versus DGKα overexpressed group (DMSO);  P≤0.01, **** P≤0.0001 for vehicle-treated versus heat-denatured or inhibitor-treated DGKα overexpressed groups (DMSO).

FIGS. 10A-E. Related to FIG. 3. Optimization of gel-based ATP acyl phosphate assay for profiling DGK inhibitors. (A) Schematic of gel-based chemical proteomic analysis of recombinant DGKα activity. DGKα-HEK293T soluble proteomes were labeled with ATP acyl phosphate, proteins separated by SDS-PAGE, transferred to nitrocellulose, and desthiobiotin-modified proteins detected by streptavidin fluorophore and in-blot fluorescence. Pretreatment of proteomes with inhibitors blocks labeling at ATP probe binding sites, resulting in reductions in fluorescence signals to profile on- and off-targets of recombinant DGKα. (B) DGKα-HEK293T soluble proteomes were treated with ATP probe at the indicated concentrations for 30 min, quenched with gel loading buffer, and subjected to gel-based analysis as described above. (C) Integrated band intensities from these studies were plotted as a function of ATP probe concentrations to identify a suitable treatment condition for profiling of reversible inhibitors (10 μM ATP probe, 30 min; labeling reaction was ~40% complete). (D) DGKα-HEK293T soluble proteomes were pretreated with ritanserin or ketanserin for 30 min at the indicated concentrations followed by ATP probe labeling (10 UM, 30 min) and gel-based chemical proteomics analysis as described above. Ritanserin but not ketanserin showed concentration dependent blockade of ATP probe labeling. (E) Pretreatment with the widely used DGK inhibitors $R^{59022}$ and R59949 (100 μM compounds) also blocked DGKα probe labeling as measured by gel-based chemical proteomics. For all chemical proteomics studies, western blots (anti-FLAG, 0.8 μg/mL.) were included to confirm that changes in fluorescence were not due to variations in recombinant protein expression (bottom panels).

Figure 11:
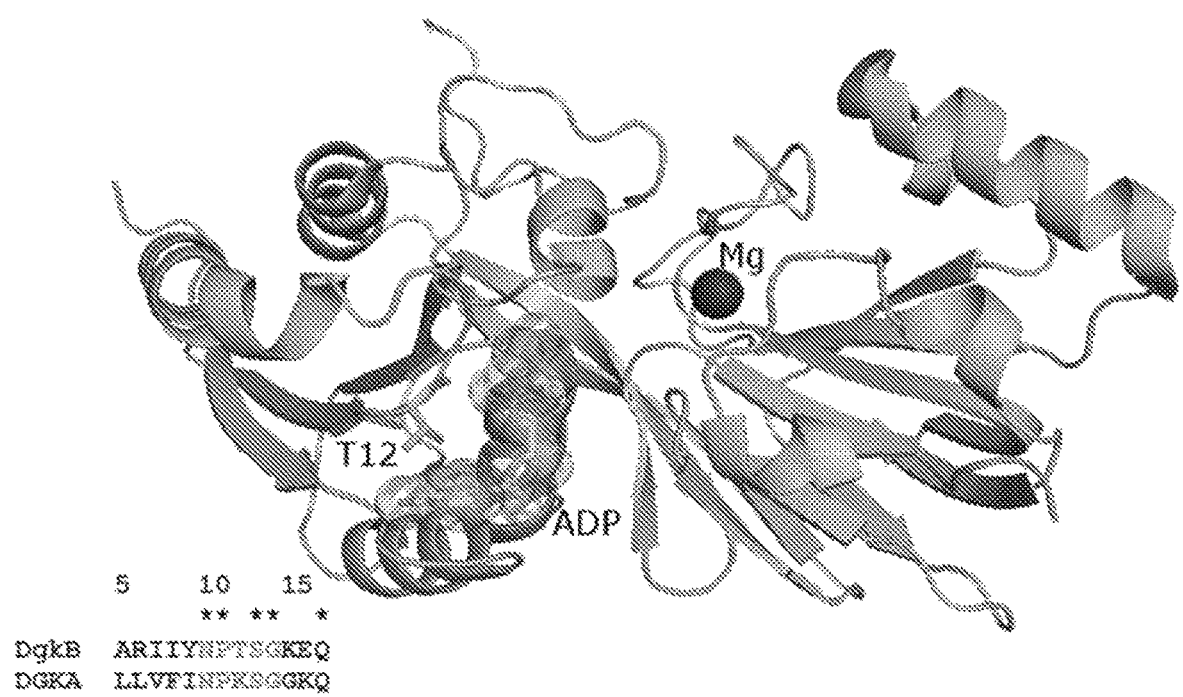

FIG. 11. Related to FIG. 4. Proximity of S. aureus DgkB residue, with homology to DGKα K377, to phosphate groups of ADP. Cartoon Diagram of DgkB monomer (PDB code: 2QV7): α helices are cyan, β sheets and loops are grey, ADP is transparent spheres with a stick model, Mg is blue, the aligned region is green and the homologous residue (threonine 12) is depicted as a green stick model. Partial Structure-Aided Sequence Alignment of S. aureus DgkB and rat DGKα: aligned region is green and ATP acyl phosphate probe-modified DGKα residue is red (K377). Note the threonine residue homologous to the probe-modified lysine of DGKα is in proximity to phosphate groups of ADP. (SEQ ID NOs: 5-6). FIGS. 12A-B. Related to FIG. 7. Chemical proteomic analysis of RF001 activity against recombinant DGKα in HEK293T proteomes. (A) DGKα-HEK293T soluble proteomes were pretreated with RF001 at the indicated concentrations for 30 min prior to labeling with ATP acyl phosphate probe (10 μM, 30 min). After probe labeling, proteomes were subjected to gel-based analyses as described in FIG. 10A. RF001 blocked probe labeling in a concentration-dependent manner and the decrease in fluorescence signals was not due to differences in recombinant protein expression as confirmed by western blot (bottom panel, anti-FLAG, 0.8 μg/mL). Integrated band intensities from these gel-based ATP acyl phosphate assays (B) were used to quantify DGKα inhibition by RF001. Mock-transfected and heat-denatured (95° C. for 2 min) recombinant DGKα lysates were included as additional controls. Data shown are mean+s.e.m. for three biological replicates.  P≤0.01 for mock versus DGKα overexpressed group (0 μM);  P≤0.01 for vehicle-treated (0 μM) versus heat-denatured or inhibitor-treated DGKα overexpressed groups.

Figure 13:
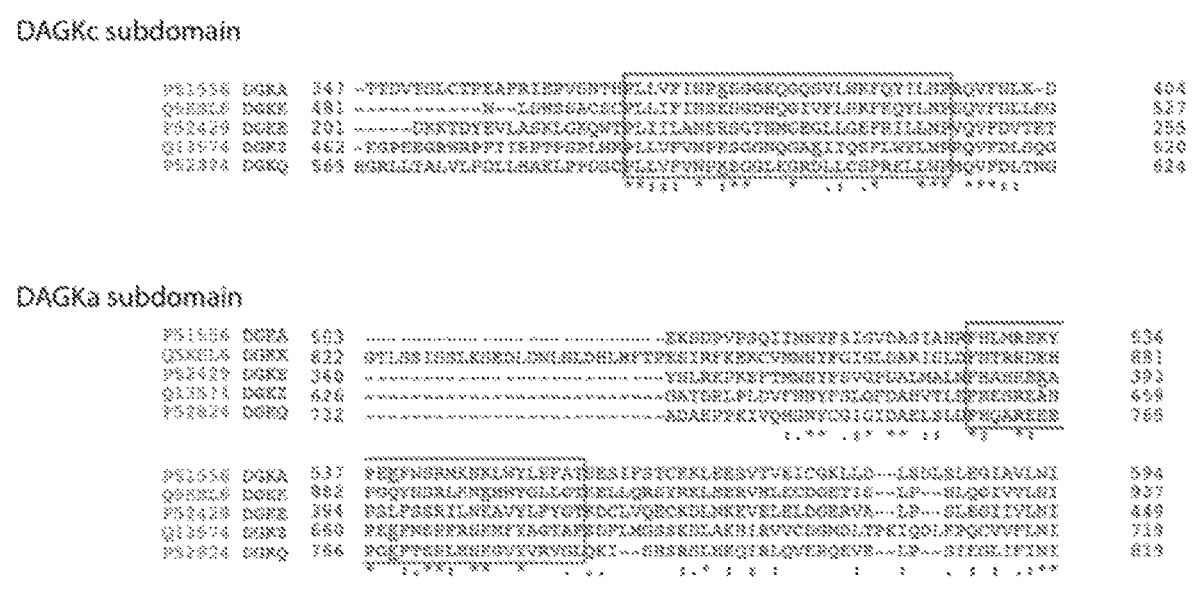

FIG. 13. Related to FIG. 5. Sequence similarity in ATP binding sites of DGK isoforms. Multiple sequence alignment of DGK isoforms were performed with Clustal Omega (Goujon et al., 2010; Sievers et al., 2011) and ATP-sensitive probe-modified peptides found in DAGKc and DAGKa subdomains are shown (highlighted by a red box). Site of probe labeling for ATP acyl phosphate is denoted by a red underline. An asterisk denotes single, fully conserved residue; colon denotes indicates conservation between groups of strongly similar properties; a period signifies conservation between groups of weakly similar properties (Goujon et al., 2010; Sievers et al., 2011). (SEQ ID NOs: 7-16). Table 1 and 1A Related to FIGS. 4-7. SILAC ratios for ATP, Ritanserin, Ketanserin, and RF001 treatment of recombinant DGK-HEK293T soluble lysates. Multiple sequence alignments for sequence logo analysis.

FIGS. 14A-B. Compound and chemical proteomic assays used in cell biology of NSCLC and SCLC cells.

FIGS. 15A-B. Ritanserin, and not Ketanserin, inhibits lung cancer cell survival. A) Lung cancer cell viability as determined through the WST-1 assay. Cells were incubated with compound at the given concentrations for two days and then assayed for metabolic activity. Data are from at least two independent biological replicates and significance values are determined by comparison with Ketanserin treatment of the same concentration. All values were normalized to vehicle treatment. B) Timecourse data for 25 µM (Ketanserin, Ritanserin) or 1 µM (Staurosporine) compound treatment. Cells were plated and mixed with inhibitor on day 0, and assayed for metabolic activity via the WST-1 assay for four subsequent days. Data are from at least two independent biological replicates performed in triplicate, and significance values are given with respect to Ketanserin treatment at the same timepoint. All values were normalized to vehicle treatment. * P≤0.05,  P<0.01, * P≤0.001, and **** P≤0.0001.

Figure 16:
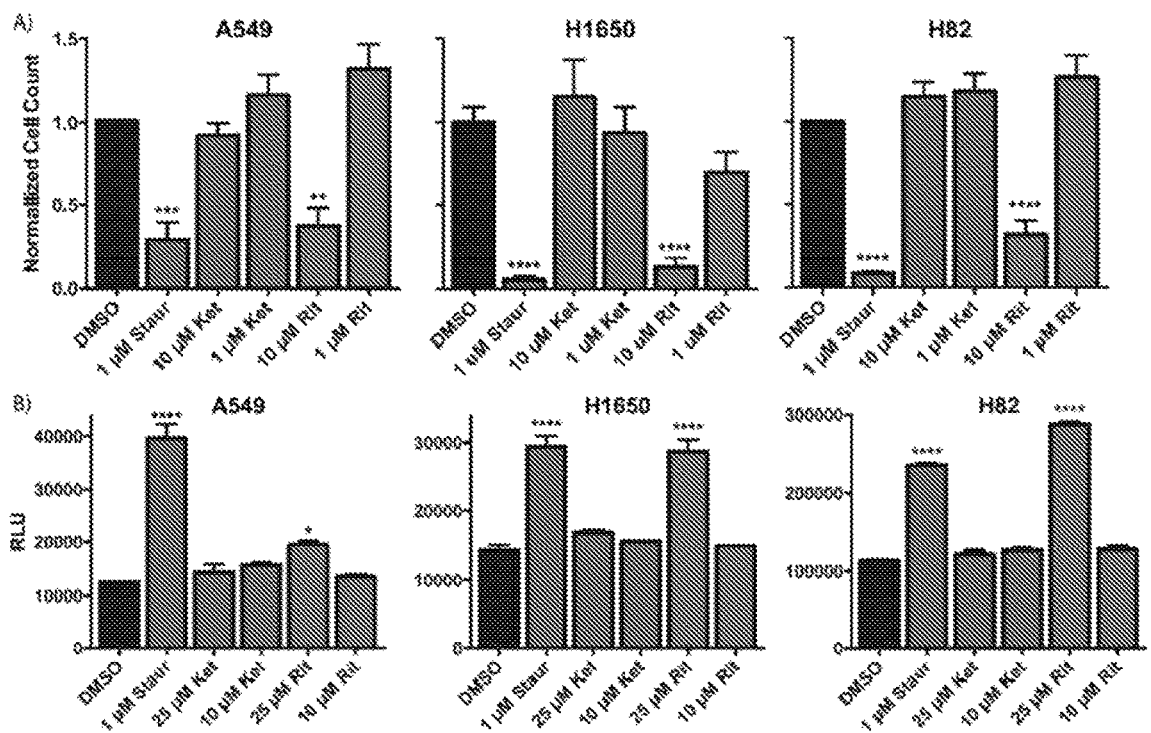

FIGS. 16A-B. Additional measures of cell death. A) Direct counts of cells after 48 hours of compound treatment with either Staurosporin (Staur), Ketanserin (Ket), or Ritanserin (Rit) at the given concentrations. Adherent cells (A549 and H1650) were detached with trypsin and live cells were distinguished through death staining with 10 nM Trypan Blue. All results were normalized to vehicle control (DMSO), which was assigned a value of 1. Significance was calculated by comparison with 10 µM Ketanserin treatment. B) Determination of apoptosis via the CaspaseGlo 3/7 assay. Cells were incubated with the compounds at the concentrations given and allowed to grow for 24 hours, at which point caspase activity was measured. Assays were performed in triplicate and are representative of at least two independent biological replicates. Significance was calculated by comparison with vehicle control. * P≤0.05,  P≤ 0.01, * P≤0.001, and **** P≤0.0001.

Figure 17:
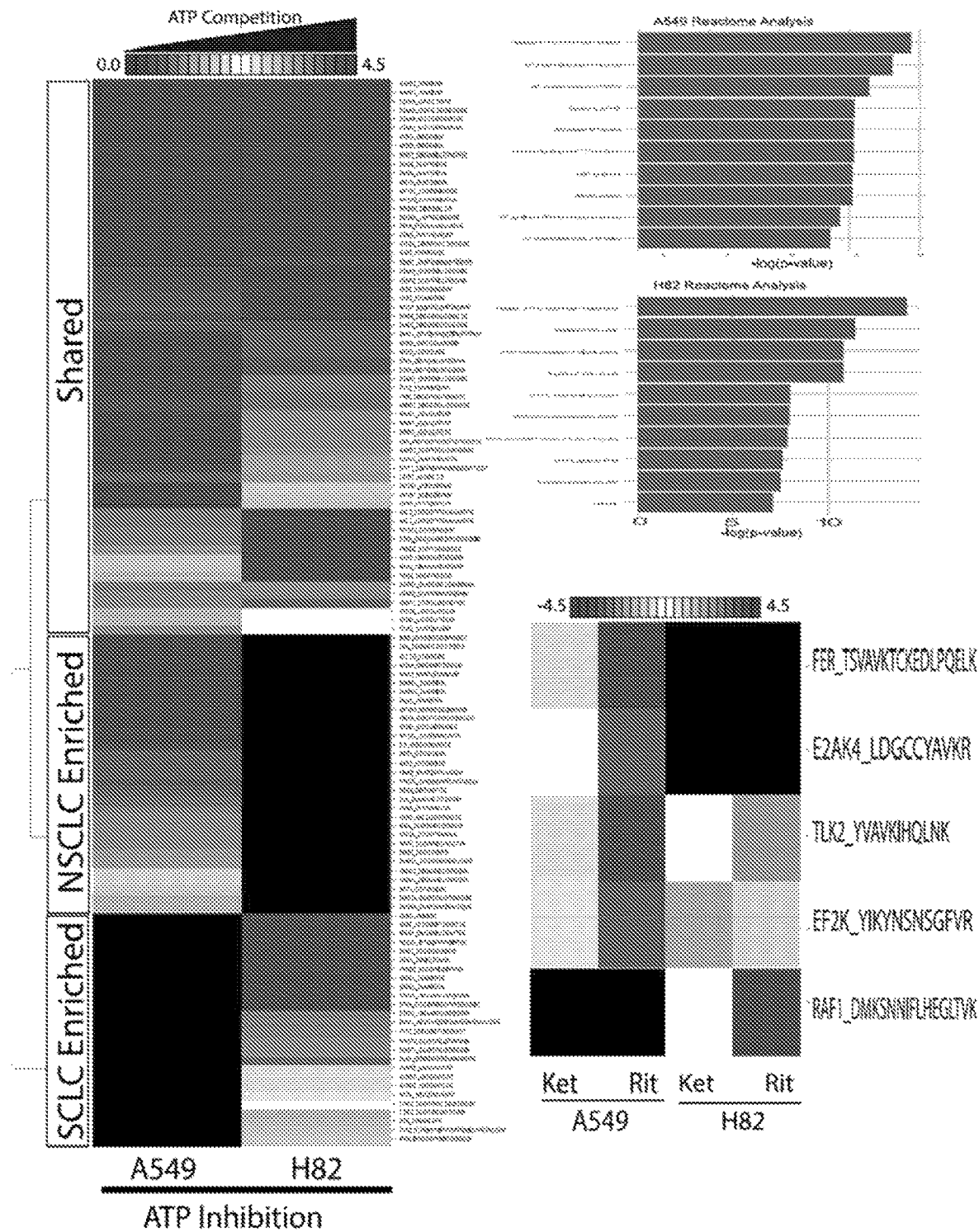

FIG. 17. Kinome target engagement profiles if ritanserin using ATP acyl phosphates.

Figure 18:
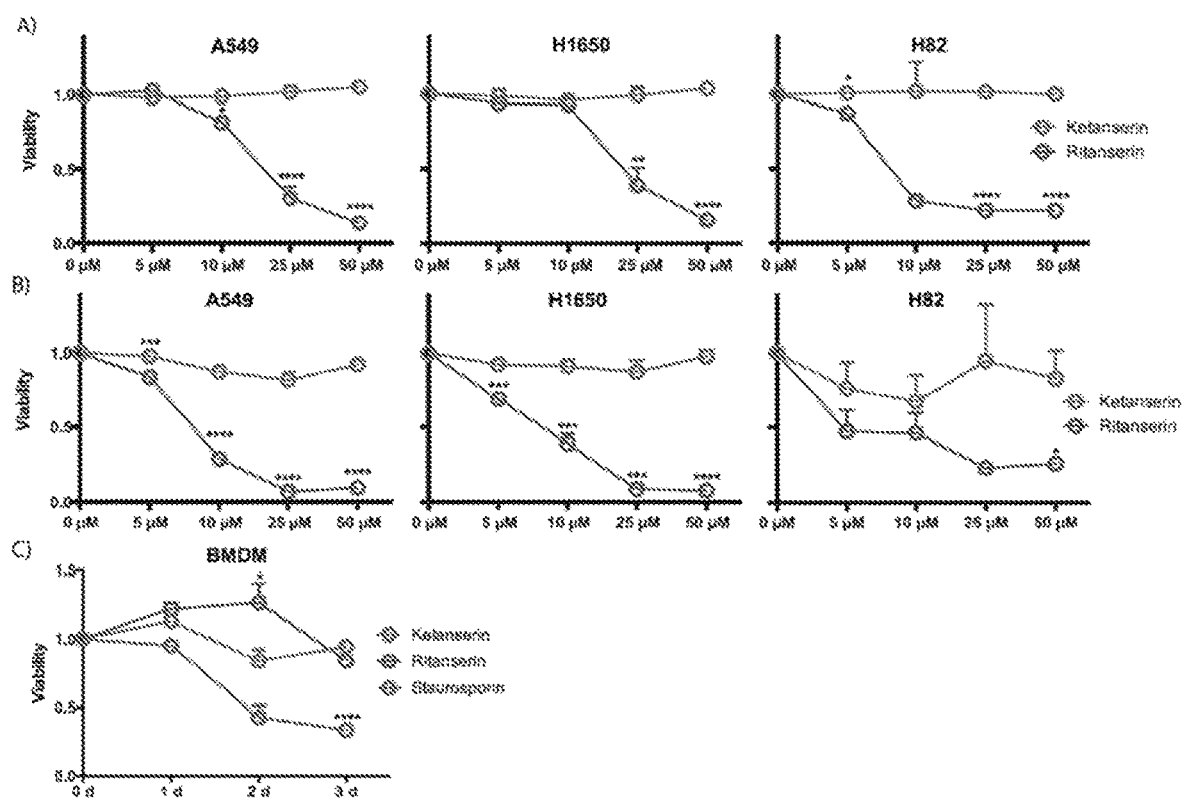

FIGS. 18A-C. Additional time points and cell lines for cell viability study. A and B) Lung cancer cell viability as determined through the WST-1 assay A) 1 day or B) 4 days after addition of compounds. Cells were incubated with compound at the given concentrations for one day and then assayed for metabolic activity. Data are from at least two independent biological replicates performed in triplicate and significance values are determined by comparison with Ketanserin treatment of the same concentration and time point. All values were normalized to vehicle treatment. C) WST-1 Cell Proliferation Assay time course of Bone Marrow Derived Macrophages (BMDMs) treated with either 1 µM Staurosporin, 25 µM Ritanserin, or 25 µM Ketanserin. All values were normalized to vehicle treatment and significance determined with respect to 25 µM Ketanserin treatment at the same timepoint. Data are from two independent biological replicates performed in triplicate. * P≤0.05,  P≤0.01, * P≤0.001, and **** P≤0.0001.

Figure 19:
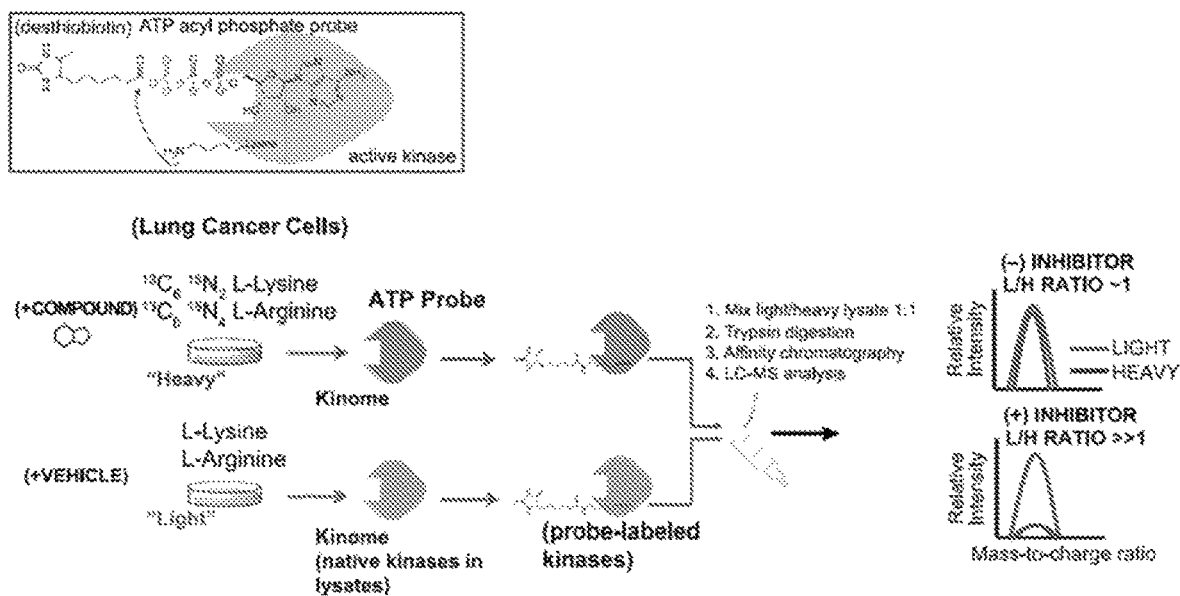

FIG. 19. Quantitative chemical proteomics using SILAC.

FIGS. 20A-I. CRAF response to ritanserin (Rit) and RF001, and CHK2 response to RF001 treatments. A-B) SILAC peaks of CRAF ATP Acyl-phosphate labeling in Heavy samples in vitro treated with 1 mM RF001 or DMSO in (A) H82 Small Cell Lung Cancer Cell and (B) HEK293T cell lysates. C) Ratio of CRAF ATP Acyl-phosphate labeling peptide intensity for heavy labeled compound treated (H) over light labeled DMSO control (L) in H82 and HEK293T cell lines. D-E) SILAC peaks of CRAF ATP Acyl-phosphate labeling in Heavy samples in vitro treated with 100 µM Rit or DMSO in (D) H82 Small Cell Lung Cancer Cell Line and (E) HEK293T cells. F) Ratio of CRAF ATP Acyl-phosphate labeling peptide intensity for heavy labeled compound treated (H) over light labeled DMSO control (L) in H82 and HEK293T cell lines. G-I) SILAC peaks of CHK2 ATP Acyl-phosphate labeling in Heavy samples in vitro treated with 1 mM RF001 or DMSO in (G) H82 and (H) HEK293T cells. I) Ratio of CHK2 ATP Acyl-phosphate labeling peptide intensity for heavy labeled compound treated (H) over light labeled DMSO control (L) in H82 and HEK293T cell lines.

DESCRIPTION

Diacylglycerol kinases (DGKs) are components of signal transduction cascades that regulate cell biology through ATP-dependent phosphorylation of the lipid messenger diacylglycerol. Methods for direct evaluation of DGK activity in native biological systems are lacking and needed to study isoform-specific functions of these multidomain lipid kinases. Here, ATP acyl phosphate activity-based probes and quantitative mass spectrometry were used to define, for the first time, ATP- and small molecule-binding motifs of representative members from all five DGK subtypes. Chemical proteomics was used to discover an unusual binding mode for the DGK-alpha (DGKα) inhibitor ritanserin, including interactions at the atypical C1 domain distinct from the ATP binding region. Unexpectedly, deconstruction of ritanserin yielded a fragment compound that blocks DGKα activity through a conserved binding mode and enhanced selectivity against the kinome. Collectively, the studies illustrate the power of chemical proteomics to profile protein-small molecule interactions of lipid kinases for fragment-based lead discovery.

The disclosure relates to compounds of the formula (Ia):

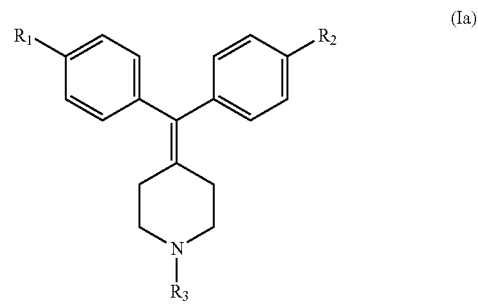

or a pharmaceutically acceptable salt, polymorph, prodrug, or solvate thereof;

wherein:

$R^1$ and $R^2$, independently, are F, Cl, Br, $CH_3$, $CF_3$, $OCF_3$, $OCH_3$, $CH_2F$, $NH_2$, $NHSO_2CH_2CH_2CH_3$, $CONHCH_3$, $C(CH_3)_3$, $NHCH(CH_3)_2$, $CH_2OH$, COCHIN, COOH, or OH;

$R^3$ is F, Cl, Br, $CH_3$, $CF_3$, $OCF_3$, $OCH_3$, $CH_2F$, $NH_2$, $NHSO_2CH_2CH_2CH_3$, $CONHCH_3$, $C(CH_3)_3$, $NHCH(CH_3)_2$, $CH_2OH$, $COC_5H_{11}N$, COOH, OH,

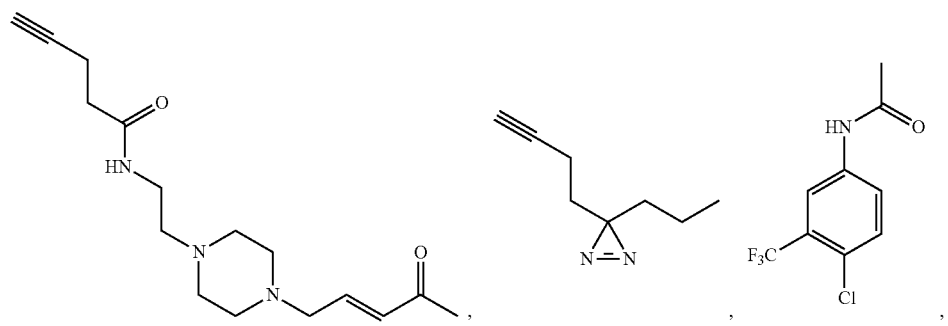
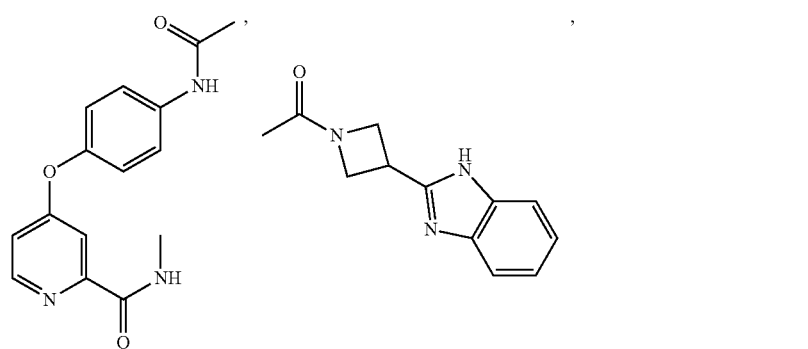
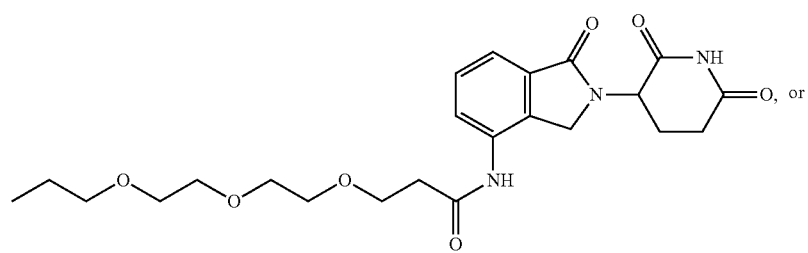
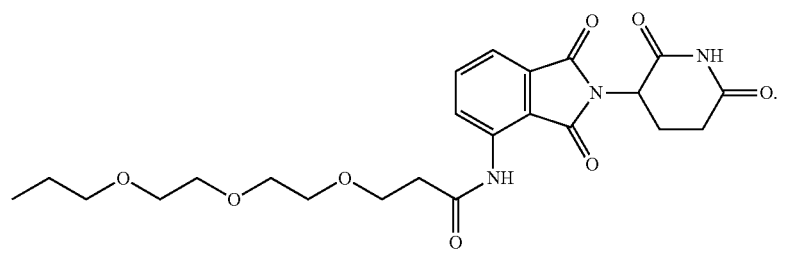

In one embodiment, the compound is any one or a combination of:
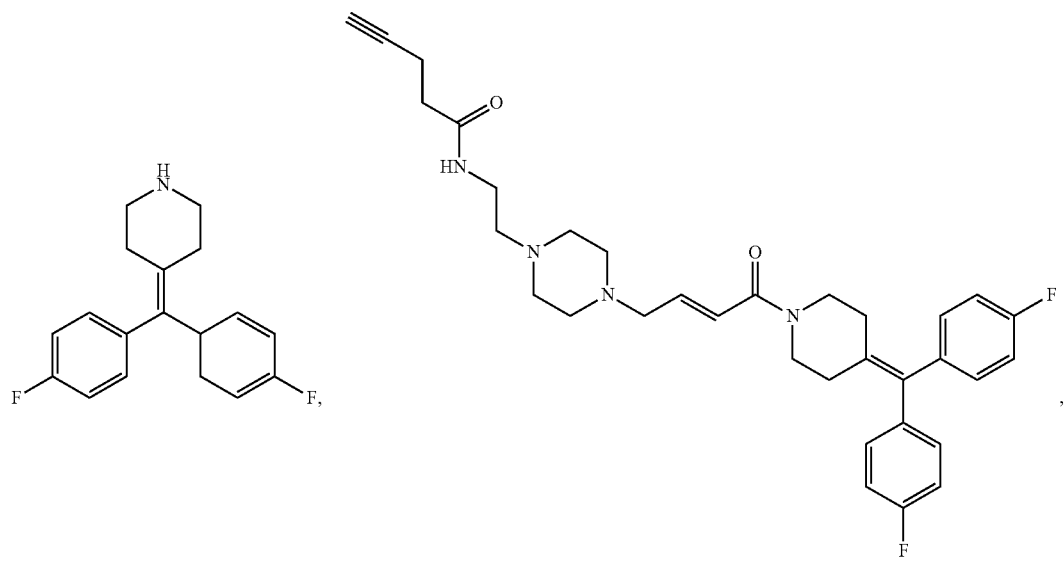
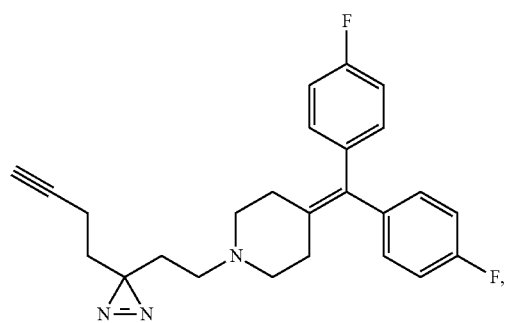
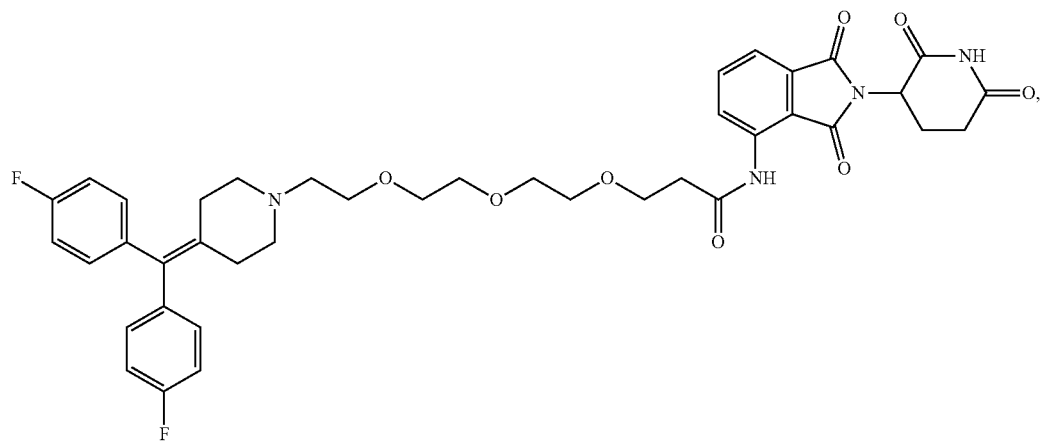

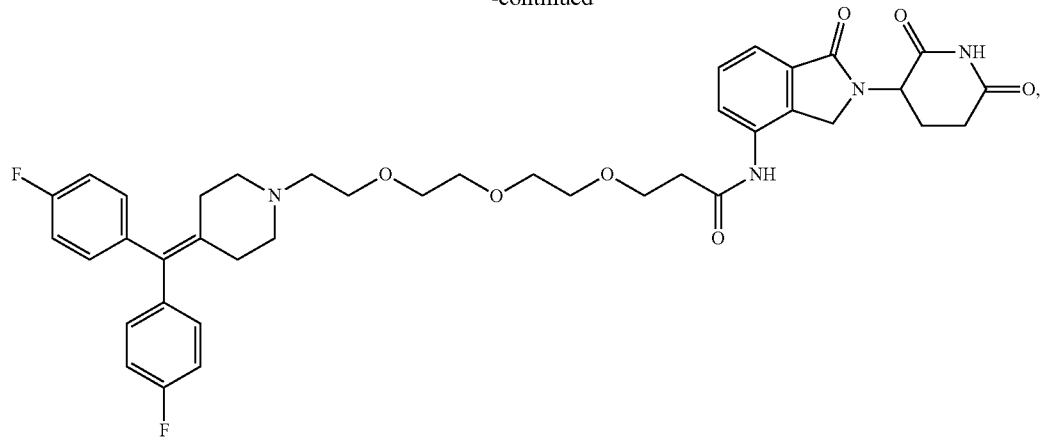
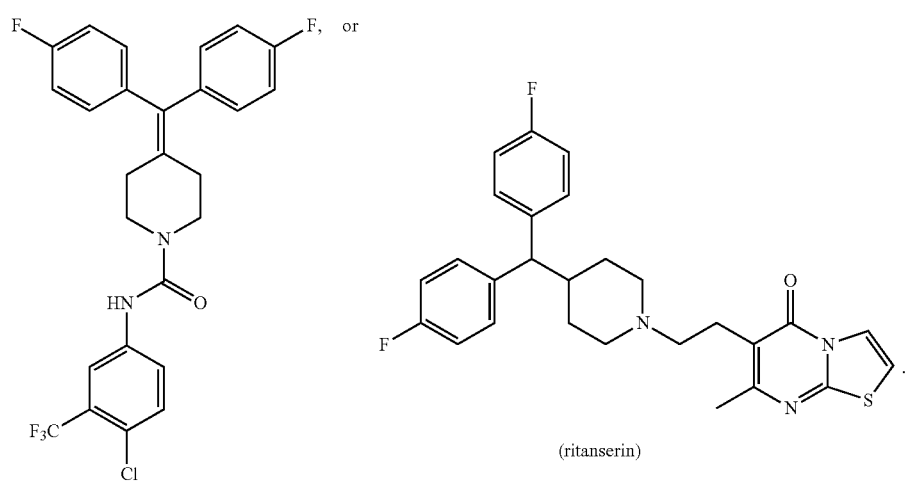 [SMILES: O=C(Nc1ccc(Cl)c(C(F)(F)F)c1)N1CCC(=C(c2ccc(F)cc2)c2ccc(F)cc2)CC1 ; Cc1nc2sccn2c(=O)c1CCN1CCC(C(c2ccc(F)cc2)c2ccc(F)cc2)CC1]
In some embodiments, the compound is not ritanserin.
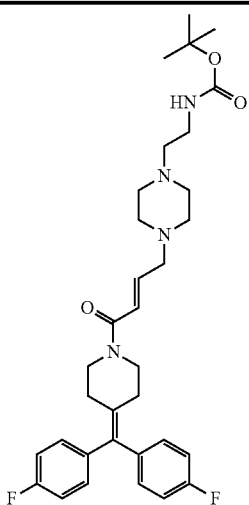
JWB002    580.72

-continued
| | |
|---|---|
| JWB003 560.69 | 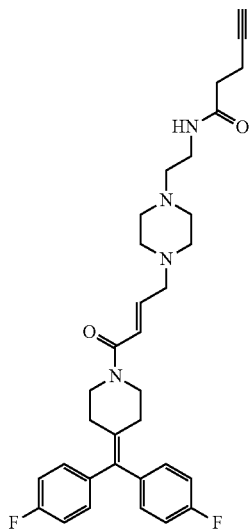 [SMILES: C#CCCC(=O)NCCN1CCN(C/C=C/C(=O)N2CCC(=C(c3ccc(F)cc3)c3ccc(F)cc3)CC2)CC1] |
| JWB006 405.59 | 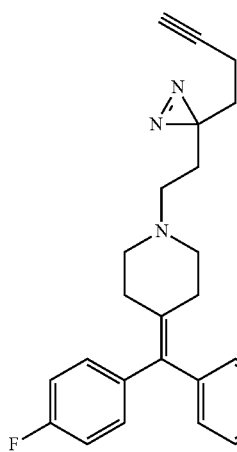 |
| JWB007 744.30 | 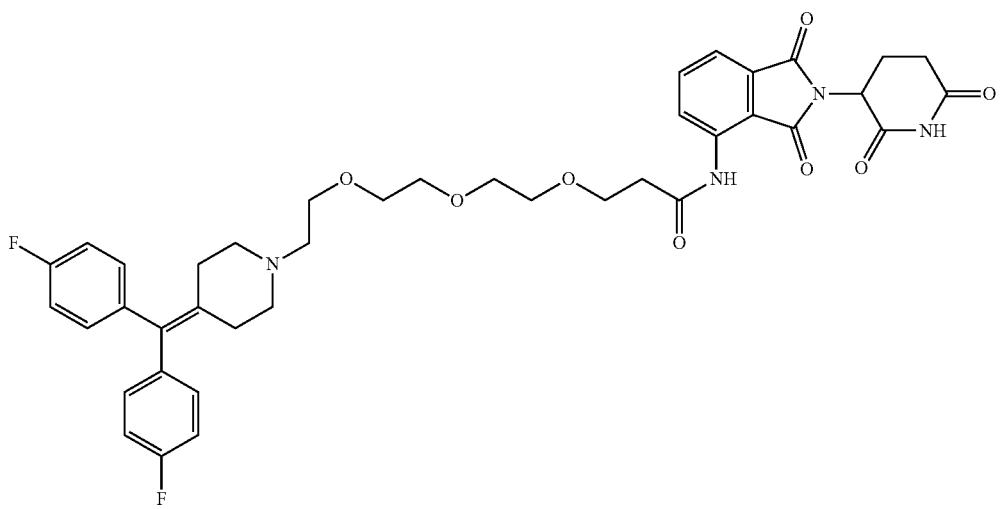 [SMILES: O=C1CCC(N2C(=O)c3cccc(NC(=O)CCOCCOCCOCCN4CCC(=C(c5ccc(F)cc5)c5ccc(F)cc5)CC4)c3C2=O)C(=O)N1] |

JWB010  730.81
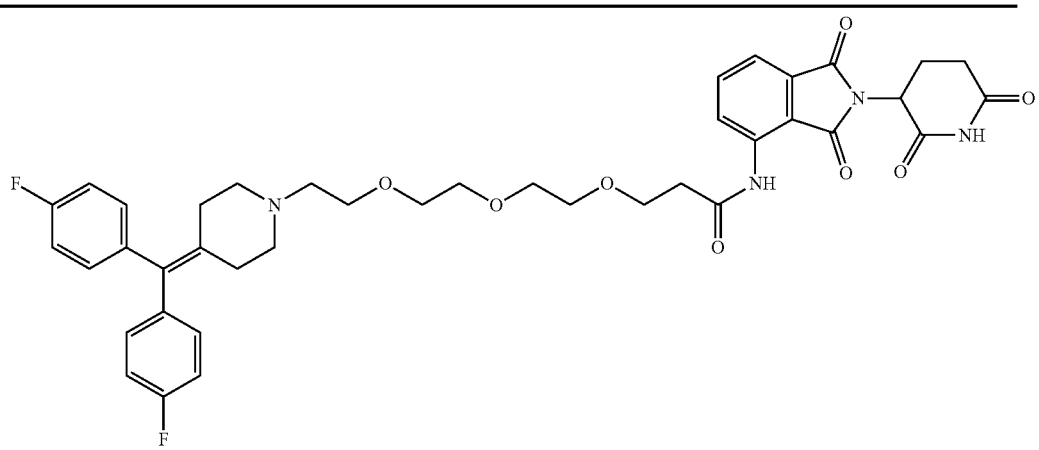
JW6013  653.73
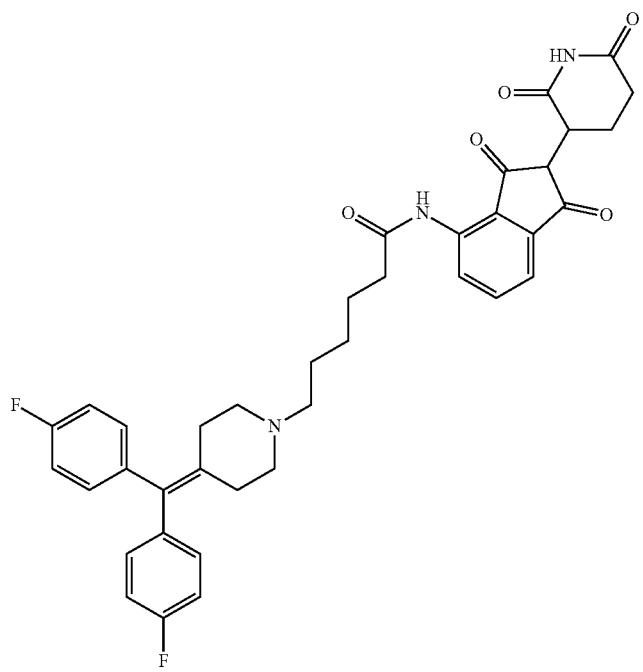 [SMILES: O=C1CCC(C2C(=O)c3cccc(NC(=O)CCCCCN4CCC(=C(c5ccc(F)cc5)c5ccc(F)cc5)CC4)c3C2=O)C(=O)N1]
JW6014  443.51
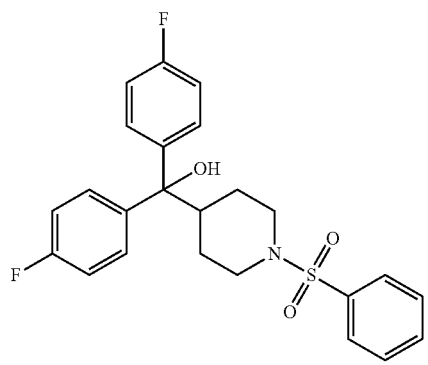 [SMILES: O=S(=O)(c1ccccc1)N1CCC(C(O)(c2ccc(F)cc2)c2ccc(F)cc2)CC1]

-continued
JW6015  656.73
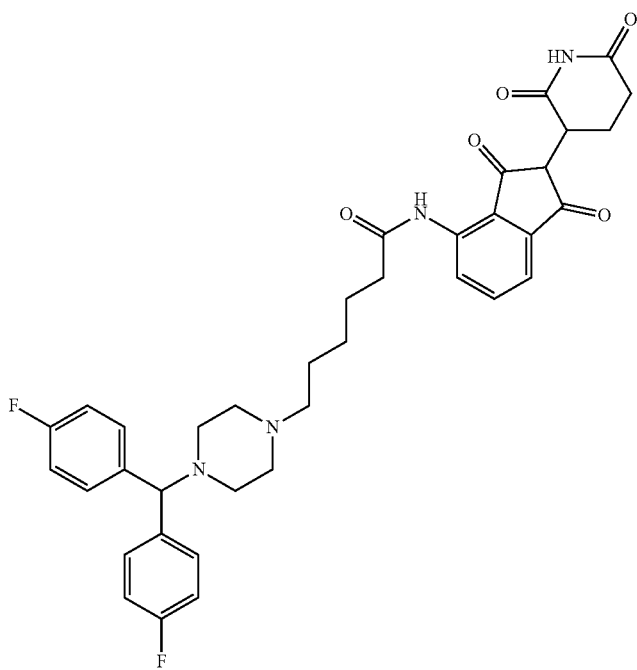 [SMILES: O=C1CCC(C2C(=O)c3cccc(NC(=O)CCCCCN4CCN(C(c5ccc(F)cc5)c5ccc(F)cc5)CC4)c3C2=O)C(=O)N1]
JWB018  432.308
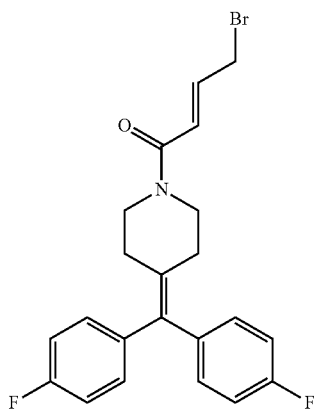 [SMILES: O=C(/C=C/CBr)N1CCC(=C(c2ccc(F)cc2)c2ccc(F)cc2)CC1]
JWB020  406.476
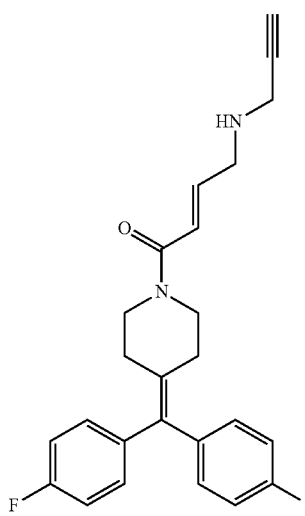

The disclosure also relates to compounds of (I)—(V):

(I)
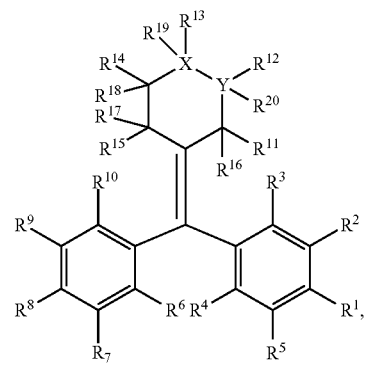

(II)
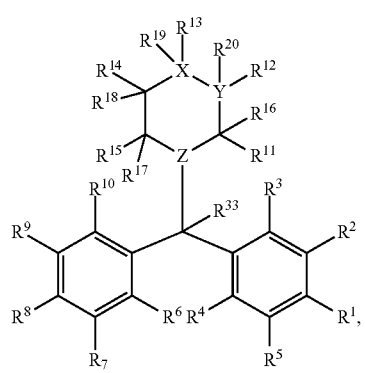

(III)
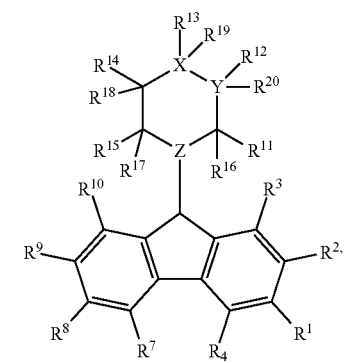

(IV)
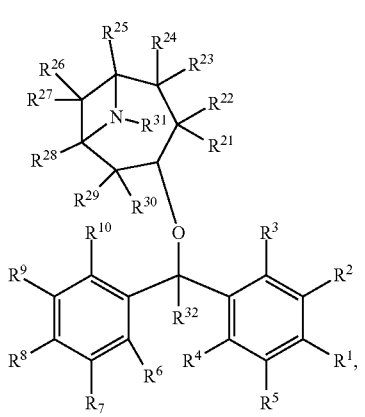

(V)
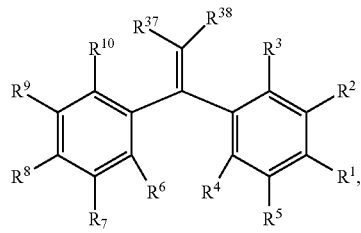

or a pharmaceutically acceptable salt, polymorph, prodrug, or solvate thereof;

wherein;

X is selected from the group consisting of: —$CR^{19}R^{13}$—, —$NR^{35}$—;

Y is selected from the group consisting of: —$CR^{12}R^{20}$—, —$NR^{36}$—;

and X is selected from the group consisting of:

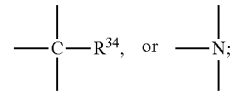

$R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{22}$, $R^{23}$, $R^{24}$, $R^{25}$, $R^{26}$, $R^{27}$, $R^{28}$, $R^{29}$, $R^{30}$, $R^{31}$, $R^{32}$, $R^{33}$, $R^{34}$, $R^{35}$, $R^{36}$, $R^{37}$, and $R^{38}$, independently, are selected from the group consisting of —H, —F, —Cl, —Br and substituted or unsubstituted ($C_1$-$C_{100}$) hydrocarbyl.

In one embodiment, $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{22}$, $R^{23}$, $R^{24}$, $R^{25}$, $R^{26}$, $R^{27}$, $R^{28}$, $R^{29}$, $R^{30}$, $R^{31}$, $R^{32}$, $R^{33}$ and $R^{34}$, independently, are selected from the group consisting of: substituted or unsubstituted ($C_1$-$C_{100}$)alkyl, ($C_1$-$C_{100}$)alkenyl, ($C_1$-$C_{100}$)alkynyl, ($C_1$-$C_{100}$)acyl, ($C_3$-$C_{20}$) cycloalkyl, ($C_1$-$C_{20}$)aryl, ($C_1$-$C_{20}$)aralkyl, ($C_1$-$C_{100}$) alkoxy, an amine, or ($C_1$-$C_{100}$)haloalkyl.

In another embodiment, $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{22}$, $R^{23}$, $R^{24}$, $R^{25}$, $R^{26}$, $R^{27}$, $R^{28}$, $R^{29}$, $R^{30}$, $R^{31}$, $R^{32}$, $R^{33}$ and $R^{34}$, independently, are selected from the group consisting of: substituted or unsubstituted ($C_1$-$C_{40}$)alkyl, ($C_1$-$C_{40}$)alkenyl, ($C_1$-$C_{40}$)alkynyl, ($C_1$-$C_{40}$)acyl, ($C_3$-$C_{10}$) cycloalkyl, ($C_1$-$C_{10}$)aryl, ($C_1$-$C_{10}$)aralkyl, ($C_1$-$C_{40}$)alkoxy, an amine, or ($C_1$-$C_{40}$)haloalkyl.

In embodiment, $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{22}$, $R^{23}$, $R^{24}$, $R^{25}$, $R^{26}$, $R^{27}$, $R^{28}$, $R^{29}$, $R^{30}$, $R^{31}$, $R^{32}$, $R^{33}$ and $R^{34}$, independently, are selected from the group consisting of: —F, —Cl, —Br, —$CH_3$, —$CF_3$, —$OCF_3$, —$OCH_3$, —$CH_2F$, —$NH_2$, —$NHSO_2CH_2CH_2CH_3$, —$CONHCH_3$, —$C(CH_3)_3$, —$NHCH(CH_3)_2$, —$CH_2OH$, —COCHIN, —COOH, —OH,

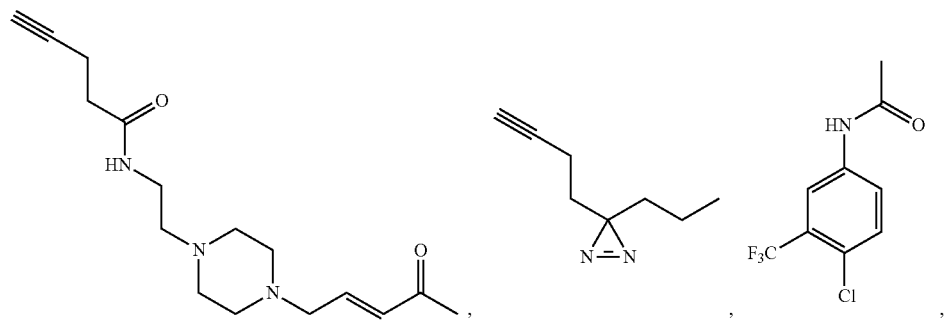
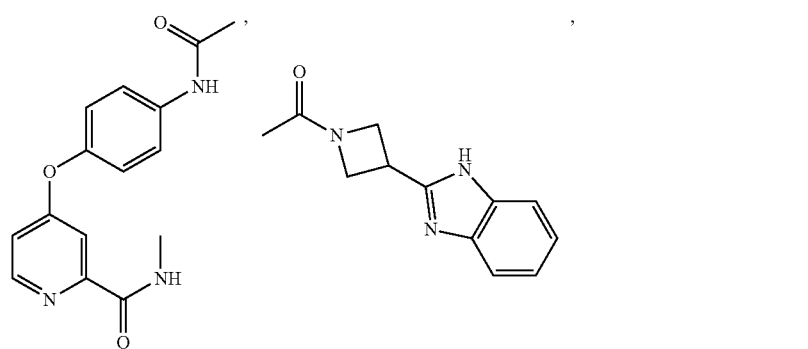
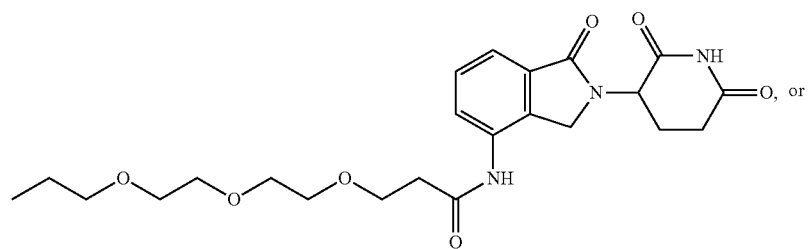
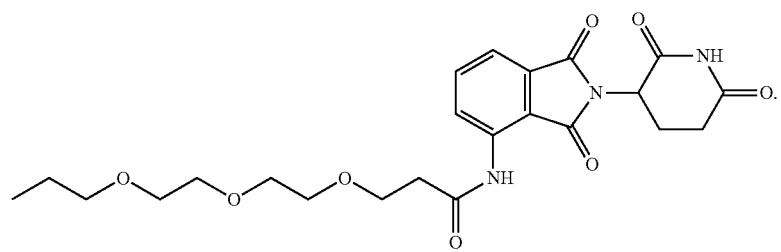

In another embodiment, the structure according to formula (I) is selected from the group consisting of:
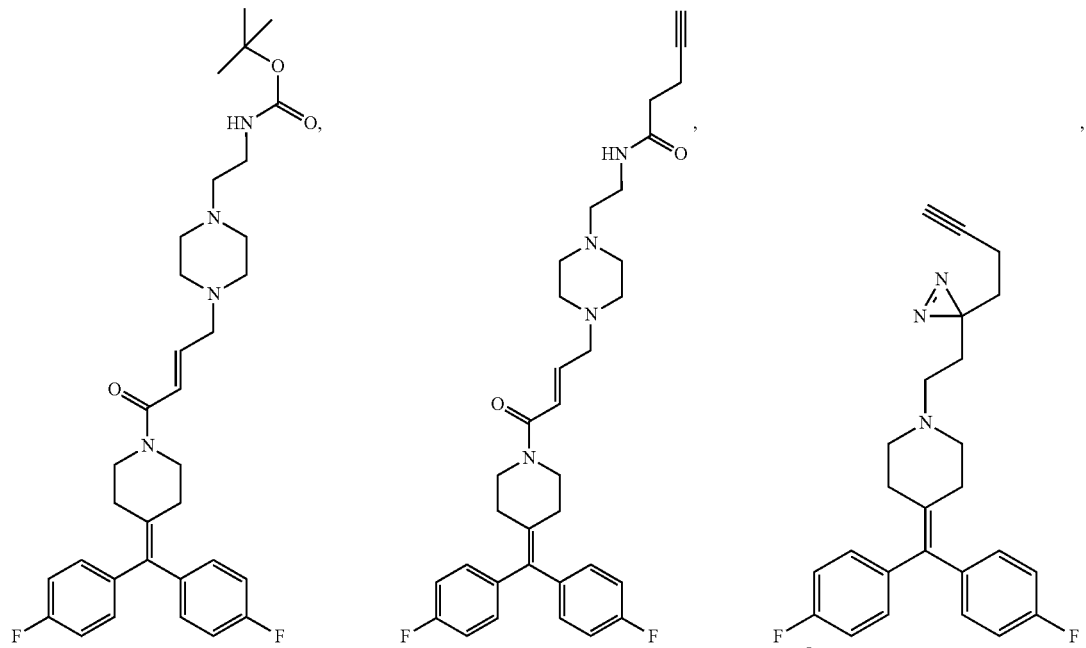
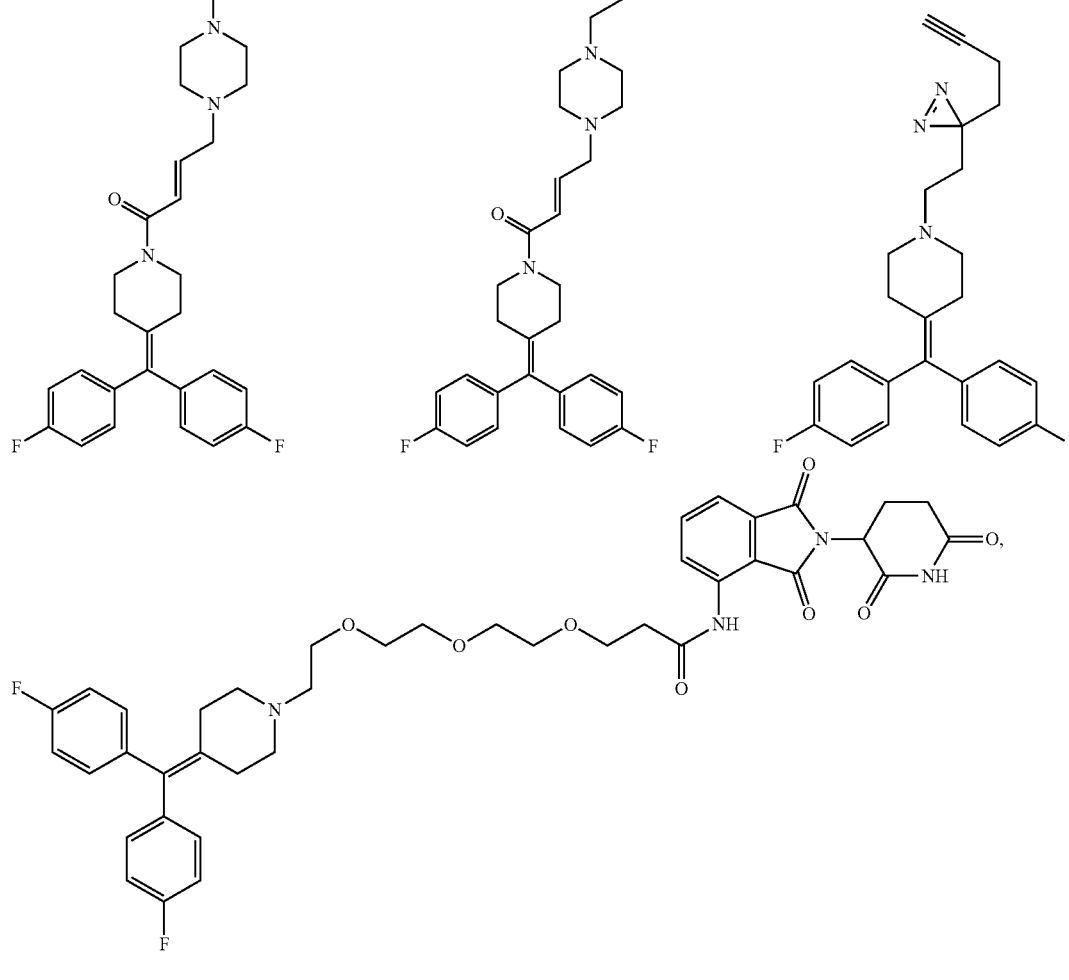
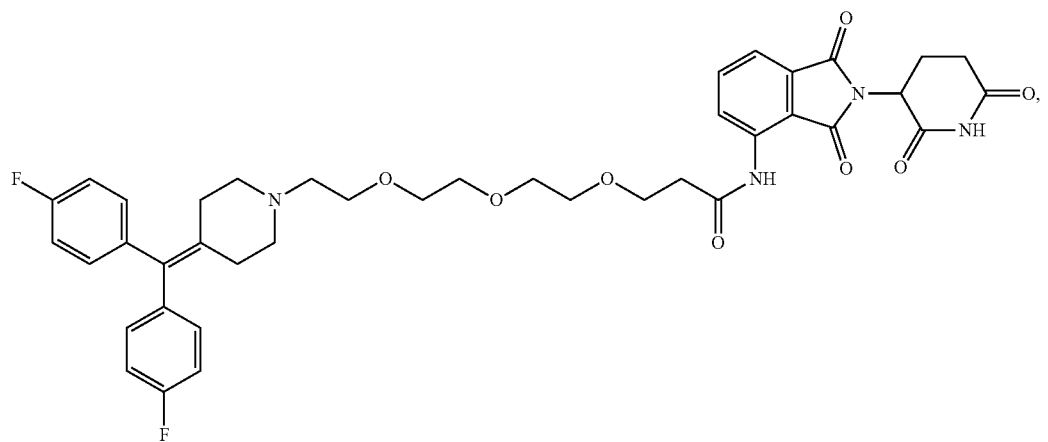

-continued
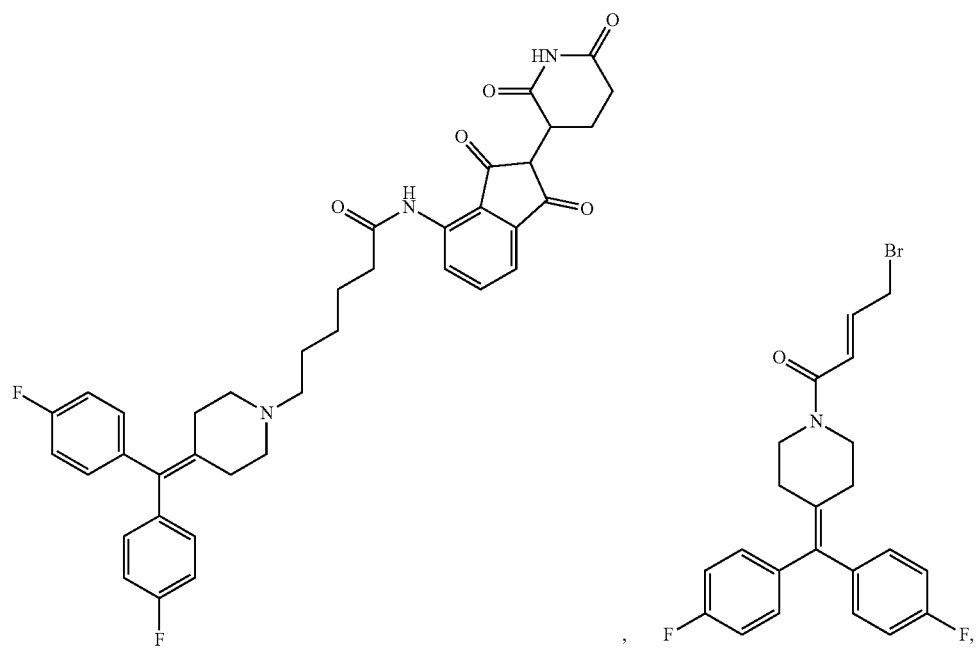
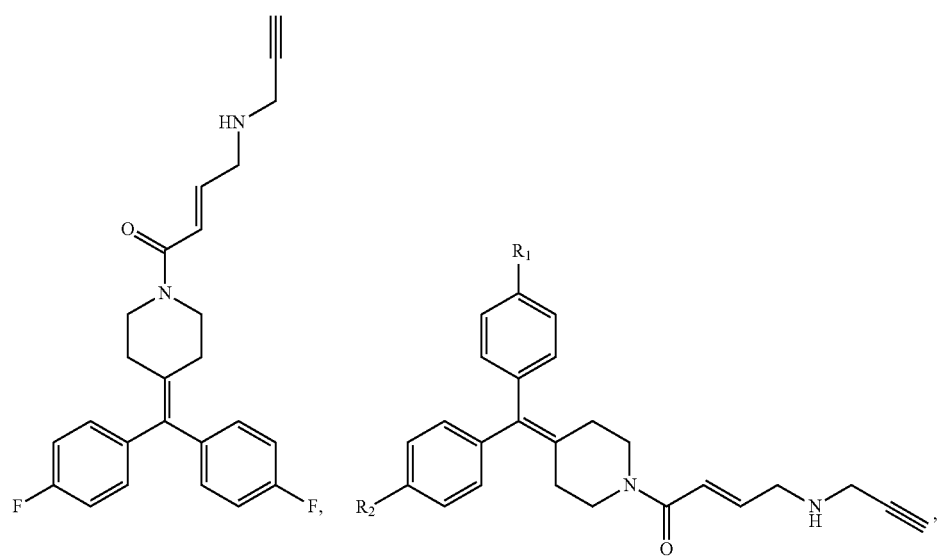
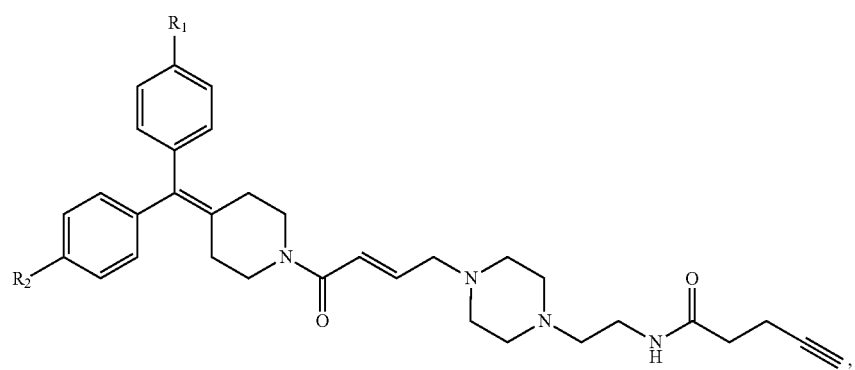

-continued
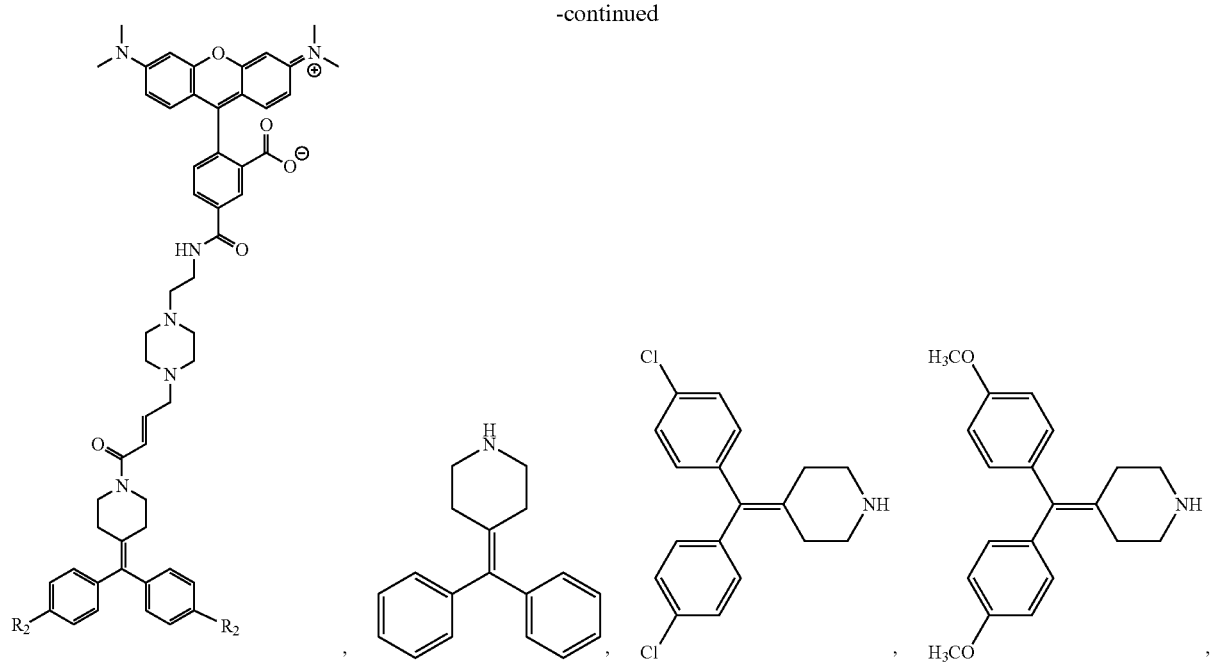
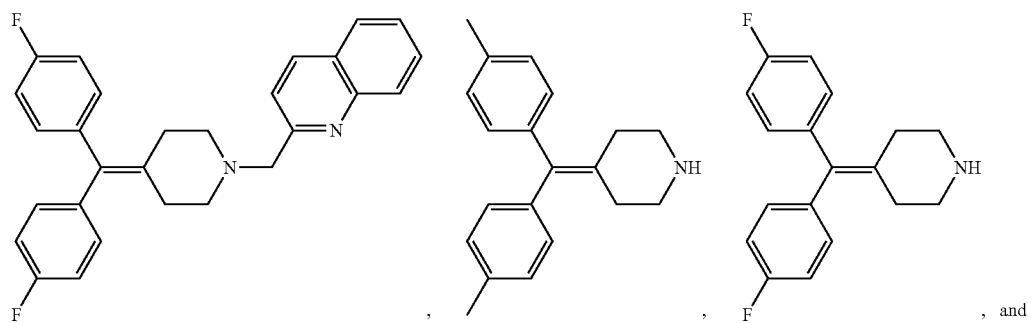
, and
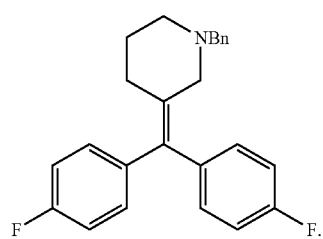
.

The disclosure also relates to compounds:

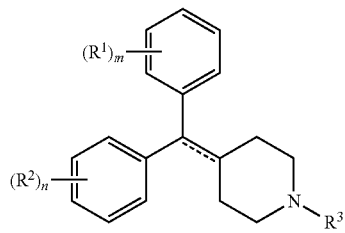

Formula I each R[1] is independently H, halogen, —CN, —NH$_2$, —NH(alkyl), —N(alkyl)$_2$, —OH, —C(=O)OH, —C(=O)O(alkyl), —C(=O)NH$_2$, —C(=O)NH(alkyl), —C(=O)N(alkyl)$_2$, —S(=O)$_2$NH$_2$, —S(=O)$_2$NH(alkyl), —S(=O)$_2$N(alkyl)$_2$, —CF$_3$, alkyl which is optionally substituted, alkoxy which is optionally substituted each R[2] is independently H, halogen, —CN, —NH$_2$, —NH(alkyl), —N(alkyl)$_2$, —OH, —C(=O)OH, —C(=O)O(alkyl), —C(=O)NH$_2$, —C(=O)NH(alkyl), —C(=O)N(alkyl)$_2$, —S(=O)$_2$NH$_2$, —S(=O)$_2$NH(alkyl), —S(=O)$_2$N(alkyl)$_2$, —CF$_3$, alkyl which is optionally substituted, alkoxy which is optionally substituted m is 1,2,3,4, or 5
n is 1,2,3,4, or 5
R[3] is selected from

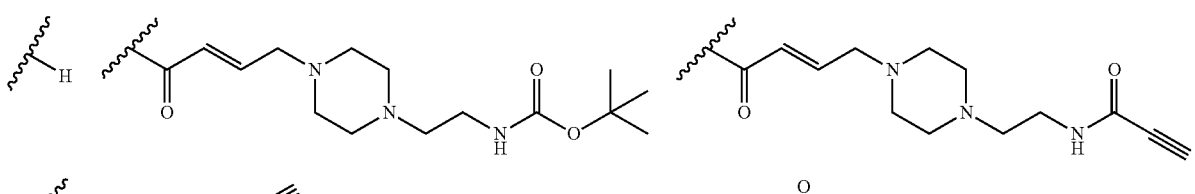

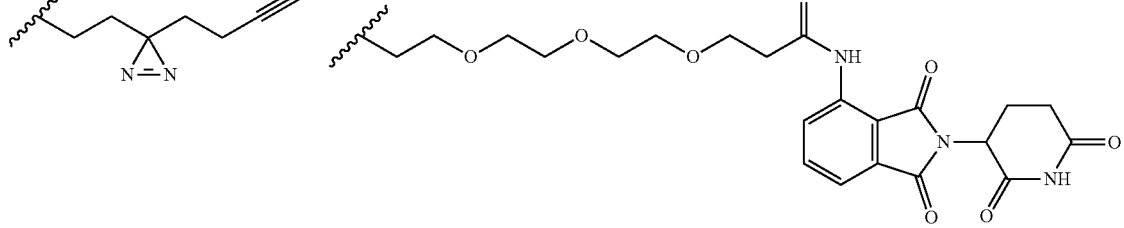

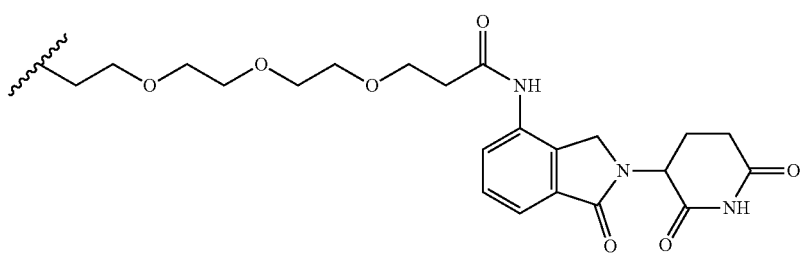

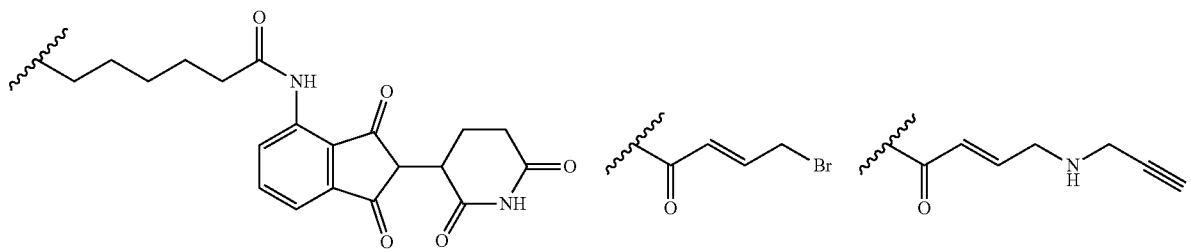

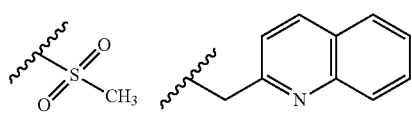

-continued

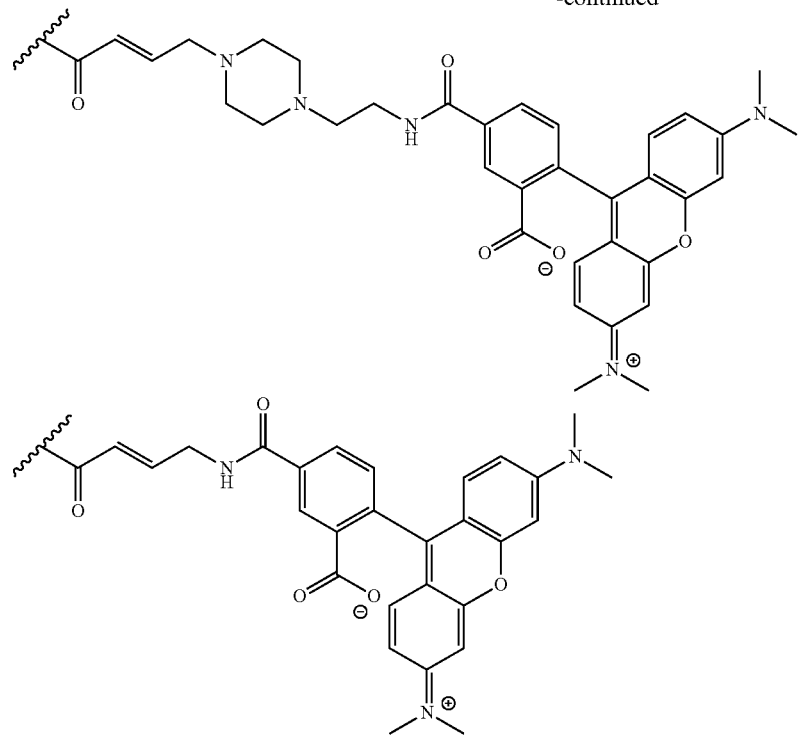

each R⁴ is independently H, halogen, —CN, —NH₂, —NH(alkyl), —N(alkyl)₂, —OH, —C(=O)OH, —C(=O)O(alkyl), —C(=O)NH₂, —C(=O)NH(alkyl), —C(=O)\(alkyl)₂, —S(=O)₂NH₂, —S(=O)₂NH(alkyl), —S(=O)₂N(alkyl)₂, —CF₃, alkyl which is optionally substituted, alkoxy which is optionally substituted . . .

each R⁵ is independently H, halogen, —CN, —NH₂, —NH(alkyl), —N(alkyl)₂, —OH, —C(=O)OH, —C(=O)O(alkyl), —C(=O)NH₂, —C(=O)NH(alkyl), —C(=OWN(alkyl)₂, —S(=O)₂NH₂, —S(=O)₂NH(alkyl). —S(=O)₂N(alkyl)₂, —CF₃, alkyl which is optionally substituted, alkoxy which is optionally substituted o is 1,2,3,4, or 5
p is 1,2,3,4, or 5 . . .
R⁶ is selected from each R⁷ is independently H, halogen, —CN, —NH₂, —NH(alkyl), —N(alkyl)₂, —OH, —C(=O)OH, —C(=O)O(alkyl), —C(=O)NH₂, —C(=O)NH(alkyl), —C(=O)N(alkyl)₂, —S(=O)₂NH₂, —S(=O)₂NH(alkyl), —S(=O)₂N(alkyl)₂, —CF₃, alkyl which is optionally substituted, alkoxy which is optionally substituted each R⁸ is independently H, halogen, —CN, —NH₂, —NH(alkyl), —N(alkyl)₂, —OH, —C(=O)OH, —C(=O)O(alkyl), —C(=O)NH₂, —C(=O)NH(alkyl), —C(=O)N(alkyl), —S(=O)₂NH₂, —S(=O)₂NH(alkyl), —S(=O)₂N(alkyl)₂, —CF₃, alkyl which is optionally substituted, alkoxy which is optionally substituted q is 1,2,3,4, or 5
r is 1,2,3,4, or 5
R⁹ is selected from

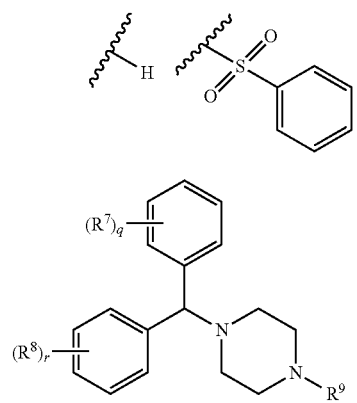

Formula III

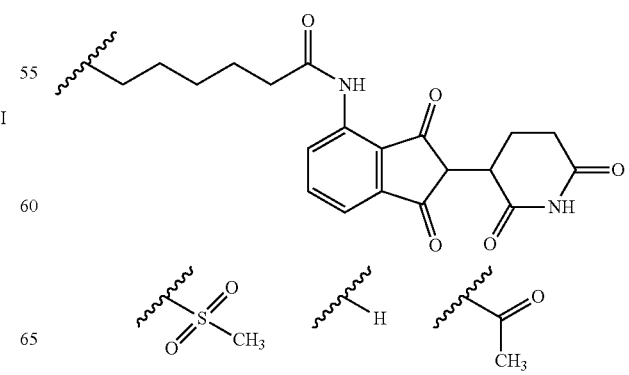

-continued

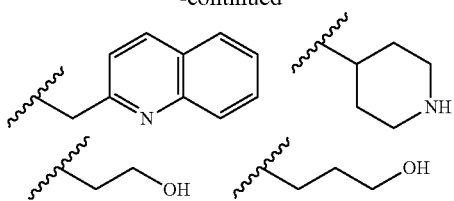

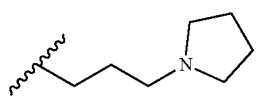

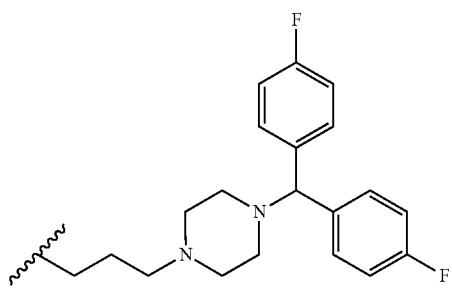

Consolidated Formula

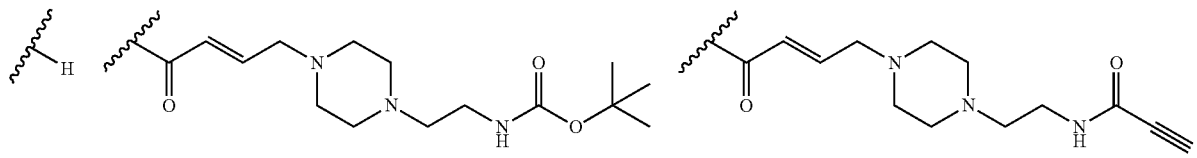

each R¹ is independently H, halogen, —CN, —NH₂, —NH(alkyl), —N(alkyl)₂, —OH, —C(=O)OH, —C(=O)O(alkyl), —C(=O)NH₂, —C(=O)NH(alkyl), —C(=O)N(alkyl)₂, —S(=O)₂NH₂, —S(=O)₂NH(alkyl), —S(=O)₂N(alkyl)₂. —CF₃, alkyl which is optionally substituted, alkoxy which is optionally substituted each R² is independently H, halogen, —CN, —NH₂, —NH(alkyl), —N(alkyl)₂, —OH, —C(=O)OH, —C(=O)O(alkyl), —C(=O)NH₂, —C(=O)NH(alkyl), —C(=O)N(alkyl)₂, —S(=O)₂NH₂, —S(=O)₂NH(alkyl), —S(=O)₂N(alkyl)₂, —CF₃, alkyl which is optionally substituted, alkoxy which is optionally substituted m is 1,2,3,4, or 5
n is 1,2,3,4, or 5
A is selected from C, CH, or N
B is selected from C, CH, or C(OH),
R³ is selected from

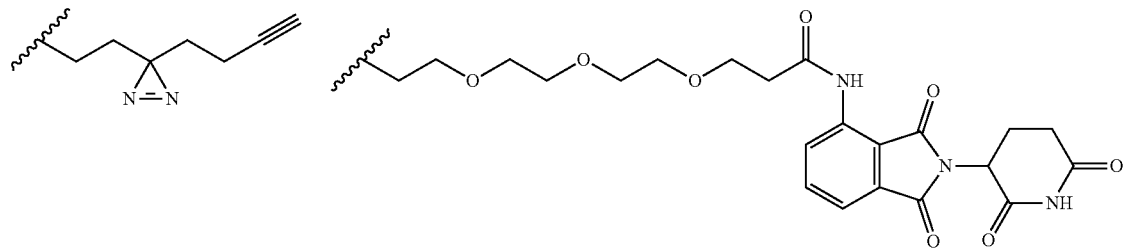

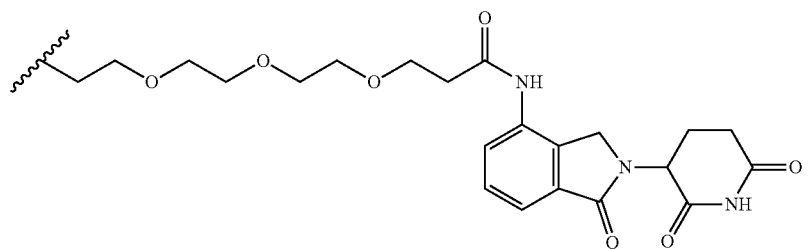

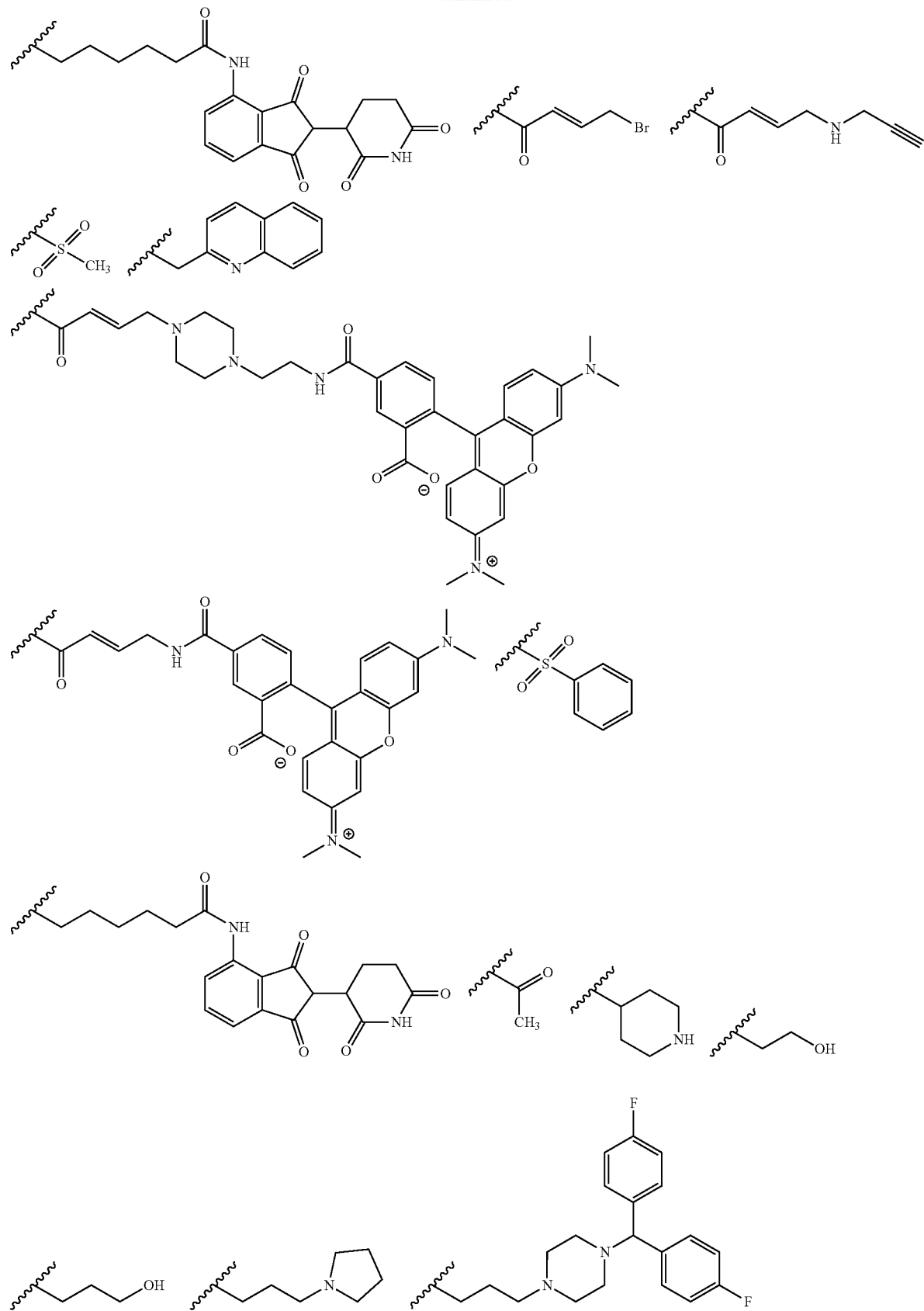

Miscellaneous 4 Compounds
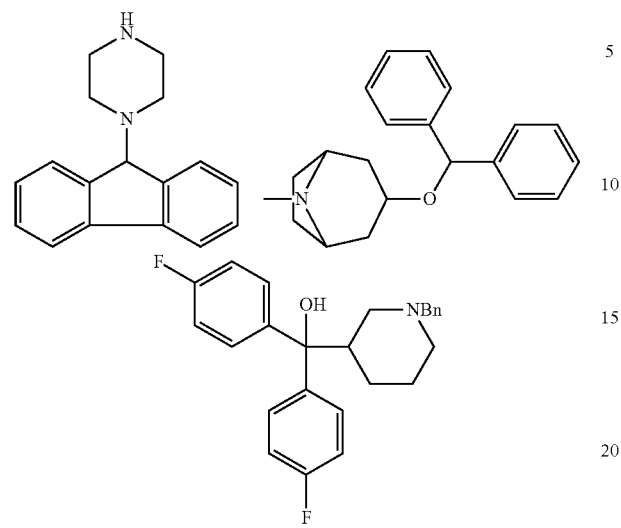
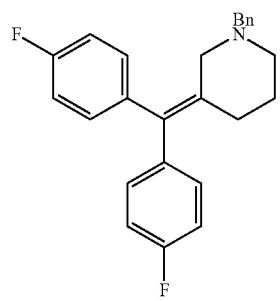
| Zeta Name | Structure | 1 mM % Activity | Reference sheet | 100 uM % Activity | Reference sheet | Molecular Mass |
|---|---|---|---|---|---|---|
| TH002 | 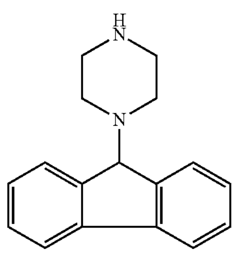 [SMILES: c1ccc2c(c1)-c1ccccc1C2N1CCNCC1] | 0 | 180419 | 98 | 180419 | 250.20 |
| TH003 | 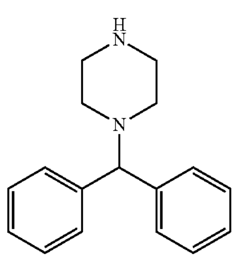 [SMILES: c1ccc(C(c2ccccc2)N2CCNCC2)cc1] | 0 | 180419 | 99 | 180419 | 252.20 |
| TH004 | 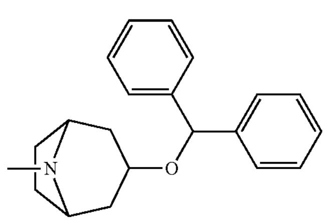 [SMILES: CN1C2CCC1CC(OC(c1ccccc1)c1ccccc1)C2] | 21 | 180419 | 82 | 180419 | 307.20 |

| | | | | | | |
|---|---|---|---|---|---|---|
| TH005 | (structure) | | 0 | 180419 | 86 | 180419 | 405.20 |
| TH010 | (structure) | | 30 | 180419 | 96 | 180419 | 287.20 |
| TH011 | (structure) | | 0 | 180419 | 96 | 180419 | 249.20 |
| TH012 | (structure) | | 15 | 180419 | 99 | 180419 | 251.20 |
| TH014 | (structure) | | 327 | 180419 | 140 | 180419 | 375.50 |
| TH016 | (structure) | | 108 | 180411 | 98 | 180419 | 330.40 |

| | | | | | | |
|---|---|---|---|---|---|---|
| TH028 | 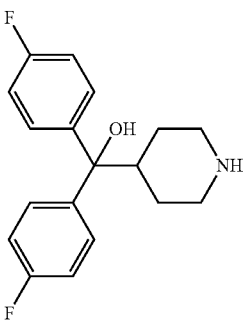 [SMILES: OC(c1ccc(F)cc1)(c1ccc(F)cc1)C1CCNCC1] | 0 | 180419 | 125 | 180419 | 303.35 |
| TH029 | 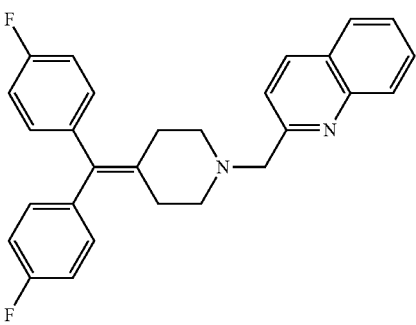 [SMILES: Fc1ccc(C(=C2CCN(Cc3ccc4ccccc4n3)CC2)c2ccc(F)cc2)cc1] | 252 | 180419 | 169 | 180419 | 426.51 |
| TH030 | 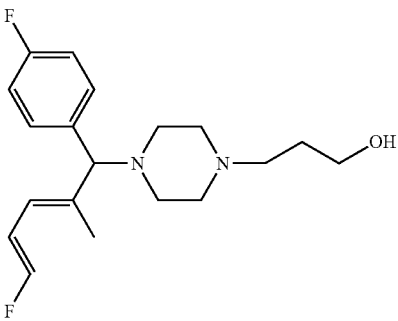 [SMILES: C/C(=C\C=C\F)C(c1ccc(F)cc1)N1CCN(CCCO)CC1] | 5 | 180419 | 91 | 180419 | 332.39 |

-continued
| Name | Structure | 1 mM % Activity | Reference sheet | 100 uM % Activity | Reference sheet | Molecular Mass |
|---|---|---|---|---|---|---|
| TH031 | 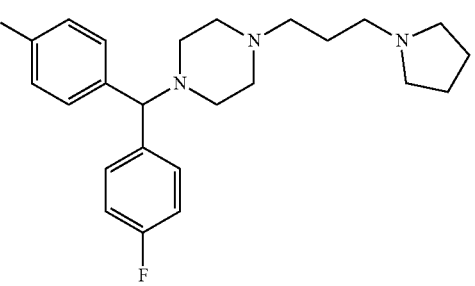 | 0 | 180419 | 105 | 180419 | 346.42 |
| Gamma Name | Structure | 1 mM % Activity | Reference sheet | 100 uM % Activity | Reference sheet | Molecular Mass |
|---|---|---|---|---|---|---|
| TH039 | 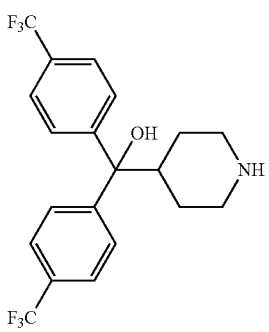 [SMILES: OC(c1ccc(C(F)(F)F)cc1)(c1ccc(C(F)(F)F)cc1)C1CCNCC1] | 1 | 180501 Gamma | 91 | 180501 Gamma | |
| TH040 | 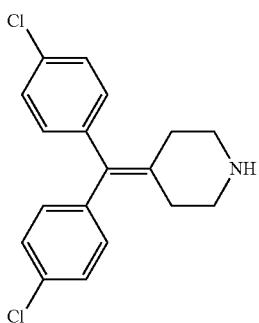 [SMILES: Clc1ccc(C(=C2CCNCC2)c2ccc(Cl)cc2)cc1] | 5 | 180501 Gamma | 101 | 180501 Gamma | |
| Name | Structure | 1 mM % Activity | Reference sheet | 100 uM % Activity | Reference sheet | Molecular Mass |
|---|---|---|---|---|---|---|
| Ritanserin | 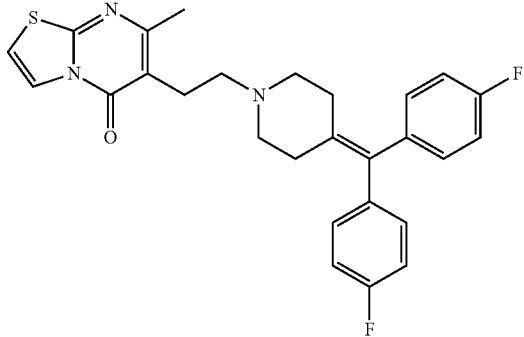 [SMILES: Cc1nc2sccn2c(=O)c1CCN1CCC(=C(c2ccc(F)cc2)c2ccc(F)cc2)CC1] | N/A | | 52 | 180222, 180228 | 477.57 |

-continued
| | | | | | | |
|---|---|---|---|---|---|---|
| Ketanserin | 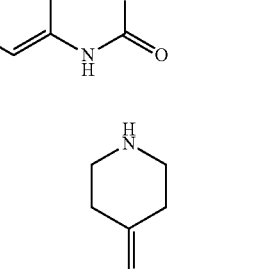 | N/A | 99 | 180222, 180228 | 395.4 | |
| RF001 | 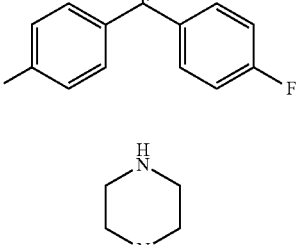 | 0 | 180228 | 75 | 160906 | 285.3 |
| TH001 | 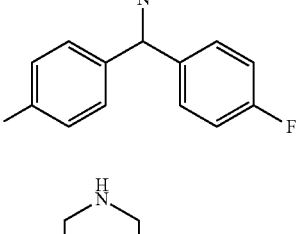 | 0 | 180221 | 72 | 180222 | 288.4 |
| TH002 | 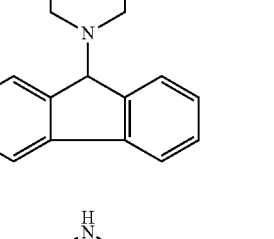 | 0 | 180221 | 84 | 180222 | 250.2 |
| TH003 | 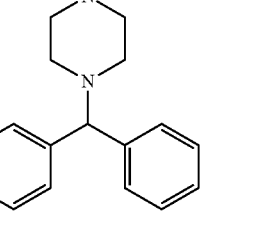 | 3 | 180221 | 88 | 180222 | 252.2 |
| TH004 | 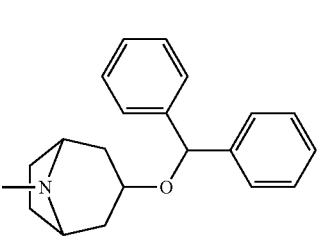 [SMILES: CN1C2CCC1CC(OC(c1ccccc1)c1ccccc1)C2] | 1 | 180221 | 93 | 180222 | 307.2 |

-continued

| | | | | | | |
|---|---|---|---|---|---|---|
| TH005 | (structure) | 14 | 180221 | 103 | 180222 | 405.2 |
| TH010 | (structure) | 64 | 180228 | N/A | | 287.2 |
| TH011 | (structure) | 0 | 180228 | 78 | 180301 | 249.2 |
| TH012 | (structure) | 41 | 180228 | N/A | | 251.2 |
| TH014 | (structure) | 160 | 180228 | N/A | | 375.5 |
| TH016 | (structure) | 139 | 180228 | N/A | | 330.4 |

-continued

| | | | | | | |
|---|---|---|---|---|---|---|
| TH019 | (4-methylphenyl)(4-methylphenyl)methylene-piperidine | 1 | 180320 | 92 | 180322 | 277.41 |
| TH022 | bis(4-fluorophenyl)methyl-piperazinyl-methyl-quinoline | 60 | 180405 | 103 | 180405 | 429.51 |
| TH024 | bis(4-fluorophenyl)methyl-piperazinyl-piperidine | 3 | 180320 | 84 | 180322 | 371.48 |
| TH025 | bis(4-methoxyphenyl)methylene-piperidine | 4.4 | 180405 | 79 | 180405 | 309.41 |
| TH028 | bis(4-fluorophenyl)(hydroxy)methyl-piperidine | 0 | 180320 | 96 | 180322 | 303.35 |

-continued

| ID | Structure | | | | | |
|---|---|---|---|---|---|---|
| TH029 | [4-fluorophenyl, 4-fluorophenyl, piperidinylidene, CH2-quinoline structure] | 73 | 180405 | 125 | 180405 | 426.51 |
| TH030 | [bis(4-fluorophenyl)methyl-piperazine-CH2CH2OH] | 36 | 180405 | 103 | 180405 | 332.39 |
| TH031 | [bis(4-fluorophenyl)methyl-piperazine-(CH2)3OH] | 26 | 180405 | 107 | 180405 | 346.42 |
| TH032 | [bis(4-fluorophenyl)methyl-piperazine-(CH2)3-pyrrolidine] | 8 | 180413 | 94 | 180413 | 399.53 |
| TH033 | [bis(4-fluorophenyl)methyl-piperazine-(CH2)3-piperazine-methyl-bis(4-fluorophenyl)] | 4 | 180413 | 72 | 180413 | 617.75 |

-continued
| | | | | | | |
|---|---|---|---|---|---|---|
| TH035 | 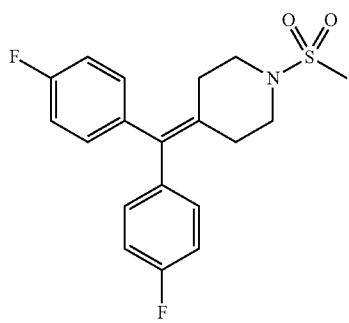 [SMILES: CS(=O)(=O)N1CCC(=C(c2ccc(F)cc2)c2ccc(F)cc2)CC1] | | 40 | 180501 Alpha | 88 | 180501 Alpha |
| TH036 | 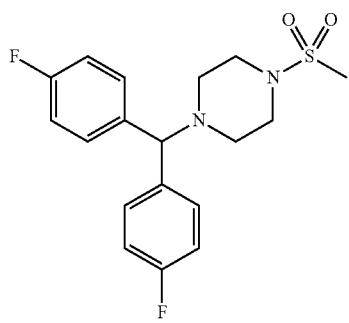 [SMILES: CS(=O)(=O)N1CCN(C(c2ccc(F)cc2)c2ccc(F)cc2)CC1] | | 74 | 180501 Alpha | 93 | 180501 Alpha |
| TH039 | 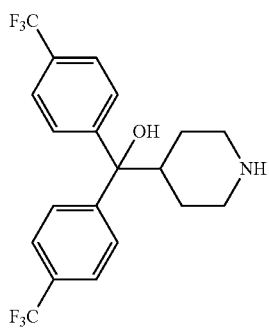 [SMILES: OC(c1ccc(C(F)(F)F)cc1)(c1ccc(C(F)(F)F)cc1)C1CCNCC1] | | 6 | 180501 Alpha | 81 | 180501 Alpha |
| TH040 | 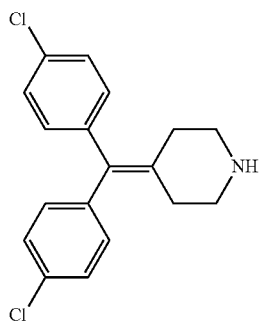 [SMILES: Clc1ccc(C(=C2CCNCC2)c2ccc(Cl)cc2)cc1] | | 4 | 180501 Alpha | 78 | 180501 Alpha |

-continued

| Zeta Name | Structure | 1 mM % Activity | Reference sheet | 100 uM % Activity | Reference sheet | Molecular Mass |
|---|---|---|---|---|---|---|
| TH032 | 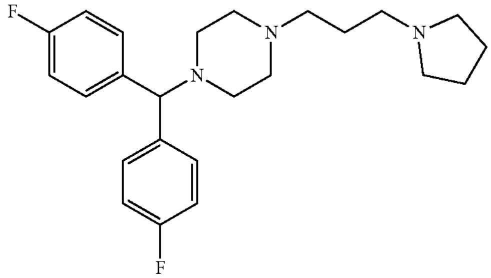 [SMILES: Fc1ccc(C(c2ccc(F)cc2)N2CCN(CCCN3CCCC3)CC2)cc1] | 0 | 180418 | 80 | 180418 | 399.53 |
| TH033 | 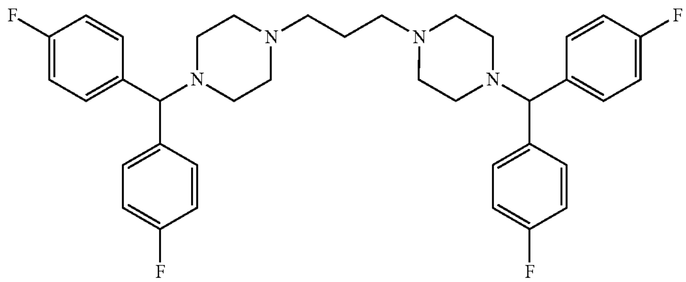 [SMILES: Fc1ccc(C(c2ccc(F)cc2)N2CCN(CCCN3CCN(C(c4ccc(F)cc4)c4ccc(F)cc4)CC3)CC2)cc1] | | 180418 | 82 | 180418 | 617.75 |
| TH035 | 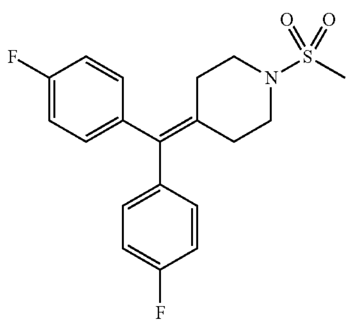 [SMILES: CS(=O)(=O)N1CCC(=C(c2ccc(F)cc2)c2ccc(F)cc2)CC1] | 100 | 180501 Zeta | 112 | 180501 Zeta | |
| TH036 | 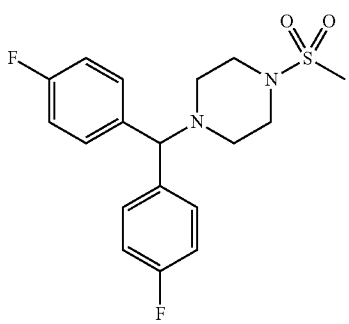 [SMILES: CS(=O)(=O)N1CCN(C(c2ccc(F)cc2)c2ccc(F)cc2)CC1] | 105 | 180501 Zeta | 108 | 180501 | |
| TH039 | 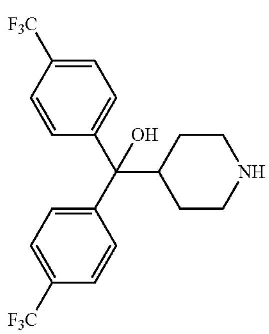 [SMILES: OC(c1ccc(C(F)(F)F)cc1)(c1ccc(C(F)(F)F)cc1)C1CCNCC1] | 1 | 180501 Zeta | 94 | 180501 Zeta | |

-continued

| Name | Structure | | 1 mM % Activity | Reference sheet | 100 uM % Activity | Reference sheet | Molecular Mass |
|---|---|---|---|---|---|---|---|
| TH040 | (4-Cl-phenyl)₂C=piperidine | | 0 | 180501 Zeta | 85 | 180501 Zeta | |

| Gamma Name | Structure | 1 mM % Activity | Reference sheet | 100 uM % Activity | Reference sheet | Molecular Mass |
|---|---|---|---|---|---|---|
| Ritanserin | 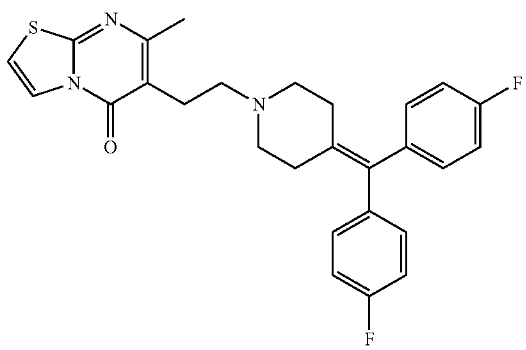 [SMILES: Cc1nc2sccn2c(=O)c1CCN1CCC(=C(c2ccc(F)cc2)c2ccc(F)cc2)CC1] | | | 55 | 180102 | 477.57 |
| Ketanserin | 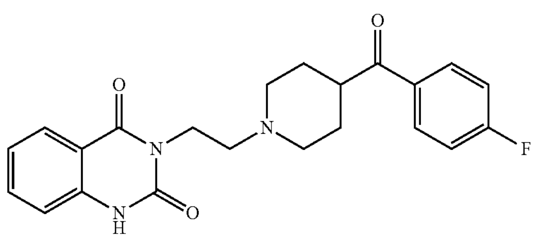 [SMILES: O=C(c1ccc(F)cc1)C1CCN(CCn2c(=O)[nH]c3ccccc3c2=O)CC1] | | | 24 | 180102 | 395.40 |
| RF001 | 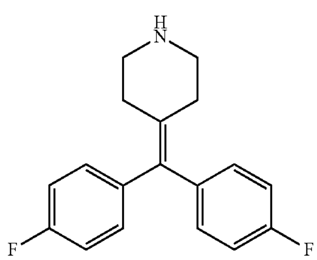 | 5 | 180418 | 82 | 180418 | 285.30 |
| TH001 | 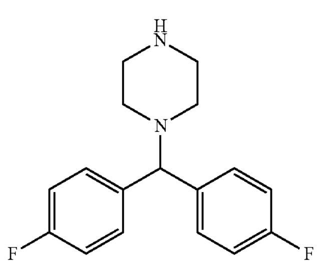 [SMILES: Fc1ccc(C(c2ccc(F)cc2)N2CCNCC2)cc1] | 0 | 180426 | 99 | 180426 | 288.40 |

-continued

| Zeta Name | Structure | 1 mM % Activity | Reference sheet | 100 uM % Activity | Reference sheet | Molecular Mass |
|---|---|---|---|---|---|---|
| TH019 | 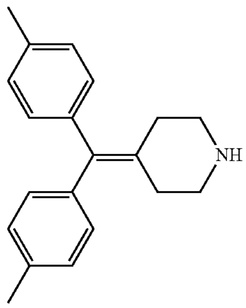 [SMILES: Cc1ccc(C(=C2CCNCC2)c2ccc(C)cc2)cc1] | 0 | 180419 | 103 | 180419 | 277.41 |
| TH022 | 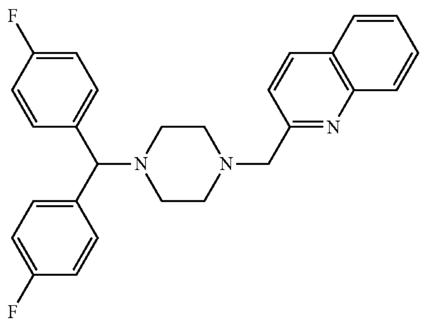 [SMILES: Fc1ccc(C(c2ccc(F)cc2)N2CCN(Cc3ccc4ccccc4n3)CC2)cc1] | 193 | 180419 | 135 | 180419 | 429.51 |
| TH024 | 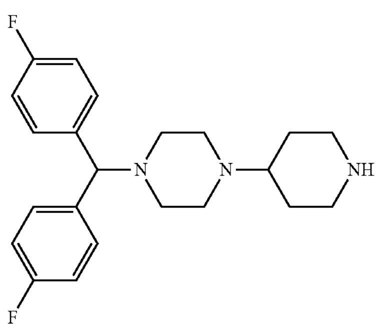 [SMILES: Fc1ccc(C(c2ccc(F)cc2)N2CCN(C3CCNCC3)CC2)cc1] | 0 | 180419 | 72 | 180419 | 371.48 |
| TH025 | 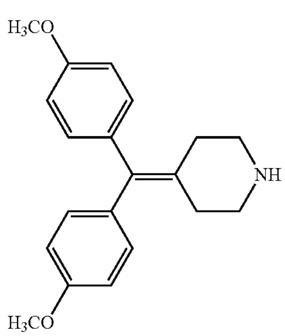 [SMILES: COc1ccc(C(=C2CCNCC2)c2ccc(OC)cc2)cc1] | 0 | 180419 | 103 | 180419 | 309.41 |

| | | | | | |
|---|---|---|---|---|---|
| Ritanserin | 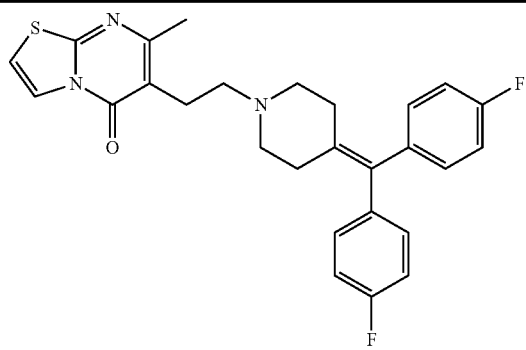 | 86 | | 180417 | 477.57 |
| Ketanserin | 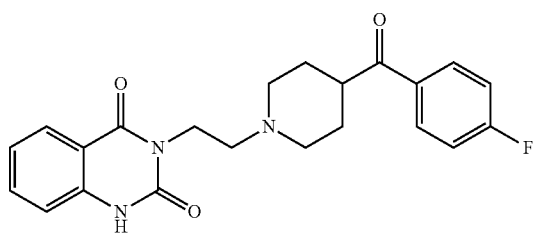 [SMILES: O=C(c1ccc(F)cc1)C1CCN(CCn2c(=O)[nH]c3ccccc3c2=O)CC1] | 90 | | 180417 | 395.40 |
| RF001 | 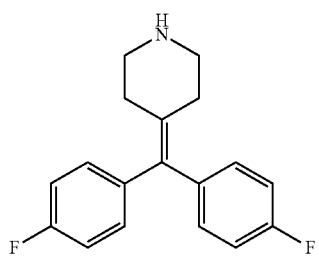 | 0 | 180417 | 80 180417 | 285.30 |
| TH001 | 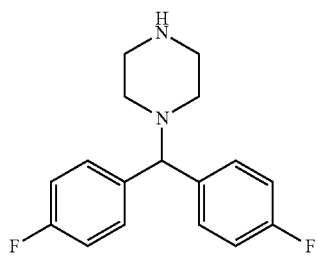 | 0 | 180419 | 102 180419 | 288.40 |

The present disclosure also contemplates pharmaceutical compositions comprising one or more compounds of the formula (1A), (I)—(V), one or more pharmaceutically acceptable carriers, diluents, excipients or combinations thereof. A "pharmaceutical composition" refers to a chemical or biological composition suitable for administration to a subject (e.g., mammal). Such compositions can be specifically formulated for administration via one or more of a number of routes, including but not limited to buccal, cutaneous, epicutaneous, epidural, infusion, inhalation, intraarterial, intracardial, intracerebroventricular, intradermal, intramuscular, intranasal, intraocular, intraperitoneal, intraspinal, intrathecal, intravenous, oral, parenteral, pulmonary, rectally via an enema or suppository, subcutaneous, subdermal, sublingual, transdermal, and transmucosal. In addition, administration can by means of capsule, drops, foams, gel, gum, injection, liquid, patch, pill, porous pouch, powder, tablet, or other suitable means of administration.

A "pharmaceutical excipient" or a "pharmaceutically acceptable excipient" comprises a carrier, sometimes a liquid, in which an active therapeutic agent is formulated. The excipient generally does not provide any pharmacological activity to the formulation, though it may provide chemical and/or biological stability, and release characteristics. Examples of suitable formulations can be found, for example, in Remington, The Science And Practice of Pharmacy, 20th Edition, (Gennaro, A. R., Chief Editor), Philadelphia College of Pharmacy and Science, 2000, which is incorporated by reference in its entirety.

As used herein "pharmaceutically acceptable carrier" or "excipient" includes any and all solvents, dispersion media, coatings, antibacterial and antifungal agents, isotonic and absorption delaying agents that are physiologically compatible. The carrier is suitable for, among other applications, parenteral administration. Alternatively, the carrier can be suitable for intravenous, intraperitoneal, intramuscular, sublingual, or oral administration. Pharmaceutically acceptable carriers include sterile aqueous solutions or dispersions and sterile powders for the extemporaneous preparation of sterile injectable solutions or dispersion. The use of such media and agents for pharmaceutically active substances is well known in the art. Except insofar as any conventional media or agent is incompatible with the active compound, use thereof in the pharmaceutical compositions is contemplated. Supplementary active compounds can also be incorporated into the compositions.

Pharmaceutical compositions can be sterile and stable under the conditions of manufacture and storage. The composition can be formulated as a solution, microemulsion, liposome, or other ordered structure suitable to high drug concentration. The carrier can be a solvent or dispersion medium containing, for example, water, ethanol, polyol (e.g., glycerol, propylene glycol, and liquid polyethylene glycol), and suitable mixtures thereof. The proper fluidity can be maintained, for example, by the use of a coating such as lecithin, by the maintenance of the required particle size in the case of dispersion and by the use of surfactants.

In many cases, it will be preferable to include isotonic agents, for example, sugars, polyalcohols such as mannitol, sorbitol, or sodium chloride in the composition. Prolonged absorption of the injectable compositions can be brought about by including in the composition an agent which delays absorption, for example, monostearate salts and gelatin. Moreover, the compounds described herein can be formulated in a time release formulation, for example in a composition that includes a slow release polymer. The active compounds can be prepared with carriers that will protect the compound against rapid release, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, polylactic acid and polylactic, polyglycolic copolymers (PLG). Many methods for the preparation of such formulations are known to those skilled in the art.

Oral forms of administration are also contemplated herein. The pharmaceutical compositions can be orally administered as a capsule (hard or soft), tablet (film coated, enteric coated or uncoated), powder or granules (coated or uncoated) or liquid (solution or suspension). The formulations can be conveniently prepared by any of the methods well-known in the art. The pharmaceutical compositions can include one or more suitable production aids or excipients including fillers, binders, disintegrants, lubricants, diluents, flow agents, buffering agents, moistening agents, preservatives, colorants, sweeteners, flavors, and pharmaceutically compatible carriers.

The compounds can be administered by a variety of dosage forms as known in the art. Any biologically-acceptable dosage form known to persons of ordinary skill in the art, and combinations thereof, are contemplated. Examples of such dosage forms include, without limitation, chewable tablets, quick dissolve tablets, effervescent tablets, reconstitutable powders, elixirs, liquids, solutions, suspensions, emulsions, tablets, multi-layer tablets, bi-layer tablets, capsules, soft gelatin capsules, hard gelatin capsules, caplets, lozenges, chewable lozenges, beads, powders, gum, granules, particles, microparticles, dispersible granules, cachets, douches, suppositories, creams, topicals, inhalants, aerosol inhalants, patches, particle inhalants, implants, depot implants, ingestibles, injectables (including subcutaneous, intramuscular, intravenous, and intradermal), infusions, and combinations thereof.

Other compounds which can be included by admixture are, for example, medically inert ingredients (e.g., solid and liquid diluent), such as lactose, dextrosesaccharose, cellulose, starch or calcium phosphate for tablets or capsules, olive oil or ethyl oleate for soft capsules and water or vegetable oil for suspensions or emulsions; lubricating agents such as silica, talc, stearic acid, magnesium or calcium stearate and/or polyethylene glycols; gelling agents such as colloidal clays; thickening agents such as gum tragacanth or sodium alginate, binding agents such as starches, arabic gums, gelatin, methylcellulose, carboxymethylcellulose or polyvinylpyrrolidone; disintegrating agents such as starch, alginic acid, alginates or sodium starch glycolate; effervescing mixtures; dyestuff; sweeteners; wetting agents such as lecithin, polysorbates or laurylsulphates; and other therapeutically acceptable accessory ingredients, such as humectants, preservatives, buffers and antioxidants, which are known additives for such formulations.

Liquid dispersions for oral administration can be syrups, emulsions, solutions, or suspensions. The syrups can contain as a carrier, for example, saccharose or saccharose with glycerol and/or mannitol and/or sorbitol. The suspensions and the emulsions can contain a carrier, for example a natural gum, agar, sodium alginate, pectin, methylcellulose, carboxymethylcellulose, or polyvinyl alcohol.

The amount of active compound in a therapeutic composition can vary according to factors such as the disease state, age, gender, weight, patient history, risk factors, predisposition to disease, administration route, pre-existing treatment regime (e.g., possible interactions with other medications), and weight of the individual. Dosage regimens can be adjusted to provide the optimum therapeutic response. For example, a single bolus can be administered, several divided doses can be administered over time, or the dose can be proportionally reduced or increased as indicated by the exigencies of therapeutic situation.

"Dosage unit form," as used herein, refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms are dictated by and can be directly dependent on the unique characteristics of the active compound and the particular therapeutic effect to be achieved, and the limitations inherent in the art of compounding such an active compound for the treatment of sensitivity in individuals. In therapeutic use for treatment of conditions in mammals (e.g., humans) for which the compounds disclosed herein or an appropriate pharmaceutical composition thereof are effective, the compounds disclosed herein can be administered in an effective amount. The dosages as suitable for this disclosure can be a composition, a pharmaceutical composition or any other compositions described herein.

The dosage can be administered once, twice, or thrice a day, although more frequent dosing intervals are possible. The dosage can be administered every day, every 2 days, every 3 days, every 4 days, every 5 days, every 6 days, and/or every 7 days (once a week). The dosage can be administered daily for up to and including 30 days, preferably between 7-10 days. Or the dosage can be administered twice a day for 10 days. If the patient requires treatment for a chronic disease or condition, the dosage can be administered for as long as signs and/or symptoms persist. The patient may require "maintenance treatment" where the patient is receiving dosages every day for months, years, or the remainder of their lives. In addition, the composition can affect prophylaxis of recurring symptoms. For example, the dosage can be administered once or twice a day to prevent the onset of symptoms in patients at risk, especially for asymptomatic patients.

The compositions described herein can be administered in any of the following routes: buccal, epicutaneous, epidural, infusion, inhalation, intraarterial, intracardial, intracerebroventricular, intradermal, intramuscular, intranasal, intraocular, intraperitoneal, intraspinal, intrathecal, intravenous, oral, parenteral, pulmonary, rectally via an enema or suppository, subcutaneous, subdermal, sublingual, transdermal, and transmucosal. The administration can be local, where the composition is administered directly, close to, in the locality, near, at, about, or in the vicinity of, the site(s) of disease, e.g., inflammation, or systemic, wherein the composition is given to the patient and passes through the body widely, thereby reaching the site(s) of disease. Local administration can be administration to the cell, tissue, organ, and/or organ system, which encompasses and/or is affected by the disease, and/or where the disease signs and/or symptoms are active or are likely to occur. Administration can be topical with a local effect, composition is applied directly where its action is desired. Administration can be enteral wherein the desired effect is systemic (non-local), composition is given via the digestive tract. Administration can be parenteral, where the desired effect is systemic, composition is given by other routes than the digestive tract.

Also contemplated herein are compositions comprising a therapeutically effective amount of one or more compounds that are useful in a method for treating various cancers including small-cell lung cancer and non-small cell lung cancer. The methods and compositions described herein can be used to treat a variety of cancers and tumors, for example, leukemia, sarcoma, osteosarcoma, lymphomas, melanoma, glioma, pheochromocytoma, hepatoma, ovarian cancer, skin cancer, testicular cancer, gastric cancer, pancreatic cancer, renal cancer, breast cancer, prostate cancer, colorectal cancer, cancer of head and neck, brain cancer, esophageal cancer, bladder cancer, adrenal cortical cancer, lung cancer, bronchus cancer, endometrial cancer, nasopharyngeal cancer, cervical or liver cancer, and cancer at an unknown primary site.

Also contemplated herein are compositions comprising a therapeutically effective amount of one or more compounds of formula (1A), (I), (II), (III), (IV) and/or (V) that are useful in a method for treating various neuropsychiatric disorders, such as, but not limited to, bipolar disorder, depression, schizophrenia, obsessive-compulsive disorder.

Also contemplated herein are compositions comprising a therapeutically effective amount of one or more compounds of formula (1A), (I), (II), (III), (IV) and/or (V) that are useful in a method for treating various neurodegenerative diseases, such as, but not limited to, multiple sclerosis, autistic spectrum disorder, Alzheimer's disease, amyotrophic lateral sclerosis (ALS), Parkinson's disease, Huntington's Disease, Guillain-Barre syndrome, myasthenia gravis, and chronic idiopathic demyelinating disease (CID).

Also contemplated herein are compositions comprising a therapeutically effective amount of one or more compounds of formula (1A), (I), (II), (III), (IV) and/or (V) that are useful in a method for activating T-cells comprising contacting a T cell, such as an inactive T cell, in vitro or in vivo, with an effective amount of one or more compounds of formula (1A), (I), (II), (III), (IV) and/or (V).

Also contemplated herein are compositions comprising an effective amount of one or more compounds of formula (1A), (I), (II), (III), (IV) and/or (V) that are useful to inhibit a kinase comprising contacting the kinase with at least one compound of formula (1A), (I), (II), (III), (IV), or (V) or the pharmaceutical composition. In one embodiment, the kinase comprises a regulatory domain, such as a C1 domain, and a kinase domain in the same protein. In one embodiment, the kinase is selected from the following:

| Uniprot | Gene | Name |
| --- | --- | --- |
| Q8N1W1 | ARG28_HUMAN | Rho guanine nucleotide exchange factor 28 |
| Q92974 | ARHG2_HUMAN | Rho guanine nucleotide exchange factor 2 |
| P10398 | ARAF_HUMAN | Serine/threonine-protein kinase A-Raf |
| P15882 | CHIN_HUMAN | N-chimaerin |
| P52757 | CHIO_HUMAN | Beta-chimaerin |
| P23743 | DGKA_HUMAN | Diacylglycerol kinase alpha |
| Q9Y6T7 | DGKB_HUMAN | Diacylglycerol kinase beta |
| P52429 | DGKE_HUMAN | Diacylglycerol kinase epsilon |
| Q6ZN54 | DEFI8_HUMAN | Differentially expressed in FDCP 8 homolog |
| Q5KSL6 | DGKK_HUMAN | Diacylglycerol kinase kappa |
| Q16760 | DGKD_HUMAN | Diacylglycerol kinase delta |
| P52824 | DGKQ_HUMAN | Diacylglycerol kinase theta |
| P49619 | DGKG_HUMAN | Diacylglycerol kinase gamma |
| Q86XP1 | DGKH_HUMAN | Diacylglycerol kinase eta |
| O14578 | CTRO_HUMAN | Citron Rho-interacting kinase |
| P15056 | BRAF_HUMAN | Serine/threonine-protein kinase B-raf |
| Q9P107 | GMIP_HUMAN | GEM-interacting protein |
| Q8IV61 | GRP3_HUMAN | Ras guanyl-releasing protein 3 |
| Q7LDG7 | GRP2_HUMAN | RAS guanyl-releasing protein 2 |
| O95267 | GRP1_HUMAN | RAS guanyl-releasing protein 1 |
| Q92619 | HMHA1_HUMAN | Rho GTPase-activating protein 45 |
| Q8IVT5 | KSR1_HUMAN | Kinase suppressor of Ras 1 |
| P17252 | KPCA_HUMAN | Protein kinase C alpha type |
| Q02156 | KPCE_HUMAN | Protein kinase C epsilon type |
| Q05513 | KPCZ_HUMAN | Protein kinase C zeta type |
| Q8TDF6 | GRP4_HUMAN | RAS guanyl-releasing protein 4 |
| P24723 | KPCL_HUMAN | Protein kinase C eta type |
| Q04759 | KPCT_HUMAN | Protein kinase C theta type |
| Q6VAB6 | KSR2_HUMAN | Kinase suppressor of Ras 2 |
| P05771 | KPCB_HUMAN | Protein kinase C beta type |
| O94806 | KPCD3_HUMAN | Serine/threonine-protein kinase D3 |
| P05129 | KPCG_HUMAN | Protein kinase C gamma type |
| P41743 | KPCI_HUMAN | Protein kinase C iota type |
| P04049 | RAF1_HUMAN | RAF proto-oncogene serine/threonine-protein kinase |
| Q9NS23 | RASF1_HUMAN | Ras association domain-containing protein 1 |
| Q8WWW0 | RASF5_HUMAN | Ras association domain-containing protein 5 |
| Q52LW3 | RHG29_HUMAN | Rho GTPase-activating protein 29 |
| Q13464 | ROCK1_HUMAN | Rho-associated protein kinase 1 |
| O75116 | ROCK2_HUMAN | Rho-associated protein kinase 2 |
| Q9H0H5 | RGAP1_HUMAN | Rac GTPase-activating protein 1 |
| Q12802 | AKP13_HUMAN | A-kinase anchor protein 13 |
| Q5VT25 | MRCKA_HUMAN | Serine/threonine-protein kinase MRCK alpha |
| Q9Y4G2 | PKHM1_HUMAN | Pleckstrin homology domain-containing family M member 1 |
| Q8NEN9 | PDZD8_HUMAN | PDZ domain-containing protein 8 |
| Q13459 | MYO9B_HUMAN | Unconventional myosin-IXb |
| Q6DT37 | MRCKG_HUMAN | Serine/threonine-protein kinase MRCK gamma |
| Q9Y5S2 | MRCKB_HUMAN | Serine/threonine-protein kinase MRCK beta |
| B2RTY4 | MYO9A_HUMAN | Unconventional myosin-IXa |
| Q15139 | KPCD1_HUMAN | Serine/threonine-protein kinase D1 |
| Q9BZL6 | KPCD2_HUMAN | Serine/threonine-protein kinase D2 |
| Q05655 | KPCD_HUMAN | Protein kinase C delta type |
| Q99469 | STAC_HUMAN | SH3 and cysteine-rich domain-containing protein |
| Q96MF2 | STAC3_HUMAN | SH3 and cysteine-rich domain-containing protein 3 |
| Q6ZMT1 | STAC2_HUMAN | SH3 and cysteine-rich domain-containing protein 2 |
| P52735 | VAV2_HUMAN | Guanine nucleotide exchange factor VAV2 |

| Uniprot | Gene | Name |
| --- | --- | --- |
| Q9UKW4 | VAV3_HUMAN | Guanine nucleotide exchange factor VAV3 |
| Q9UPW8 | UN13A_HUMAN | Protein unc-13 homolog A |
| Q8NB66 | UN13C_HUMAN | Protein unc-13 homolog C |
| O14795 | UN13B_HUMAN Protein unc-13 homolog B | |
| Q63HR2 | TNS2_HUMAN | Tensin-2 |
| P15498 | VAV_HUMAN | Proto-oncogene vav |

The term "therapeutically effective amount" as used herein, refers to that amount of one or more compounds of the formula (1A), (I), (II), (III), (IV) and/or (V) that elicits a biological or medicinal response in a tissue system, animal or human, that is being sought by a researcher, veterinarian, medical doctor or other clinician, which includes alleviation of the symptoms of the disease or disorder being treated. The therapeutically effective amount can be that which may treat or alleviate the disease or symptoms of the disease at a reasonable benefit/risk ratio applicable to any medical treatment. However, it is to be understood that the total daily usage of the compounds and compositions described herein can be decided by the attending physician within the scope of sound medical judgment. The specific therapeutically-effective dose level for any particular patient will depend upon a variety of factors, including the condition being treated and the severity of the condition; activity of the specific compound employed; the specific composition employed; the age, body weight, general health, gender and diet of the patient: the time of administration, route of administration, and rate of excretion of the specific compound employed; the duration of the treatment; drugs used in combination or coincidentally with the specific compound employed; and like factors well known to the researcher, veterinarian, medical doctor or other clinician. It is also appreciated that the therapeutically effective amount can be selected with reference to any toxicity, or other undesirable side effect, that might occur during administration of one or more of the compounds described herein.

The present disclosure also contemplates compounds of the formula (1A), (I)—(V) having a activity $EC_{50}$ value of less than 250 µM, less than 150 µM, less than 100 µM, less than 50 µM, less than 25 µM, less than 10 UM, less than 1 µM, less than 500 nM; or from about 1 nM to about 1 µM, about 1 µM to about 50 µM, about 1 µM to about 20 µM, about 1 nM to about 200 nM, about 50 nM to about 500 nM or about 10 nM to about 150 nM.

The present disclosure also contemplates compounds of the formula (1A), (I)—(V) having a % inhibition of at least about 10%, at least about 20%, at least about 30%, at least about 40%, at least about 50%, at least about 60%, at least about 70%, at least about 80%, at least about 90%, at least about 99%; or about 20% to about 100%, about 30% to about 90%, about 40% to about 95%, about 50% to about 90% or about 70% to about 95%.

The present disclosure also contemplates compounds of the formula (1A), (I)—(V) having a combination of the two of the aforementioned $EC_{50}$ values and % inhibition.

Values expressed in a range format should be interpreted in a flexible manner to include not only the numerical values explicitly recited as the limits of the range, but also to include all the individual numerical values or sub-ranges encompassed within that range as if each numerical value and sub-range were explicitly recited. For example, a range of "about 0.1% to about 5%" or "about 0.1% to 5%" should be interpreted to include not just about 0.1% to about 5%, but also the individual values (e.g., 1%, 2%, 3%, and 4%) and the sub-ranges (e.g., 0.1% to 0.5%, 1.1% to 2.2%, 3.3% to 4.4%) within the indicated range. The statement "about X to Y" has the same meaning as "about X to about Y," unless indicated otherwise. Likewise, the statement "about X, Y, or about Z" has the same meaning as "about X, about Y, or about Z," unless indicated otherwise.

In this document, the terms "a," "an," or "the" are used to include one or more than one unless the context clearly dictates otherwise. The term "or" is used to refer to a nonexclusive "or" unless otherwise indicated. In addition, it is to be understood that the phraseology or terminology employed herein, and not otherwise defined, is for the purpose of description only and not of limitation. Any use of section headings is intended to aid reading of the document and is not to be interpreted as limiting. Further, information that is relevant to a section heading may occur within or outside of that particular section. Furthermore, all publications, patents, and patent documents referred to in this document are incorporated by reference herein in their entirety, as though individually incorporated by reference.

In the methods described herein, the steps can be carried out in any order without departing from the spirit of this disclosure, except when a temporal or operational sequence is explicitly recited. Furthermore, specified steps can be carried out concurrently unless explicit claim language recites that they be carried out separately. For example, a claimed step of doing X and a claimed step of doing Y can be conducted simultaneously within a single operation, and the resulting process will fall within the literal scope of the claimed process.

The term "about" as used herein can allow for a degree of variability in a value or range, for example, within 10%, within 5%, or within 1% of a stated value or of a stated limit of a range.

The term "substituted" as used herein in conjunction with a molecule or an organic group as defined herein refers to the state in which one or more hydrogen atoms contained therein are replaced by one or more non-hydrogen atoms. The term "functional group" or "substituent" as used herein refers to a group that can be or is substituted onto a molecule or onto an organic group. Examples of substituents or functional groups include, but are not limited to, a halogen (e.g., F, Cl, Br, and I); an oxygen atom in groups such as hydroxy groups, alkoxy groups, aryloxy groups, aralkyloxy groups, oxo (carbonyl) groups, carboxyl groups including carboxylic acids, carboxylates, and carboxylate esters; a sulfur atom in groups such as thiol groups, alkyl and aryl sulfide groups, sulfoxide groups, sulfone groups, sulfonyl groups, and sulfonamide groups; a nitrogen atom in groups such as amines, hydroxyamines, nitriles, nitro groups, N-oxides, hydrazides, azides, and enamines; and other heteroatoms in various other groups. Non-limiting examples of substituents that can be bonded to a substituted carbon (or other) atom include F, Cl, Br, I, OR, OC(O)N(R)$_2$, CN, NO, NO$_2$, ONO$_2$, azido, CF$_3$, OCF$_3$, R, O (oxo), S (thiono), C(O), S(O), methylenedioxy, ethylenedioxy, N(R)$_2$, SR, SOR, SO$_2$R, SO$_2$N(R)$_2$, SO$_3$R, C(O)R, C(O)C(O)R, C(O)CH$_2$C(O)R, C(S)R, C(O)OR, OC(O)R, C(O)N(R)$_2$, OC(O)N(R)$_2$, C(S)N(R)$_2$, (CH$_2$)$_{0-2}$N(R)C(O)R, (CH$_2$)$_{0-2}$N(R)N(R)$_2$, N(R)N(R)C(O)R, N(R)N(R)C(O)OR, N(R)N(R)CON(R)$_2$, N(R)SO$_2$R, N(R)SO$_2$N(R)$_2$, N(R)C(O)OR, N(R)C(O)R, N(R)C(S)R, N(R)C(O)N(R)$_2$, N(R)C(S)N(R)$_2$, N(COR)COR, N(OR)R, C(=NH)N(R)$_2$, C(O)N(OR)R, and C(=NOR)R, wherein R can be hydrogen or a carbon-based moiety; for example, R can be hydrogen, ($C_1$-$C_{100}$) hydrocarbyl, alkyl, acyl, cycloalkyl, aryl, aralkyl, heterocyclyl, heteroaryl, or heteroarylalkyl; or wherein two R groups bonded to a nitrogen atom or to adjacent nitrogen atoms can together with the nitrogen atom or atoms form a heterocyclyl.

The term "alkyl" as used herein refers to straight chain and branched alkyl groups and cycloalkyl groups having from 1 to 40 carbon atoms, 1 to about 20 carbon atoms, 1 to 12 carbons or, in some embodiments, from 1 to 8 carbon atoms. Examples of straight chain alkyl groups include those with from 1 to 8 carbon atoms such as methyl, ethyl, n-propyl, n-butyl, n-pentyl, n-hexyl, n-heptyl, and n-octyl groups. Examples of branched alkyl groups include, but are not limited to, isopropyl, iso-butyl, sec-butyl, t-butyl, neopentyl, isopentyl, and 2,2-dimethylpropyl groups. As used herein, the term "alkyl" encompasses n-alkyl, isoalkyl, and anteisoalkyl groups as well as other branched chain forms of alkyl. Representative substituted alkyl groups can be substituted one or more times with any of the groups listed herein, for example, amino, hydroxy, cyano, carboxy, nitro, thio, alkoxy, and halogen groups.

The term "alkenyl" as used herein refers to straight and branched chain and cyclic alkyl groups as defined herein, except that at least one double bond exists between two carbon atoms. Thus, alkenyl groups have from 2 to 40 carbon atoms, or 2 to about 20 carbon atoms, or 2 to 12 carbon atoms or, in some embodiments, from 2 to 8 carbon atoms. Examples include, but are not limited to vinyl, —CH=CH(CH$_3$), —CH=C(CH$_3$)$_2$, —C(CH$_3$)=CH$_2$, —C(CH$_3$)=CH(CH$_3$), —C(CH$_2$CH$_3$)=CH$_2$, cyclohexenyl, cyclopentenyl, cyclohexadienyl, butadienyl, pentadienyl, and hexadienyl among others.

The term "organic group" as used herein refers to any carbon-containing functional group. Examples can include an oxygen-containing group such as an alkoxy group, aryloxy group, aralkyloxy group, oxo (carbonyl) group; a carboxyl group including a carboxylic acid, carboxylate, and a carboxylate ester; a sulfur-containing group such as an alkyl and aryl sulfide group; and other heteroatom-containing groups. Non-limiting examples of organic groups include OR, OOR, OC(O)N(R)$_2$, CN, CF$_3$, OCF$_3$, R, C(O), methylenedioxy, ethylenedioxy, N(R)$_2$, SR, SOR, SO$_2$R, SO$_2$N(R)$_2$, SO$_3$R, C(O)R, C(O)C(O)R, C(O)CH$_2$C(O)R, C(S)R, C(O)OR, OC(O)R, C(O)N(R)$_2$, OC(O)N(R)$_2$, C(S) N(R)$_2$, (CH$_2$)$_{0-2}$N(R)C(O)R, (CH$_2$)$_{0-2}$N(R)N(R)$_2$, N(R)N (R)C(O)R, N(R)N(R)C(O)OR, N(R)N(R)CON(R)$_2$, N(R) SO$_2$R, N(R)SO$_2$N(R)$_2$, N(R)C(O)OR, N(R)C(O)R, N(R)C (S)R, N(R)C(O)N(R)$_2$, N(R)C(S)N(R)$_2$, N(COR)COR, N(OR)R, C(=NH) N(R)$_2$, C(O)N(OR)R, C(=NOR)R, and substituted or unsubstituted ($C_1$-$C_{100}$) hydrocarbyl, wherein R can be hydrogen (in examples that include other carbon atoms) or a carbon-based moiety, and wherein the carbon-based moiety can be substituted or unsubstituted.

The term "alkynyl" as used herein refers to straight and branched chain alkyl groups, except that at least one triple bond exists between two carbon atoms. Thus, alkynyl groups have from 2 to 40 carbon atoms, 2 to about 20 carbon atoms, or from 2 to 12 carbons or, in some embodiments, from 2 to 8 carbon atoms. Examples include, but are not limited to —C≡CH, —C≡C(CH$_3$), —C≡C(CH$_2$CH$_3$), —CH$_2$C≡CH, —CH$_2$C≡C(CH$_3$), and —CH$_2$C≡C (CH$_2$CH$_3$) among others.

As used herein, the term "alkynylenyl" broadly refers to substituted or unsubstituted divalent straight chain and branched alkynylenyl groups having from 1 to 40 carbon atoms ($C_1$-$C_{40}$), from 1 to about 20 carbon atoms ($C_1$-$C_{20}$), from 1 to 12 carbons ($C_1$-$C_{12}$), from 1 to 8 carbon atoms ($C_1$-$C_8$), or, in some examples, from 1 to 6 carbon atoms ($C_1$-$C_6$). Examples of straight chain divalent alkynylenyl groups include those with from 1 to 8 carbon atoms such as ethynyl (—C≡C—CH$_2$—), n-propynyl (—C≡C—CH$_2$—), and the like.

The term "cycloalkyl" as used herein refers to cyclic alkyl groups such as, but not limited to, cyclopropyl, cyclobutyl, cyclopentyl, cyclohexyl, cycloheptyl, and cyclooctyl groups. In some embodiments, the cycloalkyl group can have 3 to about 8-12 ring members, whereas in other embodiments the number of ring carbon atoms range from 3 to 4, 5, 6, or 7. Cycloalkyl groups further include polycyclic cycloalkyl groups such as, but not limited to, norbornyl, adamantyl, bornyl, camphenyl, isocamphenyl, and carenyl groups, and fused rings such as, but not limited to, decalinyl, and the like. Cycloalkyl groups also include rings that are substituted with straight or branched chain alkyl groups as defined herein. Representative substituted cycloalkyl groups can be mono-substituted or substituted more than once, such as, but not limited to, 2,2-, 2,3-, 2,4-2,5- or 2,6-disubstituted cyclohexyl groups or mono-, di- or tri-substituted norbornyl or cycloheptyl groups, which can be substituted with, for example, amino, hydroxy, cyano, carboxy, nitro, thio, alkoxy, and halogen groups. The term "cycloalkenyl" alone or in combination denotes a cyclic alkenyl group.

The term "acyl" as used herein refers to a group containing a carbonyl moiety wherein the group is bonded via the carbonyl carbon atom. The carbonyl carbon atom is bonded to a hydrogen forming a "formyl" group or is bonded to another carbon atom, which can be part of an alkyl, aryl, aralkyl cycloalkyl, cycloalkylalkyl, heterocyclyl, heterocyclylalkyl, heteroaryl, heteroarylalkyl group or the like. An acyl group can include 0 to about 12, 0 to about 20, or 0 to about 40 additional carbon atoms bonded to the carbonyl group. An acyl group can include double or triple bonds within the meaning herein. An acryloyl group is an example of an acyl group. An acyl group can also include heteroatoms within the meaning herein. A nicotinoyl group (pyridyl-3-carbonyl) is an example of an acyl group within the meaning herein. Other examples include acetyl, benzoyl, phenylacetyl, pyridylacetyl, cinnamoyl, and acryloyl groups and the like. When the group containing the carbon atom that is bonded to the carbonyl carbon atom contains a halogen, the group is termed a "haloacyl" group. An example is a trifluoroacetyl group.

The term "aryl" as used herein refers to cyclic aromatic hydrocarbon groups that do not contain heteroatoms in the ring. Thus, aryl groups include, but are not limited to, phenyl, azulenyl, heptalenyl, biphenyl, indacenyl, fluorenyl, phenanthrenyl, triphenylenyl, pyrenyl, naphthacenyl, chrysenyl, biphenylenyl, anthracenyl, and naphthyl groups. In some embodiments, aryl groups contain about 6 to about 14 carbons in the ring portions of the groups. Aryl groups can be unsubstituted or substituted, as defined herein. Representative substituted aryl groups can be mono-substituted or substituted more than once, such as, but not limited to, a phenyl group substituted at any one or more of 2—, 3-, 4-, 5-, or 6-positions of the phenyl ring, or a naphthyl group substituted at any one or more of 2-to 8-positions thereof.

The term "aralkyl" and "arylalkyl" as used herein refers to alkyl groups as defined herein in which a hydrogen or carbon bond of an alkyl group is replaced with a bond to an aryl group as defined herein. Representative aralkyl groups include benzyl and phenylethyl groups and fused (cycloalkylaryl)alkyl groups such as 4-ethyl-indanyl. Aralkenyl groups are alkenyl groups as defined herein in which a hydrogen or carbon bond of an alkyl group is replaced with a bond to an aryl group as defined herein.

The term "arylenyl" as used herein refers to divalent groups that are derived by removing two hydrogen atoms from an "arylalkyl" group. Examples of arylenenyl groups include the group:

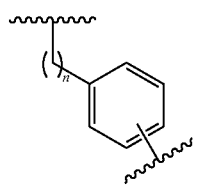

wherein the wavy lines represent the points of attachment.

The term "heterocyclyl" as used herein refers to substituted or unsubstituted aromatic and non-aromatic ring compounds containing 3 or more ring members, of which, one or more is a heteroatom such as, but not limited to, N, O, and S. Thus, a heterocyclyl can be a cycloheteroalkyl, or a heteroaryl, or if polycyclic, any combination thereof. Heterocyclyl groups can include 3 to about 20 ring members, whereas other such groups have 3 to about 15 ring members. Heterocyclyl groups include heterocyclyl groups that include 3 to 8 carbon atoms ($C_3$-$C_8$), 3 to 6 carbon atoms ($C_3$-$C_6$) or 6 to 8 carbon atoms ($C_6$-$C_8$). A heterocyclyl group designated as a $C_2$-heterocyclyl can be a 5-ring with two carbon atoms and three heteroatoms, a 6-ring with two carbon atoms and four heteroatoms and so forth. Likewise, a $C_4$-heterocyclyl can be a 5-ring with one heteroatom, a 6-ring with two heteroatoms, and so forth. The number of carbon atoms plus the number of heteroatoms equals the total number of ring atoms. A heterocyclyl ring can also include one or more double bonds. A heteroaryl ring is an example of a heterocyclyl group. The phrase "heterocyclyl group" includes fused ring species including those that include fused aromatic and non-aromatic groups. Representative heterocyclyl groups include, but are not limited to piperidynyl, piperazinyl, morpholinyl, furanyl, pyrrolidinyl, pyridinyl, pyrazinyl, pyrimidinyl, triazinyl, thiophenyl, tetrahydrofuranyl, pyrrolyl, oxazolyl, imidazolyl, triazyolyl, tetrazolyl, benzoxazolinyl, and benzimidazolinyl groups.

The term "alkoxy" as used herein refers to an oxygen atom connected to an alkyl group, including a cycloalkyl group, as are defined herein. Examples of linear alkoxy groups include but are not limited to methoxy, ethoxy, propoxy, butoxy, pentyloxy, hexyloxy, and the like. Examples of branched alkoxy include but are not limited to isopropoxy, sec-butoxy, tert-butoxy, isopentyloxy, isohexyloxy, and the like. Examples of cyclic alkoxy include but are not limited to cyclopropyloxy, cyclobutyloxy, cyclopentyloxy, cyclohexyloxy, and the like. An alkoxy group can include about 1 to about 12, about 1 to about 20, or about 1 to about 40 carbon atoms bonded to the oxygen atom, and can further include double or triple bonds, and can also include heteroatoms. For example, an allyloxy group or a methoxyethoxy group is also an alkoxy group within the meaning herein, as is a methylenedioxy group in a context where two adjacent atoms of a structure are substituted therewith.

The term "amine" as used herein refers to primary, secondary, and tertiary amines having, e.g., the formula N(group)$_3$ wherein each group can independently be H or non —H, such as alkyl, aryl, and the like. Amines include but are not limited to R—NH$_2$, for example, alkylamines, arylamines, alkylarylamines; R$_2$NH wherein each R is independently selected, such as dialkylamines, diarylamines, aralkylamines, heterocyclylamines and the like; and R$_3$N wherein each R is independently selected, such as trialkylamines, dialkylarylamines, alkyldiarylamines, triarylamines, and the like. The term "amine" also includes ammonium ions as used herein.

The terms "halo," "halogen," or "halide" group, as used herein, by themselves or as part of another substituent, mean, unless otherwise stated, a fluorine, chlorine, bromine, or iodine atom.

The term "haloalkyl" group, as used herein, includes mono-halo alkyl groups, poly-halo alkyl groups wherein all halo atoms can be the same or different, and per-halo alkyl groups, wherein all hydrogen atoms are replaced by halogen atoms, such as fluoro. Examples of haloalkyl include trifluoromethyl, 1,1-dichloroethyl, 1,2-dichloroethyl, 1,3-dibromo-3,3-difluoropropyl, perfluorobutyl, and the like.

As used herein, the term "hydrocarbyl" refers to a functional group derived from a straight chain, branched, or cyclic hydrocarbon, and can be alkyl, alkenyl, alkynyl, aryl, cycloalkyl, acyl, or any combination thereof. Hydrocarbyl groups can be shown as ($C_a$-$C_b$) hydrocarbyl, wherein a and b are integers and mean having any of a to b number of carbon atoms. For example, ($C_1$-$C_4$) hydrocarbyl means the hydrocarbyl group can be methyl ($C_1$), ethyl ($C_2$), propyl ($C_3$), or butyl ($C_4$), and ($C_0$-$C_b$) hydrocarbyl means in certain embodiments there is no hydrocarbyl group.

As used herein, the term "salts" and "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic groups such as amines; and alkali or organic salts of acidic groups such as carboxylic acids. Pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, and nitric; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, and isethionic, and the like.

Pharmaceutically acceptable salts can be synthesized from the parent compound which contains a basic or acidic moiety by conventional chemical methods. In some instances, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in Remington's Pharmaceutical Sciences, 17th ed., Mack Publishing Company, Easton, Pa., 1985, the disclosure of which is hereby incorporated by reference.

The term "solvate" means a compound, or a salt thereof, that further includes a stoichiometric or non-stoichiometric amount of solvent bound by non-covalent intermolecular forces. Where the solvent is water, the solvate is a hydrate.

The term "prodrug" means a derivative of a compound that can hydrolyze, oxidize, or otherwise react under biological conditions (in vitro or in vivo) to provide an active compound, particularly a compound according to the instant disclosure. Examples of prodrugs include, but are not limited to, derivatives and metabolites of compounds described herein that include biohydrolyzable moieties such as biohydrolyzable amides, biohydrolyzable esters, biohydrolyzable carbamates, biohydrolyzable carbonates, biohydrolyzable ureides, and biohydrolyzable phosphate analogues. Specific prodrugs of compounds with carboxyl functional groups are the lower alkyl esters of the carboxylic acid. The carboxylate esters are conveniently formed by esterifying any of the carboxylic acid moieties present on the molecule. Prodrugs can typically be prepared using well-known methods, such as those described by Burger's Medicinal Chemistry and Drug Discovery 6th ed. (Donald J. Abraham ed., 2001, Wiley) and Design and Application of Prodrugs (H. Bundgaard ed., 1985, Harwood Academic Publishers GmbH).

EXAMPLES

The following examples are offered by way of illustration. But the present disclosure is not limited to the examples given herein.

Example 1

The Ligand Binding Landscape of Diacylglycerol Kinases

INTRODUCTION

Diacylglycerols (DAGs) and phosphatidic acid (PA) play roles in biology as basic components of membranes, intermediates in lipid metabolism, and secondary messengers in cellular signaling (Carrasco and Merida, 2007; Fang et al., 2001). Cells regulate intracellular DAG and PA levels through metabolic networks that utilize distinct enzymes to produce or consume these secondary messengers/metabolites (Brown et al., 2017; Carrasco and Merida, 2007; Hsu et al., 2012; Shulga et al., 2011). One such enzymatic pathway of signal transduction is adenosine triphosphate (ATP)-dependent phosphorylation of DAGs to biosynthesize phosphatidic acid (PA, FIG. 1A) by a set of lipid kinases collectively known as diacylglycerol kinases (Shulga et al., 2011) (DGKs). DAG and PA are lipid messengers that alter localization (Takai et al., 1979), activation (Newton and Koshland, 1989), and protein-protein interactions (Fang et al., 2001) of distinct sets of receptor proteins. Consequently, disruption of the same DGK protein in different cell types can result in opposing effects that can be leveraged, for example, in cancer to simultaneously block tumor growth and activate antitumor immunity (Merida et al., 2017; Sakane et al., 2016). Since DAG and PA serve as intermediates in lipid metabolism, DGKs are uniquely positioned as regulators of the structural, bio-energetic, and signaling demands of cells.

Ten mammalian DGKs have been identified and classified into five subtypes based on structural features elucidated from primary sequence analysis (FIG. 1B). At the N-terminus, DGKs contain at least two cysteine-rich zinc finger-like motifs similar to C1 domains found in protein kinase C(Carrasco and Merida, 2007) (PKC). DGKs contain a C-terminal catalytic domain composed of a conserved catalytic region (SMART domain (Schultz et al., 1998) DAGKc, SM000046), which is present in other eukaryotic lipid kinases and DGKs from Gram-positive bacteria (Adams et al., 2016), followed by an accessory subdomain (DAGKa, SM000045) of unknown function (Merida et al., 2017). While DGKs share the same basic domain organization, individual subtypes differ in regulatory domains proposed to mediate metal binding (EF hand motifs), oligomerization (SAM domain), membrane association (PH domain), subcellular localization (MARCKS domain), or protein-protein interactions (ankyrin repeats, PDZ domain) (Shulga et al., 2011). Given the chemical diversity of DAG and PA lipids (Yetukuri et al., 2008), understanding the cross-talk between regulatory and catalytic domains of DGKs will be allow for assigning metabolic and signaling functions to individual isoforms.

Attempts to define the function of individual DGK domains have resulted in inconclusive results. ATP-binding motifs corresponding to the glycine-rich loops found in protein kinases (GxGxxG consensus sequence (Hanks et al., 1988; Hemmer et al., 1997)) were identified in the first C1 and catalytic domains of DGKs (Sakane et al., 1990; Schaap et al., 1994). Mutation of lysines in these motifs, which abolishes ATP binding and protein kinase activity, did not affect catalytic function of DGKs and led others to hypothesize the existence of a DGK-specific ATP binding motif that remains to be defined (Sakane et al., 1996; Schaap et al., 1994). The role of C1 domains in DGK function is also enigmatic. With the exception of gamma and beta isoforms (Shindo et al., 2003), the C1 domains of DGKs lack conserved residues identified as being required for DAG binding in other proteins including PKC(Hurley and Misra, 2000). In vitro biochemical studies measuring activity of C1 truncation mutants have produced conflicting reports with regards to whether C1 motifs are required (Abe et al., 2003; Houssa et al., 1997; Santos et al., 2002) or dispensable (Merino et al., 2007; Sakane et al., 1996) for maximal DGK catalytic activity.

Thus, DGK active sites remain ill-defined and, combined with the lack of crystal structures for mammalian DGKs, have limited the understanding of substrate and inhibitor binding. As a result, current DGK inhibitors consist of compounds with poor specificity within the DGK superfamily (de Chaffoy de Courcelles et al., 1989; de Chaffoy de Courcelles et al., 1985) or lack selectivity measurements against other lipid and protein kinases (Boroda et al., 2017; Liu et al., 2016; Purow, 2015). Thus, methods that provide information on small molecule binding mode and selectivity are needed to guide development of isoform-selective DGK inhibitors. Selective DGK inhibitors are needed to study isoforms where knockout mice viability is an issue (Crotty et al., 2006) and to help realize the translational potential of targeting specific forms, e.g. DGK-alpha (DGKα), for anti-cancer (Dominguez et al., 2013) and immunotherapy applications (Prinz et al., 2012).

Here, ATP acyl phosphate activity-based probes (Patricelli et al., 2011; Patricelli et al., 2007) and quantitative mass spectrometry were used to discover ATP- and inhibitor-binding sites of representative members of all five principal DGK subtypes. The findings define, for the first time, the ATP binding motif of DGKs that is distinct from protein kinases and identifies the DAGKa subdomain as a novel region mediating ATP binding. A fragment of the DGKα inhibitor ritanserin was discovered that shows conservation of binding mode and enhanced selectivity against protein kinases, supporting the concept that the atypical C1 and accessory region of the catalytic domain (DAGKa) are ligand-binding sites for developing DGKα-selective inhibitors. The studies demonstrate the utility of chemical proteomics to map ligand binding sites for fragment-based discovery of lipid kinase inhibitors.

Materials and Methods

Reagents

| REAGENT or RESOURCE | SOURCE | IDENTIFIER |
|---|---|---|
| Antibodies | | |
| HA Epitope Tag Monoclonal Antibody produced in mouse | Thermo Fisher Scientific | Cat# P126183; RRID: AB_2533052 |
| Anti-FLAG antibody produced in rabbit | Sigma-Aldrich | Cat# F7426; RR1D: AB_439687 |
| Goat anti-mouse DyLight 650 | Thermo Fisher Scientific | Cat# 84545; RRID: AB_10942301 |
| Goat anti-rabbit DyLight 550 | Thermo Fisher Scientific | Cat# 84541; RRID: AB_10942173 |
| Chemicals, Peptides and Recombinant Protiens | | |
| Desthiobiotin ATP acyl Phosphate nucleotide Probe | Thermo Fisher Scientific | Cat# P188311 |
| Polyetheleneimine | Polysciences, Inc | Cat# 24765 |
| Ritanserin | Tocris Bioscience | Cat# 1955 |
| Ketanserin tartrate | Tocris Bioscience | Cat# 0908 |
| 4-(Bis(4-fluorophenyl)methylene) piperidine (RF001) | Matrix Scientific | Cat# 126170 |
| R59022 | Sigma-Aldrich | Cat# D5919 |
| R59949 | Sigma-Aldrich | Cat# D5794 |
| 1,2-Dioleoyl-sn-glycerol (DG) | Avanti Polar Lipids | Cat# 800811C |
| 1 2-dioleoyl-sn-glycero-3-phospho-L-serine (DOPS) | Avanti Polar Lipids | Cat# 840035C |
| L(+)-Arginine hydrocholoride | Acros Organics | Cat# 105000250 |
| L-Lysine dihydrocholoride | Acros Organics | Cat# 413360250 |
| L-Arginine-$^{13}C_6$, $^{15}N_4$ hydrochloride | Sigma-Aldrich | Cat# 608033-1G |
| L-Lysine-$^{13}C_6$, $^{15}N_2$ hydrochloride | Sigma-Aldrich | Cat#608041-1G |
| Critical Commercial Assays | | |
| DC Protien Assay Kit II | Bio-Rad | Cat# 5000112 |
| ADP-Glo ™ assay | Promega | Cat# V9101 |
| Gateway ® LR Clonase ® II Enzyme Mix | Thermo Fisher Scientific | Cat# 11791020 |
| Experimental Models: Cell Lines | | |
| HEK293T | ATCC | |
| Recombinant DNA | | |
| pDONR223-DGKK | Addgene | Cat# 23487 |
| pCSF107mT-GATEWAY-3'-FLAG | Addgene | Cat# 67619 |
| pCDNA3-FLAG-DGKA (rat) | provided by Harris Lab at UVa | N/A |
| pCMV-Tag2B-FLAG-DGKQ (human) | provided by Harris Lab at UVa | N/A |
| pcDNA3-DGKE-3xFlag (human) | provided by Harris Lab at UVa | N/A |
| pCMV-SPORT6-HA-DGKZ (human) | provided by Harris Lab at UVa | N/A |
| Software and Algorithms | | |
| In-gel/in-blot fluorescence scanning and normalization; Image Lab software | Bio-Rad | http://www.bio-rad.com/en-us/product/image.lab.software |
| MS1 and MS2 file conversion; RawConverter | RawConverter | http://fields.scripps.edu/rawconv/ |
| MS data search algorithm; ProLuCID | Integreated Proteomics Applications (PV2) | http://www.integratedproteomics.com |
| MS data analysis; Skyline-daily | MacCross Lab Software | https://skyline.ms/project/home/software/Skyline/begin.view |
| Sequence alignment software; Clustal Omega | EMBL-EBI | http://www.ebi-ac.uk/Tools/msa/custalo/ |

Cell Culture

HEK293T cells were cultured in DMEM with 10% FBS (U.S. Source, Omega Scientific) and 1% L-glutamine (Thermo Fisher Scientific) in 10 cm² plates. SILAC HEK293T cells were cultured in DMEM for SILAC(Fisher Scientific) supplemented with 10% dialyzed FBS(Omega Scientific) and either 'Light' $^{12}C$, $^{14}N$-labeled lysine and arginine or 'Heavy' $^{13}C$, $^{15}N$-labeled lysine and arginine (100 μg/mL) in 10 cm² plates. Light or heavy amino acids were incorporated for at least 5 passages prior to utilizing SILAC HEK293T cells for experiments. All cells were grown to ~80% confluency in a 37° C. incubator with 5% $CO^2$.

Transient Transfection.

Recombinant DGK proteins were produced by transient transfection of HEK293T cells with recombinant DNA. pDONR223-DGKK was a gift from William Hahn & David Root (Addgene plasmid #23487). pCSF107mT-GATEWAY-3'-FLAG was a gift from Todd Stukenberg (Addgene plasmid #67619). pCSF107mT-DGKK-FLAG construct was generated by recombination of the Addgene plasmids using the Gateway cloning system (Invitrogen). All other vectors were gifted to Dr. Kevin Lynch (University of Virginia, School of Medicine) by Dr. Kaoru Goto (Yamagata University, School of Medicine) and Dr. Fumio Sakane (Chiba University) and were kindly shared with us: pcDNA3-FLAG-DGKA (rat), pCMV-Tag2B-FLAG-DGKQ (human), pcDNA3-DGKE-3xFlag (human), and pCMV-SPORT6-HA-DGKZ (human). HEK293T cells were plated at a concentration of 400,000 cells in complete DMEM and grown to 50-60% confluency. A polyethyleneimine (PEI) stock solution was prepared (1 mg/mL, pH 7.4) and filter sterilized. Serum-free DMEM (600 µL) was mixed gently with 2.6 µg DNA and 20 µL of sterile PEI (1 mg/mL, pH 7.4) in a sterile microfuge tube. Mixtures were incubated for 30 min at 25° C. The mixture was then added drop-wise to each 10 cm$^2$ plate, rocked back and forth to mix, and placed back in the incubator. Cell pellets were harvested after two full days of growth, snap-frozen in liquid $N_2$, and stored at −80° C. until use. Recombinant proteins were produced by transient transfection in SILAC HEK293T cells using the procedure described above, except that cells were plated at a concentration of 1×10$^6$ cells per 10 cm$^2$ plate and grown to ~70% confluency prior to introducing transfection mixture.

Western Blot Analysis of Recombinant Protein Expression.

Cell lysates were separated via centrifugation at 100,000×g for 45 min at 4° C. Proteins separated by SDS-PAGE (7.5% polyacrylamide, TGX Stain-Free Mini Gel) at 150 V for 55 min. Gel transfers were performed using the Bio-Rad Trans-Blot Turbo RTA Midi Nitrocellulose Transfer Kit with a Bio-Rad Trans-Blot Turbo Transfer System (25V, 10 min). The nitrocellulose blot was then incubated in blocking solution (30 mL, 5% Milk in TBS-T (1.5 M NaCl, 0.25 M Tris pH 7.4 in dd$H_2$O)) for 1 h at 25° C. with gentle shaking. The blot was then transferred immediately to primary antibody solution (1:1,000 anti-FLAG or 1:10,000 anti-HA in TBS-T) and incubated overnight at 4° C. with gentle shaking. The blot was then rinsed 5 times for 5 min in TBS-T, transferred immediately into secondary antibody solution (1:10,000 anti-species DyLight 550 or DyLight 650 in TBS-T), and incubated for 1 h at 25° C. with gentle shaking. The blot was then rinsed 5 times for 5 min in TBS-T, transferred into dd$H_2$O, and imaged by in-blot fluorescence scanning on a ChemiDoc MP Imaging System.

Preparation of Cell Lysates for Gel-Based Chemical Proteomics

Cell pellets were resuspended in kinase buffer (Dulbecco's PBS (DPBS, Hyclone), 20 mM $MgCl_2$, EDTA-free protease inhibitors (Pierce)) and then lysed by sonication (3×1 sec pulse, 20% amplitude). The cell lysates were then subjected to centrifugation (100,000×g, 45 min at 4° C.) to isolate the cytosolic fraction in the supernatant and the membrane fraction as a pellet. The membrane pellet was resuspended in kinase buffer by sonication. For all further analyses, only the soluble (cytosolic) fraction was used to prevent the need for detergents, which have been shown to interfere with DGK activity (Yada et al., 1990). The only exception was experiments involving DGKE; recombinant DGKE protein was most prominently expressed in the membrane fraction and so this fraction was utilized to study DGKE enzyme (see FIG. 8). Protein concentrations were measured using the Bio-Rad DC protein assay. Samples were stored at −80° C. until use.

Gel-Based Chemical Proteomic Assay.

Proteome concentration was adjusted to 2 mg/mL in kinase buffer. Proteomes were first pre-treated with compound (0.6 µL, 50× stock in DMSO) mixed with gentle flicking, and incubated for min at 25° C. in a microfuge tube (30 µL reaction volume). Desthiobiotin ATP acyl phosphate nucleotide probe (0.5 mM in dd$H_2$O) was then added to each sample (0.6 µL, 10 µM final) and incubated for 30 min at 25° C. Reactions were then quenched with 10 µL of 4× SDS-PAGE loading buffer. Protein samples (15 µL) were loaded onto 4-20% TGX Stain-Free Protein Midi Gel and resolved by SDS-PAGE at 150V for 55 min. Proteins were then transferred to a nitrocellulose blot by Bio-Rad Trans-Blot Turbo Transfer System (25V, 10 min) to enhance sensitivity.

The nitrocellulose blot was then incubated in blocking solution (30 mL, 3% BSA in TBS-T) for 1 h at 25° C. with gentle shaking. The blot was then transferred immediately to antibody solution (30 mL, 5% BSA in dd$H_2$O with 0.1% Tween20 and 1:3000 Streptavidin DyLight 550) and incubated for 2 h at 25° C. with gentle shaking. The blot was then rinsed 5 times for 5 min in TBS-T, and then transferred into dd$H_2$O. The blot was then imaged by in-blot fluorescence scanning on a ChemiDoc MP Imaging System. Fluorescence intensity signals were normalized to total lane protein using the Bio-rad Stain Free imaging (Posch et al., 2013).

Preparation of Cell Lysates for ADP-Glo Assay

The ADP-Glo DAG phosphorylation substrate assay was adapted from Sato et al (Sato et al., 2013). Transfected HEK cells expressing recombinant FLAG-DGKA were harvested in DPBS and centrifuged at 1400×g for 3 min. Supernatant was removed and 1 mL Lysis Buffer (50 mM HEPES (pH 7.2), 150 mM NaCl, 5 mM $MgCl_2$, 1 mM DTT, 1 mM phenylmethysulfonyl chloride, Phosphatase Inhibitor Cocktail 2 (Sigma-Aldrich), and EDTA-Free Protease Inhibitor Mini Tablets (Pierce)) was added and cells re-suspended. Solutions were sonicated (3×1 sec pulse, 20% amplitude) and then centrifuged at 400×g for 5 min. Supernatant was separated and protein concentrations were measured using the Bio-Rad DC protein assay and diluted in Lysis Buffer as appropriate. Samples were stored at −80° C. until use.

ADP-Glo DAG Phosphorylation Substrate Assay.

Micelles were prepared from lipid stocks as follows: Reaction Buffer (50 mM MOPS (pH 7.4), 1 mM DTT, 100 mM NaCl, 20 mM NaF, and 1 µM $CaCl_2$)) was prepared in dd$H_2$O. From this stock, a solution of Reaction Buffer with 50 mM $MgCl_2$ and 1 mM ATP ('Reaction Initiator') and a solution of 0.3% Triton-X100 in Reaction Buffer ('Triton Buffer') were separately prepared. 1, 2-dioleoyl-sn-glycerol (DG) and 1,2-dioleoyl-sn-glycero-3-phospho-L-serine (DOPS) in chloroform were mixed and then dried under nitrogen. Triton Buffer was added to the dried lipids to a final concentration of 10 mM DG and 8 mM DOPS. This solution was incubated at room temperature for 5 min with gentle shaking, followed by sonication (3×1 sec pulse, 20% amplitude). The micelles were then diluted 4-fold in reaction buffer to yield the final micelle buffer. 1 mg of lysate was aliquoted into each well of a 96 well plate, followed by micelle buffer to a final volume of 20 µL. 19 µL of this mix was added to 1 µL of DMSO or inhibitor solution and incubated at 30° C. for 30 min. After incubation, 5 µL of reaction initiator was added to each well and mixed thoroughly, followed by aliquoting 5 µL of each reaction mixture to a 96-well half area black polystyrene plate and incubated at 30° C. for 30 min. At this point the procedure for the ADP-Glo™ assay (Promega) was performed. 5 µL of 'ADP-Glo Reagent' was added to each well, mixed thoroughly, and allowed to incubate at 25° C. for 40 min. Then 10 µL of the 'Kinase Detection Reagent' was added to each well, mixed thoroughly, and allowed to incubate at 25° C. for 40 min. Luminescence was measured with no filter and an integration time of 1 sec per well on a BMG Labtech CLARIOstar plate reader. Sample preparation for quantitative LC-MS analysis using ATP acyl phosphates.

Proteomes were diluted to 2 mg/mL in kinase buffer. The light and heavy proteomes (0.5 mg, 250 µL total reaction volume) were pre-treated with vehicle or compound, respectively (5 µL, DMSO (light) or 50× stock in DMSO (heavy)), mixed gently, and incubated at 25° C. for 30 min. Desthiobiotin ATP acyl phosphate nucleotide probe (0.5 mM in ddH$_2$O) was then added to each sample (5 µL, 10 µM final), mixed gently, and allowed to incubate at 25° C. for 30 min. After incubation, matched light and heavy proteomes were transferred and mixed in a 1:1 ratio in a two-dram vial containing 4:1:3 MeOH/CHCl$_3$/H$_2$O (2 mL MeOH, 500 µL CHCl$_3$, 1.5 mL H$_2$O) for extraction of proteins to remove excess probe, quickly vortexed, and centrifuged at 1,400×g for 3 min to pellet protein. Organic and aqueous layers were removed using a Pasteur pipette, and the protein pellet was transferred to a screw-top tube in 600 µL MeOH. A second extraction was performed by adding CHCl$_3$ (150 µL) and H$_2$O (600 µL) to each sample, vortexed, and centrifuged at 1,400×g for 3 min to pellet protein. Organic and aqueous layers were removed by pipetting, MeOH added to pellet (600 µL) and pellets were re-suspended by sonication (3×1 sec pulse, 20% amplitude) for a final extraction. Samples were then centrifuged at 17,000×g for 5 min to pellet protein and MeOH was removed by pipetting. The pellets were re-suspended in 10 M urea/25 mM ammonium bicarbonate (500 mL), brought to a final volume of 1 mL with 25 mM ammonium bicarbonate, reduced with 10 mM DTT for 15 min at 65° C., allowed to cool, and then alkylated with 40 mM iodoacetamide for 30 min at 25° C. in the dark. To desalt the samples, each was transferred to a two-dram glass vial, and to the vial 4:1:2 MeOH/CHCl$_3$/H$_2$O (2 mL MeOH, 500 µL CHCl$_3$, 1 mL H$_2$O) was added. The vials were vortexed quickly, spun at 1,400×g for 3 min to pellet protein, and aqueous and organic layers were removed using a Pasteur pipette. The resulting protein pellet was transferred to a screw-top tube in 600 µL MeOH, and then CHCl$_3$ (150 µL) and H$_2$O (600 µL) were added to extract protein a second time. The samples were vortexed quickly, centrifuged at 1,400×g to pellet protein, and the aqueous and organic layers were removed by pipetting. Resulting protein pellet was suspended in MeOH (600 µL) via sonication (3×1 sec pulse, 20% amplitude), centrifuged at 17,000×g for 5 min to pellet protein, and MeOH removed by pipetting. Protein pellets were then re-suspended in 25 mM ammonium bicarbonate (500 µL) and digested with 7.5 µg Trypsin/Lys —C(Promega, 15 µL, 0.5 µg/µL) for 3 h at 37° C. Avidin-agarose beads (Thermo Scientific Pierce, 100 µL aliquot per sample) were washed three times by adding 10 mL DPBS, centrifuged at 1,400×g for 1 min, and decanting. This wash step was repeated for a total of 3 times. Digested protein samples were mixed with washed avidin beads (100 µL) and brought to a volume of 5.5 mL with DPBS in a 15 ml conical and rotated for 1 h to enrich samples for the covalent desthiobiotin modification. The beads were washed with 25 mM ammonium bicarbonate (3× with 10 mL, centrifuge at 1,400×g for 3 min, decant) and then H$_2$O (3× with 10 mL, centrifuge at 1,400×g for 3 min, decant). Washed beads were then transferred to a low-bind microfuge tube, centrifuged at 1,400×g for 3 min, allowed to rest for 1 min to settle beads, and then excess H$_2$O was removed carefully using a gel-loading pipette tip. To elute peptides, 100 µL of elution buffer (50% acetonitrile, ACN; 0.1% formic acid) was added to each sample and incubated for 3 min. Beads were spun down at 1,400×g for 3 min, allowed to rest for 1 min to settle beads, and then 75 µL of peptide-containing supernatant was removed carefully using a gel-loading pipette tip and transferred to a new low bind centrifuge tube. This step was repeated two more times with 75 µL of elution buffer and all eluent were collected into the same centrifuge tube (~225 µL total). Peptides were dried on a speed vacuum, resulting peptide samples acidified in 5% (v/v) formic acid, and stored at −80° C. until analysis.

LC-MS/MS Analysis of SILAC Samples

The peptide samples were analyzed by liquid chromatography-mass spectrometry. An integrated autosampler-LC (Ultimate 3000 RSLC nanoSystem, Dionex) was used to load the peptides onto a trap column (Nano-Trap, Thermo Scientific, 2 cm, 5 µm C18) and washed for 2 minutes with 1% B (80% ACN, 1% formic acid). The peptides were eluted from the trap column and through a homemade nanocapillary analytical column (20 cm, 5 µm C18 packed in 360 µm o.d.×75 µm i.d. fused silica), with an integrated electrospray tip, using a 180 min 1-95% reverse-phase LC gradient (A: 0.1% formic acid; B: 80% ACN, 0.1% formic acid) with the following parameters: 0-2 min 1% B, 400 nL/min; 2-144 min to 95% B, 300 nL/min; 144.1-180 min 1% B, 400 nL/min. The eluting peptides were electrosprayed into an Orbitrap Q Exactive Plus mass spectrometer (Thermo Scientific), which was operated with a top 10 data-dependent acquisition method that consisted of one full MS1 scan (375-1,500 m/z) followed by 10 MS2 scans of the most abundant ions recorded in the MS1 scan. For recombinant DGKE samples, a data-independent parallel reaction monitoring (PRM) method was used to detect DGKE peptides. One full MS1 scan (375-1,500 m/z) was followed by MS2 scans of targeted parent ions from a curated inclusion list (DGKE: EKAPSLFSSR, +2 charge state, 659.3617 m/z (light), 668.3729 m/z (heavy), 103.00-110.00 min). Data analysis was accomplished using the IP2 (Integrated Proteomics Applications) software package, in which RawConverter was used to generate searchable MS1 and MS2 data from the .raw file followed by using the ProLuCID algorithm to search the data against a modified human protein database (UniProt human protein database with rat DGKs, angiotensin I and vasoactive intestinal peptide standards; 40,660 proteins) with the following parameters: static carbamidomethyl modification of cysteine (+57.0142 Da), differential modifications of oxidized methionine (+15.9949 Da) and desthiobiotin-labeled lysine residues (+196.1212 Da), added masses of the SILAC "heavy"-labeled amino acids (+10.0083 Da for R, +8.0142 Da for K), and trypsin enzyme specificity with 2 missed cleavages. The resulting MS2 spectra matches were assembled into protein identifications and filtered using. 30 DTASelect 2.0 using the —mass, —modstat, and —trypstat options with a 1% peptide FDR. mzIdent files corresponding to searches were generated in IP2-Integrated Proteomics Pipeline, mzXML spectra data was extracted from the raw file using RawConverter, and uploaded into Skyline-daily (Schilling et al., 2012) to determine SILAC ratios (SR) of light/heavy (vehicle/compound treated) peptides. Peptides used for analysis were assessed for quality in Skyline by the following criteria: 35 isotope dot-product (iDOTP) ≥0.8, ratio dot-product (rDOTP) ≥0.8, and singletons defined by L/H ratios >20 were set to 20. Dot-product values are measures of similarity between the precursor peak area and expected isotope distribution (iDOTP) and between the light and heavy peak area (rDOTP) as calculated in Skyline and described by Schilling et al (Schilling et al., 2012). Probe-modified peptides that met these criteria were manually inspected and integrated. Peptide ratios reported were normalized to DMSO/DMSO peptide ratios to account for potential variations in mixing and sample preparations. Additionally, reported DGK and FER peptides were verified by manual inspection of the raw data (MS1 and MS2).

Sequence Alignments and Generation of Sequence Logos.

Lipid kinase sequences were obtained from Uniprot (http://www.uniprot.org/) and aligned using Clustal Omega (Goujon et al., 2010; Sievers et al., 2011). Sequence logos shown in FIG. 5 were generated with WebLogo (Crooks et al., 2004; Schneider and Stephens, 1990) (weblogo.threeplusone.com).

DgkB Monomer Molecular Model and Alignment.

PDB model 2QV7 visualized and colored using PyMol software. Partial Structure-Aided Sequence Alignment completed as described previously (Miller et al., 2008) and added to FIG. 11 using GIMP software package.

Statistical analysis and determination of $IC_{50}$ values.

The percentage of enzyme activity remaining was determined by comparing integrated band intensities or luminescence of inhibitor- with DMSO-treated samples for gel-based chemical proteomic or ADP-glo assays, respectively. For both chemical proteomic and ADP-glo methods, non-linear regression analysis was used to determine the $IC_{50}$ values from a dose-response curve generated using GraphPad Prism. Data are shown as mean #s.e.m. Determination of significance was performed by one-way ANOVA. All statistical analyses were performed using GraphPad Prism.

Results

ATP Acyl Phosphates Function as Activity-Based Probes of DGKα.

To test whether ATP acyl phosphates (FIG. 2A) can be used to profile DGK activity, the strategy was to transiently express DGKs and test recombinant enzymes directly in cell proteomes without the need for protein purification. It was reasoned that this approach would mitigate challenges with detection due to differences in endogenous DGK levels while permitting analyses on a proteomic scale. The initial studies focused on the alpha isoform (DGKα, FIG. 1B) given the availability of inhibitors and matching negative control compounds (Boroda et al., 2017) for the proof-of-principle experiments (FIG. 2B). Overexpression of recombinant FLAG-tagged DGKα was confirmed by western blot (FIG. 8) and used published DAG phosphorylation substrate assays (Sato et al., 2013) to measure recombinant DGKα activity (FIG. 9A). Significantly higher DAG phosphorylation activity (~6-fold on average) was observed in DGKα-compared with mock-transfected or heat-denatured proteomes (FIG. 9B). Furthermore, recombinant DGKα activity was blocked in a concentration-dependent manner using the DGKα inhibitor ritanserin (Boroda et al., 2017) compared with dimethyl sulfoxide (DMSO) vehicle-treated controls ($IC_{50=25}$ μM, FIG. 3A). Since ritanserin exhibits 5-HT2 receptor (5-HT2R) inhibitory activity (Barone et al., 1986), another 5-HT2R antagonist ketanserin was included (Boroda et al., 2017) (FIG. 2B) to control for non-specific effects in the substrate assay. Ketanserin showed negligible activity against DGKα in the substrate assay, confirming the use of ritanserin and ketanserin as paired probes (i.e. DGK active and inactive inhibitors, respectively, at 100 μM; FIG. 9B) suitable for testing in the chemical proteomics assay.

Next, it was determined whether one could use desthiobiotin-tagged, ATP acyl-phosphates (Patricelli et al., 2011; Patricelli et al., 2007) as a surrogate chemical proteomic assay for measuring recombinant DGKα activity in cell proteomes (FIG. 2A). ATP acyl-phosphate probes enable global profiling of kinase activities by covalent attachment of reporter tags to conserved lysine residues in the ATP binding site of a wide range of kinases as well as other ATP-binding proteins (Patricelli et al., 2011; Patricelli et al., 2007). Initially, gel-based profiling experiments were preformed to allow rapid optimization of probe labeling parameters (FIG. 10A). In brief, DGKα-HEK293T soluble lysates were reacted with the ATP acyl-phosphate probe, desthiobiotin-modified proteins separated by SDS-PAGE, transferred to a nitrocellulose membrane, and probe-modified proteins detected using a fluorescently-labeled streptavidin. Concentration dependent labeling of a ~80 kDa fluorescent band in DGKα- but not mock-transfected HEK293T proteomes was observed (FIG. 10B). It was confirmed by western blot that differences in fluorescence signals in the probe binding assay were not due to expression levels of recombinant DGKα (Bottom panel, FIG. 10B).

From these studies, experimental conditions were identified where ATP acyl-phosphate labeling of DGKα was not saturating to allow competitive profiling of reversible inhibitors (Adibekian et al., 2012) (10 UM ATP probe, 30 min; FIG. 10C). Using these kinetically-controlled conditions, it was shown that pretreatment with ritanserin but not ketanserin resulted in concentration-dependent blockade of probe labeling ($IC_{50=57}$ μM, FIG. 3B and Figure S10D). The non-selective DGK inhibitors, R59949 (de Chaffoy de Courcelles et al., 1989) and R59022 (de Chaffoy de Courcelles et al., 1985), were analyzed to show that the gel activity assay can be used to generally profile inhibitor activity against DGKα (FIG. 10E). Finally, it was shown that treatment with free ATP (1 mM) resulted in global reductions in fluorescent protein signals (FIG. 3C). These results support specific detection of probe labeling events occurring in the ATP binding site of recombinant DGKα as well as other native proteins detected in HEK293T cell proteomes. In all of the probe-labeling studies, changes in fluorescent signals in compound-treated samples were not due to differences in DGKα protein levels as confirmed by western blot analysis (Bottom panels; FIG. 3C, FIGS. 10D and E). Collectively, the comparable potency values determined using substrate-(FIG. 3A) versus chemical proteomic-assays (FIG. 3B) demonstrate that ATP acyl phosphates are capable of measuring authentic DGKα activity with the advantage of enabling rapid assessment of compound activity across ATP-binding sites detected in native cell proteomes (FIG. 3C).

Mapping the ATP Binding Site of DGKα Using Quantitative Chemical Proteomics.

Results from gel profiling analyses demonstrated the probe binding of DGKα is competed by ATP substrate. While suited for rapid screening, gel-based chemical proteomic assays do not provide information on site of binding of compounds. Thus, a liquid chromatography-mass spectrometry (LC-MS) assay was implemented to discover the ATP binding site(s) of DGKα. For these studies, DGKα was overexpressed in isotopically light and heavy amino acid-labeled HEK293T cells to enable quantitative LC-MS by stable isotope labeling with amino acids in cell culture (SIL.AC(Mann, 2006), FIG. 4A). In brief, light and heavy DGKα-HEK293T lysates were treated differentially with DMSO vehicle or free ATP (1 mM) respectively, prior to addition of ATP acyl phosphate to label active site lysines. After probe labeling, light and heavy proteomes were combined, digested with trypsin protease, and desthiobiotin-modified peptides were enriched by avidin affinity chromatography and analyzed by LC-MS/MS to identify and quantify isotopically tagged active-site peptides from DGKα (FIG. 4A, see Materials and Methods for more details).

Using the quantitative chemical proteomics assay, two probe-labeled peptides were identified that were highly competed with ATP treatment as determined by SILAC ratios (SR) of MS1 chromatographic peak areas >5 in DMSO/ATP comparisons (FIG. 4B and Table 1 and 1A. All peptides reported met quality control criteria and were observed in 2 biological replicates (see. Materials and Methods for more details). The sites of labeling for probe-modified peptides of DGKα were confirmed by identifying ions corresponding to peptide fragments that contain the modified lysine residue in MS2 spectra (red asterisk, FIG. 4B). Both ATP-sensitive peptides are located within the predicted catalytic domain, albeit at different subdomain regions (K377-DAGKc, SR=16.3; K539-DAGKa, SR=16.4; FIG. 4B). Comparison of these peptide sequences with ATP-binding motifs found in protein kinases (Hanks et al., 1988; Sakane et al., 1990) revealed no apparent homology, supporting previous speculation that DGKs mediate ATP binding through a non-canonical binding motif (Schaap et al., 1994). Closer inspection of the DAGKc peptide did reveal homology with ATP binding sites of DgkB from *S. aureus*, and placement of K377 at the homologous residue in the bacterial DGK crystal structure (threonine 12) positions this lysine in vicinity of phosphate groups of ADP (Miller et al., 2008) (FIG. 11). The second ATP-sensitive peptide (K539, FIG. 4B) is located in the poorly annotated DAGKa subdomain that has not been implicated in ATP binding in DGKα or any other DGK isoform. These results help explain previous findings from other groups showing that C-terminal truncations (which remove the DAGKa subdomain) result in impaired DGK catalytic activity (Los et al., 2004).

TABLE 1

(SEQ ID NOs: 17-68)

| Kinase name | Peptide | Labeling site | Uniprot Accession | Annotation | Ratios ATP | Ketan- serin | Ritan- serin | RF001 |
|---|---|---|---|---|---|---|---|---|
| Recombinant DGKs | | | | | | | | |
| DGKA | QGLSCNLCK YIVHDHCAM K | C1 | P51556 | Diacylglycerol kinase alpha [*Rattus norvegicus* (Rat)] | 2.4 | 1.4 | 7.0 | 12.6 |
| DGKA | IEPVSNTHPL LVFINPKSGG K | DAGKc | P51556 | Diacylglycerol kinase alpha [*Rattus norvegicus* (Rat)] | 16.3 | 1.2 | 2.0 | 1.7 |
| DGKA | YPEKFNSR | DAGKa | P51556 | Diacylglycerol kinase alpha [*Rattus norvegicus* (Rat)] | 16.4 | 1.3 | 7.0 | 9.1 |
| DGKK | NKMWYGLL GTK | DAGKa | Q5KSL6 | Diacylglycerol kinase kappa [*Homo sapiens* (Human)] | 15.0 | 0.2 | 0.7 | 1.6 |
| DGKE | EKAPSLFSSR | DAGKa | P52429 | Diacylglycerol kinase epsilon [*Homo sapiens* (Human)] | 2.6 | 1.3 | 1.0 | 0.7 |
| DGKZ | CAACKIVVH TPCIEQLEK | C1 | Q13574 | Diacylglycerol kinase zeta [*Homo sapiens* (Human)] | 3.1 | 1.3 | 1.4 | 1.1 |
| DGKZ | SGGNQGAKII QSFLWYLNP R | DAGKc | Q13574 | Diacylglycerol kinase zeta [*Homo sapiens* (Human)] | 2.9 | 1.5 | 1.2 | 0.9 |
| DGKZ | EANPEKFNS R | DAGKa | Q13574 | Diacylglycerol kinase zeta [*Homo sapiens* (Human)] | 16.7 | 1.4 | 1.8 | 1.1 |
| DGKQ | KTCGSSDVL AGVR | C1 | P52824 | Diacylglycerol kinase theta [*Homo sapiens* (Human)] | 3.6 | 0.9 | 1.3 | 0.7 |
| DGKQ | LPPDSCPLLV FVNPKSGGL K | DAGKc | P52824 | Diacylglycerol kinase theta [*Homo sapiens* (Human)] | 7.6 | 1.2 | 1.1 | 0.9 |
| DGKQ | EEEPGKFTSR | DAGKa | P52824 | Diacylglycerol kinase theta [*Homo sapiens* (Human)] | 14.4 | 1.1 | 1.4 | 1.2 |
| Native kinases in HEK293T | | | | | | | | |
| AAPK1/AAPK2 | DLKPENVLL DAHMNAK | Lys2 | Q13131 | 5'-AMP-activated protein kinase catalytic subunit alpha-1 [*Homo sapiens* (Human)] | 9.1 | 1.4 | 2.4 | 1.1 |

TABLE 1-continued (SEQ ID NOs: 17-68)

| Kinase name | Peptide | Labeling site | Uniprot Accession | Annotation | Ratios | | | |
|---|---|---|---|---|---|---|---|---|
| | | | | | ATP | Ketan-serin | Ritan-serin | RF001 |
| BRAF | DLKSNNIFLH EDLTVK | Lys2 | P15056 | B-Raf proto-oncogene serine/threonine-protein kinase [Homo sapiens (Human)] | >20 | 1.6 | 1.8 | 1.1 |
| CDK1 | DLKPQNLLID DKGTIK | Lys2 | P06493 | Cell division control protein 2 homolog [Homo sapiens (Human)] | 8.4 | 1.4 | 2.4 | 1.1 |
| CDK2 | DLKPQNLLIN TEGAIK | Lys2 | P24941 | Cell division protein kinase 2 [Homo sapiens (Human)] | >20 | 1.6 | 2.9 | 0.7 |
| CDK5 | DLKPQNLLIN R | Lys2 | Q00535 | Cell division protein kinase 5 [Homo sapiens (Human)] | 10.7 | 1.3 | 1.9 | 1.1 |
| CHK2 | VAIKIISK | Lys1 | O96017 | Serine/threonine-protein kinase Chk2 [Homo sapiens (Human)] | >20 | 1.6 | 2.2 | 0.2 |
| CSK | VSDFGLTKE ASSTQDTGK LPVK | ACT | P41240 | Tyrosine-protein kinase CSK [homo sapiens (Human)] | 15.8 | 1.2 | 1.8 | 1.1 |
| E2AK2 | DLKPSNIFLV DTK | Lys2 | P19525 | Interferon-induced, double-stranded RNA-activated protein kinase [Homo sapiens (Human)] | >20 | 1.3 | 2.8 | 1.2 |
| FER | TSVAVKTCK EDLPQELK | Lys1 | P6591 | Proto-oncogene tyrosine-protein kinase FER n = 2 Tax = Homo sapiens RepID = FER_HUMAN | 19.3 | 1.4 | 7.9 | 1.2 |
| IRAK1 | AIQFLHQDSP SLIHGDIKSS NVLLDER | Lys2 | P51617 | Interleukin-1 receptor-associated kinase 1 [Homo sapiens (Human)] | 14.7 | 1.4 | 2.6 | 2.2 |
| KCC1D | LFAVKCIPK | Lys1 | Q8IU85 | Calcium/calmodulin-dependent protein kinase type 1D [Homo sapiens (Human)] | >20 | 1.5 | 2.3 | 1.1 |
| KCC2D | IPTGQEYAA KIINTK | Lys1 | Q13557 | Calcium/calmodulin-dependent protein kinase type II delta chain n = 2 Tax = Euarchontoglires RepID = KCC2D_HUMAN | 10.3 | 1.5 | 2.3 | 1.2 |
| KCC2G | TSTQEYAAKI INTK | Lys1 | Q13555 | Calcium/calmodulin-dependent protein kinase type II gamma chain [Homo sapiens (Human)] | 14.7 | 1.5 | 2.7 | 1.6 |
| KS6A1 | LTDFGLSKE AIDHEK | ACT | Q15418 | Ribosomal protein S6 kinase alpha 1 [Homo sapiens (Human)] | 19.5 | 1.4 | 2.1 | 1.3 |
| KS6A1/KS6A2/ KS6A3 | DLKPENILLD EEGHIK | Lys2 | Q15418 | Ribosomal protein S6 kinase alpha 1 [Homo sapiens (Human)] | 19.4 | 1.4 | 2.0 | 1.2 |
| KS6A4/KS6A5 | VLGTGAYGK VFLVR | ATP Loop | O75676 | Ribosomal protein S6 kinase alpha 4 [Homo sapiens (Human)] | >20 | 1.3 | 2.2 | 1.1 |

TABLE 1-continued (SEQ ID NOs: 17-68)

| Kinase name | Peptide | Labeling site | Uniprot Accession | Annotation | ATP | Ketan-serin | Ritan-serin | RF001 |
|---|---|---|---|---|---|---|---|---|
| KS6B1 | DLKPENIML NHQGHVK | Lys2 | P23443 | Ribosomal protein S6 kinase 1 (EC 2.7.1.37) (S6K)(S6K1)(70 kDa ribosomal protein S6 kinase 1) (p70 S6 kinase alpha) (p70(S6K)-alpha) [Homo sapiens (Human)] | >20 | 1.2 | 1.3 | 1.0 |
| KS6B2 | DLKPENIMLS SQGHIK | Lys2 | Q9UBS0 | Ribosomal protein S6 kinase 2 [Homo sapiens (Human)] | 19.2 | 1.1 | 1.4 | 1.7 |
| LATS1 | ALYATKTLR | Lys1 | O95835 | Serine/threonine-protein kinase LATS1 [Homo sapiens (Human)] | >20 | 1.2 | 1.8 | 1.4 |
| M3K2/M3K3 | DIKGANILR | Lys2 | Q9Y2U5 | Mitogen-activated protein kinase kinase kinase 2 n = 3 Tax = Homo sapiens RepID = M3K2_HUMAN | 19.2 | 1.1 | 1.2 | 1.0 |
| M3K4 | DIKGANIFLT SSGLIK | Lys2 | Q9Y6R4 | Mitogen-activated protein kinase kinase kinase 4 [Homo sapiens (Human)] | 6.8 | 1.2 | 1.9 | 0.8 |
| M4K3 | DIKGANILLT DNGHVK | Lys2 | Q8IVH8 | Mitogen-activated protein kinase kinase kinase 3 [Homo sapiens (Human)] | 14.2 | 1.4 | 1.8 | 1.1 |
| M4K4/MINK1/ TNIK | DIKGQNVLL TENAEVK | Lys2 | O95819 | Mitogen-activated protein kinase kinase kinase 4 [Homo sapiens (Human)] | >20 | 1.3 | 1.8 | 1.1 |
| M4K5 | NVHTGELAA VKIIK | Lys1 | Q9Y4K4 | Mitogen-activated protein kinase kinase kinase 5 [Homo sapiens (Human)] | >20 | 1.3 | 2.4 | 0.9 |
| M4K5 | DIKGANILLT DHGDVK | Lys2 | Q9Y4K4 | Mitogen-activated protein kinase kinase kinase 5 [Homo sapiens (Human)] | >20 | 1.3 | 1.9 | 1.3 |
| MARK3/MARK4 | EVAVKIIDK | Lys1 | P27448 | MAP/microtubule affinity-regulating kinase 3 [Homo sapiens (Human)] | >20 | 1.4 | 2.0 | 1.1 |
| MP2K1/MP2K2 | DVKPSNILV NSR | Lys2 | Q02750 | Dual specificity mitogen-activated protein kinase 1 n = 4 Tax = Eutheria RepID = MP2K1_HUMAN | >20 | 1.3 | 1.9 | 0.9 |
| MP2K3 | DVKPSNVLI NK | Lys2 | P46734 | Dual specificity mitogen-activated protein kinase 3 [Homo sapiens (Human)] | 19.1 | 1.4 | 1.7 | 1.2 |
| MP2K4 | DIKPSNILLD R | Lys2 | P45985 | Dual specificity mitogen-activated protein kinase 4 [Homo sapiens (Human)] | >20 | 1.3 | 1.6 | 0.9 |
| MP2K6 | HVPSGQIMA VKR | Lys1 | P52564 | Dual specificity mitogen-activated protein kinase 6 [Homo sapiens (Human)] | >20 | 1.4 | 2.2 | 1.1 |
| NEK3 | SKNIFLTQNG K | ACT | P51956 | Serine/threonine-protein kinase Nek3 [Homo sapiens (Human)] | >20 | 1.0 | 2.2 | 1.0 |

TABLE 1-continued (SEQ ID NOs: 17-68)

| Kinase name | Peptide | Labeling site | Uniprot Accession | Annotation | ATP | Ketanserin | Ritanserin | RF001 |
|---|---|---|---|---|---|---|---|---|
| PAN3 | VMDPTKILITGK | ATP | Q58A45 | PAB-dependent poly(A)-specific ribonuclease subunit [Homo sapiens (Human)] | >20 | 1.3 | 1.8 | 1.3 |
| PI42C | FKEYCPQVFR | C2 | Q8TBX8 | Phosphatidylinositol-5-phosphate 4-kinase type-2 gamma n = Tax = Homo sapiens RepID = PI42C_HUMAN | 6.9 | 1.2 | 1.7 | 0.8 |
| PLK1 | CFEISDADTKEVFAGKIVPK | Lys1 | P53350 | Serine/threonine-protein kinase PLK1 [Homo sapiens (Human)] | 12.2 | 1.0 | 1.5 | 0.9 |
| RAF1 | DMKSNNIFLHEGLTVK | Lys2 | P04049 | RAF proto-oncogene serine/threonine-protein kinase [Homo sapiens (Human)] | >20 | 1.4 | 3.9 | 2.1 |
| SLK | DLKAGNILFTLDGDIK | Lys2 | Q9H2G2 | CTCL tumor antigen se20-9 [Homo sapiens (Human)] | >20 | 1.3 | 3.0 | 1.5 |
| SMG1 | DTVTIHSVGGTITILPTKTKPK | ATP | Q96Q15 | Serine/threonine-protein kinase SMG1 n = 4 Tax = Homo sapiens RepID = SMG1_HUMAN | 15.9 | 1.3 | 1.7 | 1.0 |
| STK10 | DLKAGNVLMTLEGDIR | Lys2 | O94804 | Serine/threonine-protein kinase 10 [Homo sapiens (Human)] | 7.4 | 1.3 | 1.7 | 1.1 |
| STK3/STK4 | DIKAGNILLNTEGHAK | Lys2 | Q13188 | Serine/threonine-protein kinase 3 [Homo sapiens (Human)] | >20 | 1.2 | 1.6 | 0.9 |
| STK38 | DTGHVYAMKILR | Lys1 | Q15208 | Serine/threonine-protein kinase 38 [Homo sapiens (Human)] | 5.2 | 1.3 | 2.0 | 1.4 |
| ULK3 | EVVAIKCVAK | Lys1 | Q6PHR2 | Unc-51-like kinase 3 [Homo sapiens (Human)] | >20 | 2.3 | 1.8 | 1.4 |

TABLE 1A (SEQ ID NOs: 69-78)

| Isoform | Uniprot Accession | Peptide sequence |
|---|---|---|
| DAGKc subdomain | | |
| DGKA | P51556 | PLLVFINPKSGGKQGQSVLWKFQYILNP |
| DGKK | Q5KSL6 | PLLIFINSKSGDHQGIVFLRKFKQYLNP |
| DGKE | P52429 | PLIILANSRSGTNMGEGLLGEFRILLNP |
| DGKZ | Q13574 | PLLVFVNPKSGGNQGAKIIQSFLWYLNP |
| DGKQ | P52824 | PLLVFVNPKSGGLKGRDLLCSFRKLLNP |
| DAGKa subdomain | | |
| DGKA | P51556 | FHLMREKYPEKFNSRMKNKLWYLEFAT |
| DGKK | Q5KSL6 | FNTRRDEHPGQYNSRLKNKMWYGLLGT |
| DGKE | P52429 | FHAHREKAPSLFSSRILNKAVYLFYGT |
| DGKZ | Q13574 | FHESREANPEKFNSRFRNKMFYAGTAF |
| DGKQ | P52824 | FHQAREEEPGKFTSRLHNKGVYVRVGL |

Finally, a probe-modified peptide located in the first C1 domain of DGKα was identified (K237, FIG. 4B). The C1 site was competed with ATP treatments (K237, SR=2.4, ~58% inhibition; FIG. 4B and Table 1 and Table 1A but with lower potency compared with probe-modified peptides from DAGKc and DAGKa subdomains (~94% competition with ATP). The difference in sensitivity to ATP competition at C1 versus DAGKc/DAGKa suggests that the latter sites largely mediate ATP binding of DGKα. The partial sensitivity of C1 to ATP competition suggests the existence of a distinct binding site in the C1 domain that can bind ATP probe separate from interactions at the DAGKc/DAGKa sites (FIG. 4C). In summary, the LC-MS findings provide evidence that ATP acyl phosphate probes can map important binding regions of DGKα domains to reveal ATP (DAGKc/DAGKa) and other ligand binding sites (C1) important for mediating catalytic functions.

Chemical Proteomic Profiling of the DGK Superfamily Using ATP Acyl Phosphates.

Next, it was sought to expand the chemical proteomics analysis to other DGK subtypes to identify conserved and distinguishing features of active sites in comparison with type 1 DGKα. For these studies, a representative member from each of the DGK subtypes was chosen to test: kappa (DGKK (Imai et al., 2005)), type 2; epsilon (DGKE (Tang et al., 1996)), type 3; zeta (DGKε (Goto and Kondo, 1996)), type 4; and theta (DGKθ (Houssa et al., 1997)), type 5 (FIG. 1B). Recombinant DGKs were transiently transfected in light and heavy HEK293T cells, protein overexpression confirmed by western blot (FIG. 8), and recombinant lysates subjected to quantitative chemical proteomics (FIG. 4A). The identified probe-modified peptides for each DGK isoform and their corresponding sensitivities to ATP competition are listed in Table 1 and 1A Akin to DGKα, probe-modified peptides in C1, DAGKc, and DAGKa binding sites of DGKS and DGKθ were identified (FIG. 5A). Treatment with free ATP resulted in potent competition at DAGKc (K596, SR=7.6) and DAGKa (K768, SR=14.4) sites within the catalytic domain of DGKθ (FIG. 5A and Table 1 and 1A. Similar inhibition profiles were observed for DGKζ with the exception of a lower sensitivity to ATP competition at the DAGKc (K500, SR=2.9) compared with DAGKa site (K662, SR=16.7, FIG. 5A and Table 1 and 1A. Probe-modified peptides corresponding to C1 domains of both DGKS (K323) and DGK0 (K202) showed moderate competition with ATP (SR ~3 for both isoforms, FIG. 5A and Table 1 and 1A. Of the remaining subtypes, a single probe-modified peptide in the DAGKa subdomain of DGKK and DGK& were identified that were competed with ATP with high (K892, SR=15.0) or moderate inhibition (K392, SR=2.6; FIG. 5A and Table 1 and 1A, respectively. Based on ATP sensitivity, the findings position the primary ATP binding site within the DAGKa subdomain of type 2 (DGKκ), 3 (DGKε), and 4 (DGKζ) enzymes. Similar to DGKα, type 5 DGK0 likely requires both DAGKa and DAGKc regions for ATP substrate binding.

Multiple sequence alignments and sequence logo analysis (Crooks et al., 2004; Schneider and Stephens, 1990) were performed to identify a potential DGK-specific ATP binding motif. ATP-competed peptide sequences identified in the LC-MS analyses (Table 1 and 1A were used to discover potential regions of sequence conservation across all 5 DGK subtypes tested. The analyses identified clusters of amino acid conservation in regions that contained probe-modified lysines within both DAGKc (positions 7-17, FIG. 5B) and DAGKa subdomains (positions 7-19, FIG. 5C). The results were used to determine whether DGKs are probe-labeled at conserved lysines in the active site, which would provide preliminary evidence of a common ATP binding orientation. Closer inspection of the data revealed that the lysine showing highest conservation in the DAGKc motif was also probe modified with the highest frequency (position 9, FIG. 5B). In contrast, the correlation between conserved lysines and frequency of probe modifications at these sites was less clear in the DAGKa motif. For example, probe modification of the lysine with highest conservation (position 19) was only observed in the DGKK active site peptide (FIG. 5C). The identification of probe modifications at both conserved (DAGKc) and non-conserved lysines (DAGKa) in the DGK ATP binding site is different from protein kinases, which are probe modified largely at conserved lysines in the ATP binding site (Patricelli et al., 2007).

Inhibitor profiling to determine ritanserin binding mode and selectivity.

Next it was asked whether one could use quantitative chemical proteomics to determine the binding mode and selectivity of inhibitors against DGK isoforms. Ritanserin was originally tested in the clinic as a serotonin receptor antagonist for treatment of psychiatric disorders (Barone et al., 1986) and has recently generated interest as a lead DGKα inhibitor for drug repurposing to treat cancer . . . (Boroda et al., 2017; Purow, 2015). DGKα-HEK293T soluble proteomes were treated with ritanserin or ketanserin (100 μM compounds, FIG. 2B) followed by labeling with ATP acyl phosphate and quantitative chemical proteomics analysis (FIG. 4A). Ritanserin concentrations were chosen to provide ~70% blockade of DGKα activity as determined from substrate-(FIG. 3A) and chemical proteomic-assays (FIG. 3B). Probe-modified peptides showing high competition, as judged by SILAC ratios, were identified as ritanserin binding sites in DMSO/ritanserin comparisons (SR >5, FIG. 6A and Table 1 and 1A.

These criteria were used to discover that ritanserin inhibits DGKα predominantly through binding interactions at the C1 (K237, SR=7.0) and DAGKa sites (K539, SR=7.0; FIG. 6B and Table 1 and 1A). Surprisingly, minimal competition at the DAGKc domain was observed (K377, SR=2.0; Table 1 and 1A). Ritanserin competed at common (DAGKa) as well as distinct binding sites (C1) compared with ATP substrate (Table 1 and 1A). The unusual binding mode of ritanserin identified from the LC-MS studies may help explain previous kinetic assays describing a mixed competitive mechanism of inhibition for this inhibitor; ritanserin is hypothesized to bind a DGKα-ATP complex through an unidentified binding site (Boroda et al., 2017). It is proposed that C1 could be a potential site mediating ritanserin binding to DGKα distinct from the ATP pocket. Inhibitor profiling of other DGKs revealed that ritanserin showed minimal activity against other isoforms (SR<2 at all binding sites detected, FIG. 6A and Table 1 and 1A). Ritanserin competition was specific because treatment with the negative control probe ketanserin resulted in negligible competition at all probe-binding sites with the exception of a lower SILAC ratio for DGKK peptide, which indicates a potential activating effect for this isoform (FIG. 6A and Table 1 and 1A).

One of the advantages of using chemical proteomics is the ability to simultaneously evaluate on- and off-target activity of inhibitors directly in cell proteomes (Chang et al., 2015; Nagano et al., 2013). Here, the selectivity of ritanserin was measured against >50 native kinases quantified in HEK293T soluble proteomes (FIG. 7A). On average, >200 probe-modified peptides were detected from ~85 protein and lipid kinases per individual SILAC sample. The kinome coverage is comparable with previous reports using ATP acyl phosphates and data-dependent MS scan modes (Patricelli et al., 2007). Native kinases reported in FIG. 7A and Table 1 and 1A were quantified in at least 2 biological replicates across all treatment conditions and competed by treatment with free ATP (SR >5, Table 1 and 1A). The latter criterion (i.e. ATP competition) was important for identifying non-specific probe labeling events in the studies (see Materials and Methods for more details). Kinase targets of ritanserin were defined as those active site peptides that showed SILAC ratios ≥5. Based on this criterion, the most potent targets of ritanserin were DGKα and the non-receptor tyrosine protein kinase FER (Greer, 2002) (SR=7.9; FIGS. 7A and B). It was confirmed that ritanserin was competing at ATP binding sites of FER by demonstrating potent competition at the same site (K591) with free ATP (SR=19.3, Table 1 and 1A). Collectively, the studies demonstrate the use of chemical proteomics to elucidate the binding mode and selectivity of ritanserin, resulting in discovery of the C1 domain as a novel ligand binding site and FER as an unanticipated off-target. Discovery of a Lead Fragment Inhibitor of DGKα by Ritanserin Deconstruction.

In an effort to improve selectivity of ritanserin for DGKα, ligand deconstruction (Hajduk et al., 2000; Kozakov et al., 2015; Lingel et al., 2017) strategies were explored to evaluate the contributions of representative fragments for binding affinity and selectivity. It was hypothesized that the 4-substituted piperidine moiety of ritanserin (highlighted in red, FIG. 7C) is a likely pharmacophore required for DGKα inhibition because of conservation of this motif across several DGKα inhibitors (Boroda et al., 2017) (FIG. 10E). Here, the capacity of quantitative chemical proteomics was tested to evaluate binding mode and selectivity of a ritanserin fragment (designated RF001, FIG. 7C) against recombinant DGKs and endogenous kinases directly in native cell proteomes.

Figure 12:
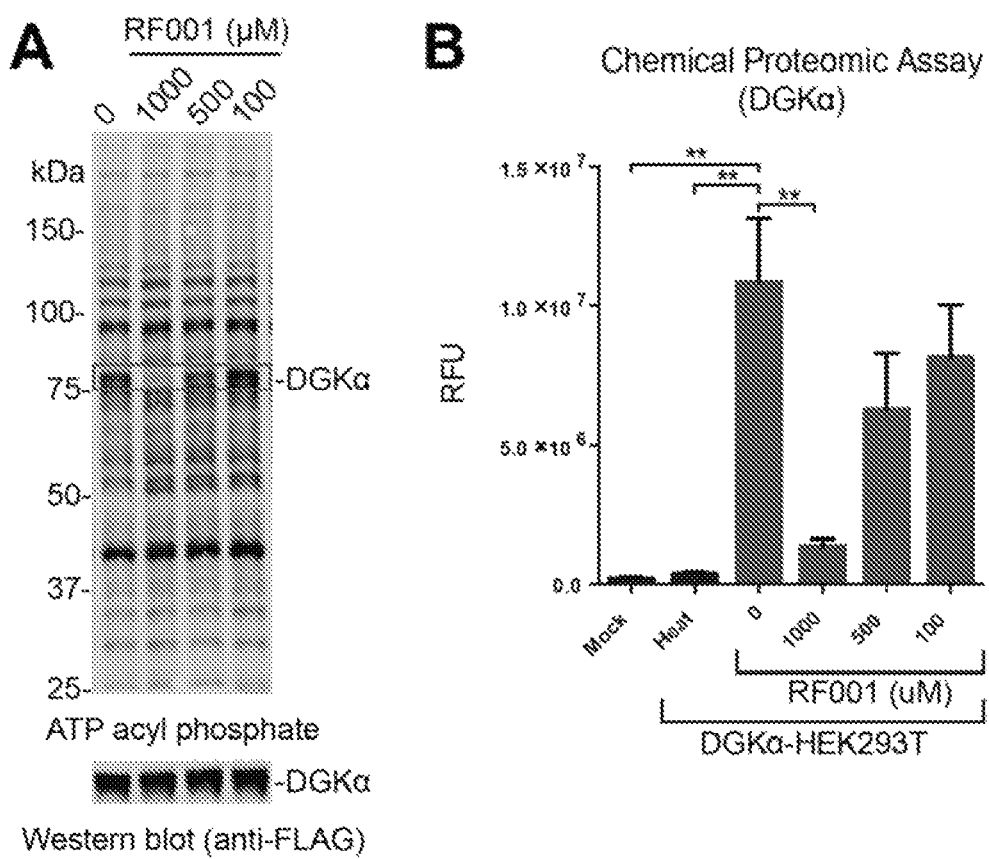

It was confirmed that RF001 blocked DGKα activity in a concentration-dependent manner using the DAG phosphorylation substrate assay ($IC_{50=223}$ UM, FIG. 7C). The data show substantially lower potency of RF001 compared with ritanserin (~10-fold difference in $IC_{50}$ values when comparing FIGS. 3A and 7C), which is expected of low molecular weight fragments (<300 Da) that typically exhibit binding affinities in the high micromolar to millimolar range (Erlanson et al., 2016). To account for differences in potency, RF001 was tested at 10-fold higher concentrations (1 mM) in the subsequent LC-MS assays. This concentration of RF001 was chosen to provide >80% inhibition of DGKα activity in the probe-binding assay (FIG. 12). Akin to ritanserin, RF001 treatment resulted in potent competition at C1 (SR=12.6) and DAGKa sites (SR=9.1) while showing weak activity at the DAGKc site (SR=1.7, FIG. 7D and Table 1 and 1A). It was also confirmed that RF001 was largely inactive against other DGK subtypes as determined by low SILAC ratios at all detected DGK probe-modified sites (average SR ~1, FIG. 7A and Table 1 and 1A). The similar inhibition profiles of RF001 and ritanserin observed in the LC-MS analyses support that the ritanserin binding mode is conserved with the ritanserin fragment and that the 4-substituted piperidine group represents a core binding motif of DGKα inhibitors.

While ritanserin and RF001 share similar inhibition profiles within the DGK family, they differed substantially in cross-reactivity against the kinome. A striking finding from the studies is the dramatic improvement in selectivity against the kinome observed with RF001 compared with ritanserin (FIG. 7A). Specifically, the potent FER off-target activity observed with ritanserin was largely eliminated using RF001 (SR=1.2, FIG. 7B). In fact, RF001 showed potent activity (SR >5) against a single kinase target, DGKα, across all detectable kinases (native and recombinant DGKs) quantified in the chemical proteomics studies (FIG. 7A and Table 1 and 1A). Closer inspection of the data revealed that unlike ritanserin, RF001 maintained good selectivity even for kinase targets that show moderate to weak inhibitory activity (25 versus 3 kinase targets that show SR >2 for ritanserin versus RF001, respectively; FIG. 7E).

DISCUSSION

Figure 5:
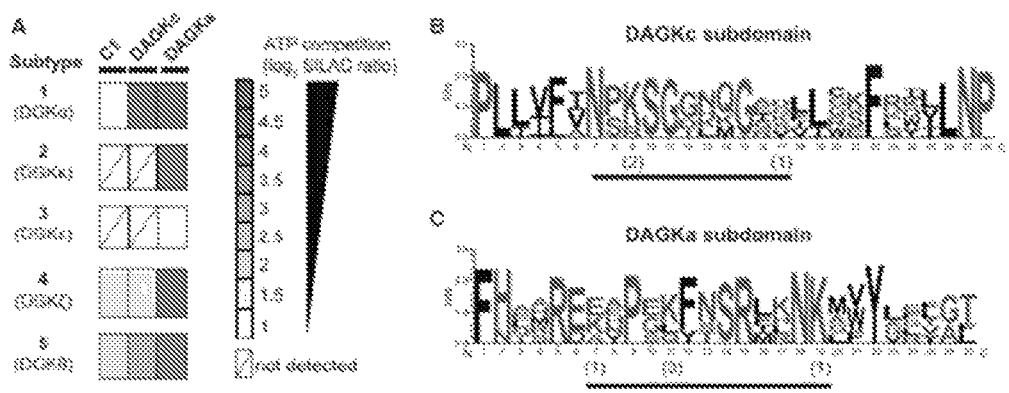

ATP acyl phosphates and quantitative LC-MS were used to map ligand-binding regions corresponding to the active site of mammalian DGKs. It was defined, for the first time, the location of the ATP binding site of representative isoforms from all five principal DGK subtypes (FIG. 5). Inspection of the DGK ATP binding sites reveals several features that are unique to this lipid kinase family. First, ATP-sensitive, probe-modified peptides were identified from both DAGKc and DAGKa subdomains, supporting interactions between these regions within the catalytic domain to constitute a potential ATP binding cleft. Crystal structures of soluble bacterial lipid kinases with homology to mammalian DGKs have also been found with active sites located in an interdomain cleft (Bakali et al., 2007). The finding that the DAGKa region is involved in substrate binding was important for assigning a catalytic role to this domain and helps explain previous reports that C-terminal truncations impair DGK enzymatic activity (Los et al., 2004). Second, conserved sequences corresponding to ATP binding sites of DGKs (FIGS. 5B and C) are not homologous with glycine-rich loops mediating ATP binding of protein kinases (Hanks et al., 1988; Hemmer et al., 1997). The data provide the first experimental evidence in support of a unique DGK ATP binding motif that was postulated over 20 years ago (Schaap et al., 1994). Finally, it is speculated that detection of a single ATP binding site (as opposed to 2 sites in other DGKs) for DGKK and DGK& is a reflection of functional differences in substrate binding of DGK subtypes (FIG. 5A). In support of this hypothesis, DGKK, along with other type 2 members, contain an unusual peptide motif that physically separates the DAGKc and DAGKa subdomains (Imai et al., 2005). DGKE, the sole type 3 member, is the only subtype that lacks regulatory domains and shows acyl chain preference in DAG substrate assays in vitro (Tang et al., 1996). It is noted that DGKK and DGK& showed lower recombinant protein expression compared with other isoforms (FIG. 8) and so one cannot rule out the possibility of detection limits using the LC-MS approach.

Clues to domain binding sites of DGKs and how to exploit these regions for development of DGKα-selective inhibitors were also discovered. The identification of a probe-modified site at C1 domain provided the first evidence of a ligand binding site remote from the ATP binding region of DGKs. Although one cannot rule out the possibility of alternative mechanisms, e.g. probe binding due to domain-(Nordin et al., 2015) or protein-interactions (Okerberg et al., 2014), evidence is provided that the C1 domain serves as a ligand binding site for ritanserin distinct from the ATP binding region of DGKα (FIGS. 5A and 6A). The overlapping (DAGKa) and distinct (C1) binding sites of ritanserin compared with ATP helps explain previous kinetic findings of a mixed competitive mechanism of inhibition whereby ritanserin prefers to bind a DGKα-ATP complex (Boroda et al., 2017). It was investigated how the binding mode of ritanserin affects selectivity against other DGK isoforms as well as >50 native kinases detected in cell proteomes. While ritanserin showed good selectivity within the DGK superfamily, discovered substantial cross-reactivity against protein kinases was discovered, including the non-receptor tyrosine kinase FER that was inactivated to a similar magnitude as DGKα (SR=7.9, FIGS. 7A and B). An unexpected finding was the discovery that a ritanserin fragment. (RF001) functioned as a DGKα inhibitor that retained binding at C1 and DAGKa sites (FIG. 7D) and largely removed FER and other kinase off-target activity (FIGS. 7A and E). Conservation of fragment binding mode is characteristic of ligand-binding hotspots (Hall et al., 2015; Kozakov et al., 2015) of proteins suitable for fragment-based lead and drug discovery (Erlanson et al., 2016).

Conclusion

The studies describe the first functional proteomic map of ligand-binding regions that mediate substrate (ATP) and inhibitor binding in the poorly annotated active site of the mammalian diacylglycerol kinase (DGK) superfamily. Given the dearth of lipid kinase inhibitors available in the clinic and the emerging role of DGKs as anticancer and immunotherapy targets, it is believed that the findings offer new prospects for chemical probes to study and target lipid kinases. It is defined, for the first time, the location of the ATP binding site of representative isoforms from all five principal DGK subtypes (type 1-5). Inspection of DGK ATP binding sites identify conserved features that are distinct from protein kinases, providing the first experimental evidence in support of a DGK-specific ATP binding motif that was postulated over 20 years ago. Clues to domain regions of DGKs important for inhibitor development were discovered by identifying probe-modified sites in C1 and accessory (DAGKa) domains that serve as primary binding sites for the DGKα inhibitor ritanserin. An unexpected finding was the discovery that a fragment of ritanserin (RF001) functioned as a DGKα inhibitor that retained binding at C1 and DAGKa domains and largely removed protein kinase off-target activity. While few examples have been reported, conservation of fragment binding mode is characteristic of ligand-binding hotspots of proteins suitable for fragment-based lead discovery. Thus, it is believed that the C1 and DAGKa sites are key binding regions of DGKs to enable development of high affinity, isoform-selective inhibitors of this lipid kinase superfamily.

BIBLIOGRAPHY

Abe, T., et al. (2003). Site-directed mutagenesis of the active site of diacylglycerol kinase alpha: calcium and phosphatidylserine stimulate enzyme activity via distinct mechanisms. Biochem J 375, 673-680.

Adams, D. R., et al. (2016). Sphingosine Kinases: Emerging Structure-Function Insights. Trends Biochem Sci 41, 395-409.

Adibekian, A., et al. (2012). Confirming target engagement for reversible inhibitors in vivo by kinetically tuned activity-based probes. J Am Chem Soc 134, 10345-10348.

Bakali, H. M., et al. (2007). Crystal structure of YegS, a homologue to the mammalian diacylglycerol kinases, reveals a novel regulatory metal binding site. J Biol Chem 282, 19644-19652.

Barone, J. A., et al. (1986). Safety evaluation of ritanserin--an investigational serotonin antagonist. Drug Intell Clin Pharm 20, 770-775.

Boroda, S., et al. (2017). Dual activities of ritanserin and R59022 as DGKalpha inhibitors and serotonin receptor antagonists. Biochem Pharmacol 123, 29-39.

Brown, H. A., et al. (2017). Targeting phospholipase D in cancer, infection and neurodegenerative disorders. Nat Rev Drug Discov 16, 351-367.

Carrasco, S., and Merida, I. (2007). Diacylglycerol, when simplicity becomes complex. Trends Biochem Sci 32, 27-36.

Chang, J. W., et al. (2015). Selective inhibitor of platelet-activating factor acetylhydrolases 1b2 and 1b3 that impairs cancer cell survival. ACS Chem Biol 10, 925-932.

Crooks, G. E., et al. (2004). WebLogo: a sequence logo generator. Genome Res 14, 1188-1190.

Crotty, T., et al. (2006). Diacylglycerol kinase delta regulates protein kinase C and epidermal growth factor receptor signaling. Proc Natl Acad Sci USA 103, 15485-15490.

de Chaffoy de Courcelles, D., et al. (1989). The role of endogenously formed diacylglycerol in the propagation and termination of platelet activation. A biochemical and functional analysis using the novel diacylglycerol kinase inhibitor, R59 949. J Biol Chem 264, 3274-3285.

de Chaffoy de Courcelles, D. C., et al. (1985). R59 022, a diacylglycerol kinase inhibitor. Its effect on diacylglycerol and thrombin-induced C kinase activation in the intact platelet. J Biol Chem 260, 15762-15770.

Dominguez, C. L., et al. (2013). Diacylglycerol kinase alpha is a critical signaling node and novel therapeutic target in glioblastoma and other cancers. Cancer Discov 3, 782-797.

Erlanson, D. A., et al. (2016). Twenty years on: the impact of fragments on drug discovery. Nat Rev Drug Discov 15, 605-619.

Fang, Y., et al. (2001). Phosphatidic acid-mediated mitogenic activation of mTOR signaling. Science 294, 1942-1945.

Goto, K., and Kondo, H. (1996). A 104-kDa diacylglycerol kinase containing ankyrin-like repeats localizes in the cell nucleus. Proc Natl Acad Sci US A 93, 11196-11201.

Goujon, M., et al. (2010). A new bioinformatics analysis tools framework at EMBL-EBI. Nucleic Acids Res 38, W695-699.

Greer, P. (2002). Closing in on the biological functions of Fps/Fes and Fer. Nat Rev Mol Cell Biol 3, 278-289.

Hajduk, P. J., et al. (2000). Design of adenosine kinase inhibitors from the NMR-based screening of fragments. J Med Chem 43, 4781-4786.

Hall, D. R., et al. (2015). Lessons from Hot Spot Analysis for Fragment-Based Drug Discovery. Trends Pharmacol Sci 36, 724-736.

Hanks, S. K., et al. (1988). The protein kinase family: conserved features and deduced phylogeny of the catalytic domains. Science 241, 42-52.

Hemmer, W., et al. (1997). Role of the glycine triad in the ATP-binding site of cAMP-dependent protein kinase. J Biol Chem 272, 16946-16954.

Houssa, B., et al. (1997). Cloning of a novel human diacylglycerol kinase (DGKtheta) containing three cysteine-rich domains, a proline-rich region, and a pleckstrin homology domain with an overlapping Ras-associating domain. J Biol Chem 272, 10422-10428.

Hsu, K. L., et al. (2012). DAGLbeta inhibition perturbs a lipid network involved in macrophage inflammatory responses. Nat Chem Biol 8, 999-1007.

Hurley, J. H., and Misra, S. (2000). Signaling and subcellular targeting by membrane-binding domains. Annu Rev Biophys Biomol Struct 29, 49-79.

Imai, S., et al. (2005). Identification and characterization of a novel human type II diacylglycerol kinase, DGK kappa. J Biol Chem 280, 39870-39881.

Kozakov, D., et al. (2015). Ligand deconstruction: Why some fragment binding positions are conserved and others are not. Proc Natl Acad Sci USA 112, E2585-2594.

Lingel, A., et al. (2017). Structure-Guided Design of EED Binders Allosterically Inhibiting the Epigenetic Polycomb Repressive Complex 2 (PRC2) Methyltransferase. J Med Chem 60, 415-427.

Liu, K., et al. (2016). A novel diacylglycerol kinase alpha-selective inhibitor, CU-3, induces cancer cell apoptosis and enhances immune response. J Lipid Res 57, 368-379.

Los, A. P., et al. (2004). Structure-activity relationship of diacylglycerol kinase theta. Biochim Biophys Acta 1636, 169-174.

Mann, M. (2006). Functional and quantitative proteomics using SILAC. Nat Rev Mol Cell Biol 7, 952-958.

Merida, I., et al. (2017). Diacylglycerol kinases in cancer. Adv Biol Regul 63, 22-31.

Merino, E., et al. (2007). Role of the diacylglycerol kinase alpha-conserved domains in membrane targeting in intact T cells. J Biol Chem 282, 35396-35404.

Miller, D. J., et al. (2008). Analysis of the *Staphylococcus aureus* DgkB structure reveals a common catalytic mechanism for the soluble diacylglycerol kinases. Structure 16, 1036-1046.

Nagano, J. M., et al. (2013). Selective inhibitors and tailored activity probes for lipoprotein-associated phospholipase A (2). Bioorg Med Chem Lett 23, 839-843.

Newton, A. C., and Koshland, D. E., Jr. (1989). High cooperativity, specificity, and multiplicity in the protein kinase C-lipid interaction. J Biol Chem 264, 14909-14915.

Nordin, B. E., et al. (2015). ATP Acyl Phosphate Reactivity Reveals Native Conformations of Hsp90 Paralogs and Inhibitor Target Engagement. Biochemistry 54, 3024-3036.

Okerberg, E. S., et al. (2014). Monitoring native p38alpha: MK2/3 complexes via trans delivery of an ATP acyl phosphate probe. J Am Chem Soc 136, 4664-4669.

Patricelli, Matthew P., et al. (2011). In Situ Kinase Profiling Reveals Functionally Relevant Properties of Native Kinases. Chemistry & Biology 18, 699-710.

Patricelli, M. P., et al. (2007). Functional interrogation of the kinome using nucleotide acyl phosphates. Biochemistry 46, 350-358.

Posch, A., et al. (2013). V3 stain-free workflow for a practical, convenient, and reliable total protein loading control in western blotting. J Vis Exp, 50948.

Prinz, P. U., et al. (2012). High DGK-alpha and disabled MAPK pathways cause dysfunction of human tumor-infiltrating CD8+ T cells that is reversible by pharmacologic intervention. J Immunol 188, 5990-6000.

Purow, B. (2015). Molecular Pathways: Targeting Diacylglycerol Kinase Alpha in Cancer. Clinical Cancer Research 21, 5008-5012.

Sakane, F., et al. (1996). The C-terminal part of diacylglycerol kinase alpha lacking zinc fingers serves as a catalytic domain. Biochem J 318 (Pt 2), 583-590.

Sakane, F., et al. (2016). Diacylglycerol Kinases as Emerging Potential Drug Targets for a Variety of Diseases: An Update. Front Cell Dev Biol 4, 82.

Sakane, F., et al. (1990). Porcine diacylglycerol kinase sequence has zinc finger and E-F hand motifs. Nature 344, 345-348.

Santos, T., et al. (2002). Dynamics of diacylglycerol kinase zeta translocation in living T-cells. Study of the structural domain requirements for translocation and activity. J Biol Chem 277, 30300-30309.

Sato, M., et al. (2013). Evaluations of the selectivities of the diacylglycerol kinase inhibitors R59022 and R59949 among diacylglycerol kinase isozymes using a new non-radioactive assay method. Pharmacology 92, 99-107.

Schaap, D., et al. (1994). Consensus sequences for ATP-binding sites in protein kinases do not apply to diacylglycerol kinases. Biochem J 304 (Pt 2), 661-662.

Schilling, B., et al. (2012). Platform-independent and label-free quantitation of proteomic data using MS1 extracted ion chromatograms in skyline: application to protein acetylation and phosphorylation. Mol Cell Proteomics 11, 202-214.

Schneider, T. D., and Stephens, R. M. (1990). Sequence logos: a new way to display consensus sequences. Nucleic Acids Res 18, 6097-6100.

Schultz, J., et al. (1998). SMART, a simple modular architecture research tool: Identification of signaling domains. Proceedings of the National Academy of Sciences 95, 5857-5864.

Shindo, M., et al. (2003). Synthesis and phorbol ester binding of the cysteine-rich domains of diacylglycerol kinase (DGK) isozymes. DGKgamma and DGKbeta are new targets of tumor-promoting phorbol esters. J Biol Chem 278, 18448-18454.

Shulga, Y.V., et al. (2011). Regulation and Functions of Diacylglycerol Kinases. Chemical Reviews 111, 6186-6208.

Sievers, F., et al. (2011). Fast, scalable generation of high-quality protein multiple sequence alignments using Clustal Omega. Mol Syst Biol 7, 539.

Takai, Y., et al. (1979). Unsaturated diacylglycerol as a possible messenger for the activation of calcium-activated, phospholipid-dependent protein kinase system. Biochem Biophys Res Commun 91, 1218-1224.

Tang, W., et al. (1996). Molecular cloning of a novel human diacylglycerol kinase highly selective for arachidonate-containing substrates. J Biol Chem 271, 10237-10241.

Yada, Y., et al. (1990). Purification and characterization of cytosolic diacylglycerol kinases of human platelets. J Biol Chem 265, 19237-19243.

Yetukuri, L., et al. (2008). Informatics and computational strategies for the study of lipids. Mol Biosyst 4, 121-127.

Example 2

Ritanserin is a CRAF Inhibitor with Cytotoxicity against Small Cell Lung Cancer Cells

INTRODUCTION

Figure 14:
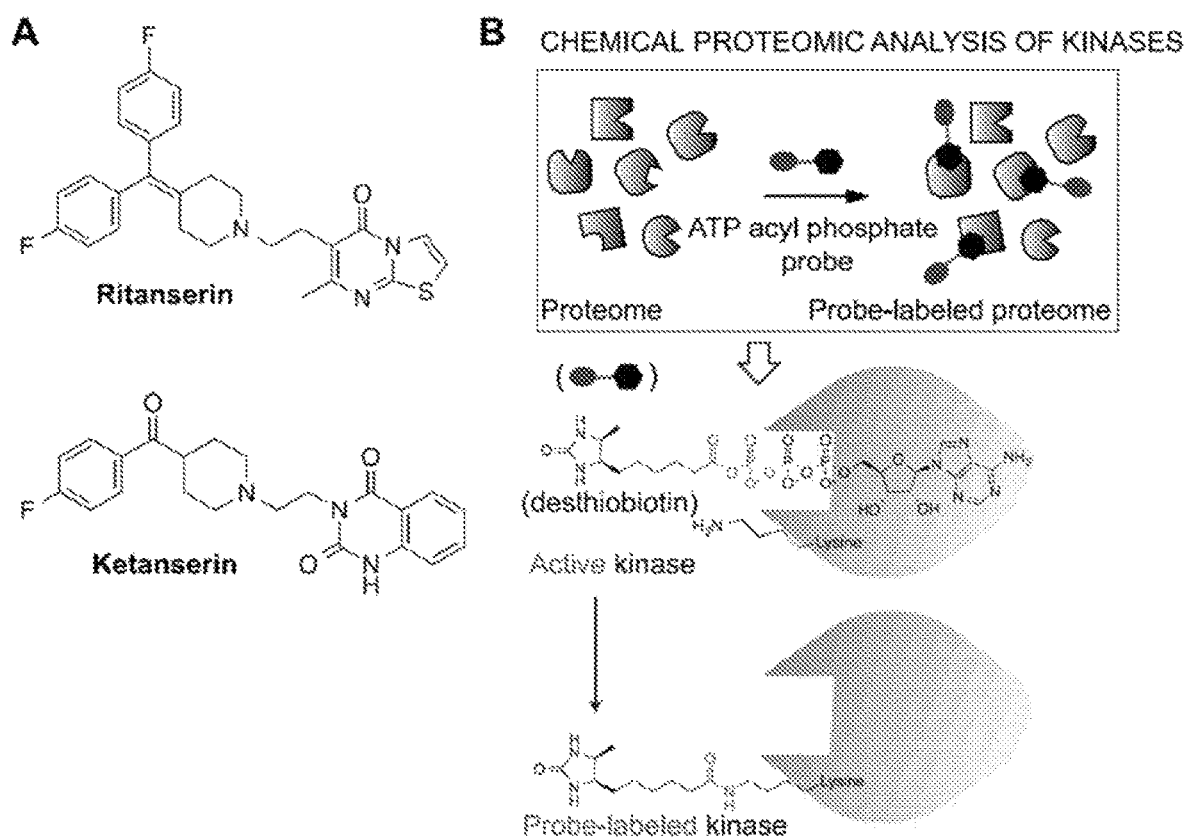

Ritanserin is a serotonin (5-hydroxytryptamine, 5-HT) receptor antagonist with specificity for the 5-HT2 subtype (Leysen, 1985). As a drug candidate, ritanserin was tested for treatment of several neuropsychiatric disorders but never received approval for clinical use (31). The oral bioavailability (~40-hour half-life) and lack of adverse side effects in humans has since prompted studies to explore ritanserin for clinical applications beyond serotonin signaling (Purow, 2015). For example, ritanserin was discovered to function as a diacylglycerol kinase-alpha (DGKα) inhibitor, which shifted focus towards use of this compound for modulation of lipid signaling in cancer (Boroda, 2017; Purow, 2015) (FIG. 14). As demonstrated herein, quantitative chemical proteomics was used to evaluate ritanserin selectivity against the kinome and it was discovered that the non-receptor tyrosine protein kinase FER is an additional potent target (Franks, 2017). Epidermal growth factor receptor (EGFR) signaling activates FER resulting in phosphorylation and activation of the guanine nucleotide exchange factor (GEF) Vav2 to enhance cell migration, invasion, and tumor metastasis of lung cancer cells (Ahn, 2013). Thus, ritanserin is capable of disrupting lipid and protein pathways mediating oncogenic signaling and can serve as a useful candidate for targeting broad tumor cell types. Here, ritanserin cytotoxicity and kinome-wide selectivity in lung cancer cells that differed by subtype and mutational status is evaluated.

Materials and Methods

Materials. Desthiobiotin ATP acyl phosphate nucleotide probe was obtained from ThermoFisher Scientific (PI88311). Ritanserin and ketanserin tartrate were purchased from Tocris Bioscience. WST-1 reagent kits were purchased from Cayman Chemical. Trypan Blue was purchased from ThermoFisher Scientific. CaspaseGlo Assay kits were purchased from Promega.

WST-1 Cell Proliferation Assays. Tumor cells were plated in transparent tissue-culture treated 96-well plates at a density of 100,000 cells/mL (A549, $H_{1650}$) or 200,000 cells/mL ($H_{82}$) in a volume of 100 μL per well. Cells were treated with dimethyl sulfoxide (DMSO) vehicle or inhibitors dissolved in DMSO at the indicated concentrations (final DMSO concentration of 0.5%). Cells were allowed to grow for indicated times at 37° C. under 5% $CO_2$. Afterwards, equal parts of WST-1 developer reagent and electron mediator solution were mixed and 10 μL of the resulting solution ('WST-1 reagent') were added to each well. Plates were shaken in an orbital shaker for 60 s and then returned to the incubator for two hrs. Plates were again shaken followed measurement of absorbance at 450 nm. Data were normalized to DMSO-treated wells and significance values determined with one-way ANOVA.

Cell Counts. Tumor cells were plated in 60 mm plates at a density of 100,000 cells/mL (A549, H1650) or 200,000 cells/ml. (H82) and a volume of 3.5 ml/plate. Cells were treated with inhibitors at the indicated concentrations (final DMSO concentration of 0.5%) for 48 hrs at 37° C. under 5% $CO_2$. After incubation, adherent cells were washed and detached with trypsin and all cells were collected and concentrated by spinning at 400×g for 3 min followed by aspiration of media. Cells were resuspended in 10 nM Trypan Blue and 10 μL of this solution counted via a hemocytometer. Dead cells were excluded from all counts. Data were normalized to DMSO-treated wells and significance values determined with one-way ANOVA.

Caspase Glo Assays. Assays were performed as directed by the manufacturer (Promega). Briefly, tumor cells were plated in black tissue-culture treated transparent-bottom 96 well plates at a density of 200,000 cells/mL (A549, H1650) or 400,000 cells/mL (H82) in a volume of 50 μL/well. Cells were treated with inhibitors at the indicated concentrations (final DMSO concentration of 0.5%) for 24 hrs at 37° C. under 5% $CO_2$. Afterwards, 50 μL of the prepared Caspase-Glo reagent was added to each well. The reaction was allowed to proceed at 37° C. under 5% $CO_2$ for 1 hr, at which point the cells were shaken in an orbital shaker at 500 rpm for 60 s and then luminescence was read for each well. Data were normalized to DMSO-treated wells and significance values determined with one-way ANOVA.

LC-MS analysis of SILAC samples using ATP acyl phosphates. Quantitative chemoproteomics was performed as previously described (Franks et al., 2017; McCloud et al., 2018).

Computational Methods. Data for A549 and H82 cell lines were searched with IP2 and manually validated using the methods previously described (Franks et al., 2017). Data for Desthiobiotin-tagged ATP acyl-phosphate probes and ATP competitive peptides were compared and clustered. Ritanserin and ketanserin inhibition profiles were compared using SILAC ratios and normalized to DMSO. The kinase profiles were displayed as a heatmap and clustered with hierarchical clustering using R package d3heatmaps (blog.rstudio.org/2015/06/24/d3heatmap/) as previously described (Franks et al., 2017).

Lipid kinase phylogenetic tree. Phylogenetic tree of human lipid kinases was generated using MUSCLE multiple sequence alignment (Edgar, 2004) of annotated lipid kinases and a least squared distance method for determining evolutionary distance. Calculations were conducted using the EMBOSS software suite (Rice et al., 2000).

Statistical analysis and determination of $IC_{50}$ values. For all cell viability measurements, results were normalized to values obtained from DMSO treated cells. For CaspaseGlo assays, raw luminescence values are reported. All significance values for Cell Viability and CaspaseGlo assays were calculated with one-way ANOVA. All statistical analyses were performed using GraphPad Prism.

Results and Discussion

Figure 15:
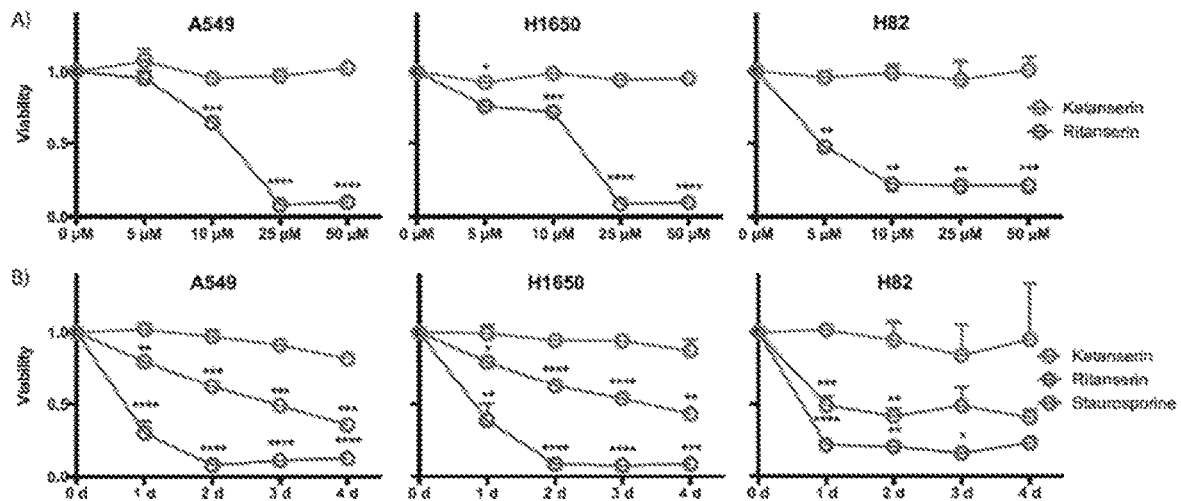

Ritanserin Mediates Apoptotic Cell Death of Lung Cancer Cells Independent of Serotonin Signaling Cell viability assays were conducted to determine the impact of ritanserin treatments on survival of NSCLC and SCLC cells. H1650 and A549 were chosen as the non-small cell lung cancer (NSCLC) cell models to compare sensitivity of cells with different gene mutations to ritanserin exposure. H1650 express EGFR receptors contain activating mutations in the kinase domain (exon 19 deletion E746-A750 (Irmer, 2007 #4631)) of this receptor tyrosine kinase. A549 cells express wild-type EGFR but harbor mutant KRAS (G12S) (Kharbanda, 2014). H82 cells (Jahchan, 2013) were also included in the studies to evaluate ritanserin activity in small cell lung cancer (SCLC). Ketanserin (Franks, 2017; Boroda, 2017) was used alongside ritanserin to control for potential 5-HT2R activity and other non-specific pharmacological effects in cell biology. Cells were treated with varying ritanserin concentrations (5-50 M) and cell viability measured using established WST-1 metabolic assays (Kepp, 2011). Concentration-dependent decreases in viability in cells exposed to ritanserin but not ketanserin treatments was observed (FIG. 15A, FIGS. 18A and B). At a moderate concentration of ritanserin (25 μM), >70% inhibition of cell growth across all NSCLC and SCLC lines exposed to compound was observed (FIG. 15A). At lower concentrations (5 μM), ritanserin showed enhanced cytotoxicity against the SCLC H82 (~50% cell death) cells compared with NSCLC cells (~5-15% cell death across A549 and H1650 cells, FIG. 15A). Cell killing with ritanserin was rapid with >50% of cell death occurring after 1 day and near-maximal cytotoxicity after 2 days of treatment in all cell lines (25 UM dose, FIG. 15B). The lack of activity using ketanserin under the same treatment conditions further supports that ritanserin-mediated cytotoxicity of lung cancer cells is not due to antagonism of 5-HT2R receptors (FIG. 15, FIGS. 18A and B). In contrast to pan-kinase inhibitor staurosporine, which showed general cytotoxicity across all cells tested (FIG. 15B and FIG. 18C), ritanserin showed negligible cell killing against noncancerous primary cells even at the highest concentration tested (50 μM, FIG. 19C). Collectively, the results demonstrate that ritanserin is not generally cytotoxic but displays potent cell killing of NSCLC and SCLC cells.

Since changes in cell metabolism can occur from nonlethal perturbations (Kepp, 2011), live cell counts were used to further support cytotoxicity of lung cancer cells with ritanserin treatments (FIG. 16A). Akin to results from cell viability assays, significant cell killing was observed across all lung cancer cell lines exposed to ritanserin but not ketanserin (FIG. 16A). Potent cell killing (~70%) was observed even at the lower dose tested (10 µM, FIG. 16A). Next, caspase activity was measured in treated cells to determine whether ritanserin mediates cell killing through activation of apoptosis. Cells treated with ritanserin showed significantly enhanced caspase 3/7 activity after 24 hours compared with vehicle controls (FIG. 16B). Caspase activation by ritanserin was specific because ketanserin treatments under the same experiments conditions did not induce these effects (FIG. 16B). Ritanserin effects were compared directly with staurosporine, which has been show in previous reports to activate apoptosis in lung cancer cells (Bartling, 2004; Wang, 2009). In both H1650 and H82 cells, comparable activation of caspase 3/7 compared with staurosporine was observed (FIG. 16B). While ritanserin treatment of A549 cells resulted in a lower degree of activation, the increase in caspase 3/7 was significant compared with vehicle and ketanserin treated cells (FIG. 16B). In summary, the cell viability and caspase activation data support ritanserin induction of apoptotic cell death against lung cancer cells that differ in mutation status (EGFR, KRAS) and subtype (NSCLC vs SCLC).

Chemical Proteomics to Elucidate Ritanserin Targets in NSCLC and SCLC Cell Proteomes Based on previous chemical proteomics (Franks, 2017), it was hypothesized that ritanserin is functioning as a kinase inhibitor to mediate cytotoxicity in the lung cancer cell models. Since A549 and H1650 displayed similar sensitivities to ritanserin in the cell viability assays, A549 and H82 were selected for chemical proteomic evaluation of ritanserin targets in NSCLC and SCLC proteomes, respectively. To test this hypothesis, desthiobiotin-tagged, ATP acyl-phosphates (Patricelli et al., 2011; Patricelli et al., 2007) were used to measure selectivity of compounds against native kinases detected in lung cancer proteomes. ATP acyl-phosphate probes permit global profiling of kinase activities by covalent attachment of reporter tags to conserved lysines in the ATP binding site of protein/lipid kinases as well as other ATP-binding proteins (Patricelli et al., 2011; Patricelli et al., 2007). For these studies, NSCLC and SCLC cells were cultured in isotopically light and heavy amino acids to enable quantitative chemical proteomics (Chang, 2015) by stable isotope labeling with amino acids in cell culture (SILAC, FIG. 17A). Light and heavy cell proteomes were treated with DMSO vehicle or compound, respectively, prior to addition of ATP acyl phosphate to label active site lysines. After probe labeling, light and heavy proteomes were combined, digested with trypsin protease, and desthiobiotin-modified peptides enriched by avidin affinity chromatography and analyzed by LC-MS/MS to identify and quantify isotopically tagged active-site peptides from native kinases as previously described (Franks, 2017) (FIG. 17A).

Using quantitative chemical proteomics assay described herein, kinase activity profiles between A549 and H82 cell proteomes were compared. Kinases included in the comparisons were quantified across at least 2 biological replicates and showed potent competition with free ATP (SR >5, FIG. 17A). The latter criterion was used to distinguish specific probe binding at ATP-binding sites versus non-specific labeling of surface lysines. Hierarchical clustering of the over 120 kinases separated into three distinct groups: overlapping, enriched for NSCLC and enriched for SCLC subtypes (FIG. 17A). Specifically, activity-dependent enrichment of several kinases was observed (AKT1/2/3 and IKKA) in A549 proteomes that is consistent with enhanced PI3K/AKT signaling in NSCLC subtypes containing KRAS mutations (Castellano, 2013) (FIG. 17A). A similar analysis of SCLC kinase profiles reveals enrichment of kinases involved in RAF signaling as well as the DNA damage response (FIG. 17A). In particular, the abundance of probe-modified active site peptides of CRAF was ~3 fold higher in H82 compared with A549 cell proteomes (FIG. 17B). These findings support previous observations that CRAF is one of several proto-oncogenes that are highly expressed in SCLC cells and tumor tissues (Graziano, 1991). Collectively, the kinase activity-based profiling studies reveal differences in signaling pathways that differentiate NSCLC and SCLC subtypes.

Next, ATP probe assay was used to determine the kinase targets of ritanserin in A549 and H82 proteomes (FIG. 17). Ketanserin was included in the LC-MS studies to discern ritanserin-specific from general non-specific activity of 5-HT2R antagonists against the kinome. The rationale for choosing to test a drug concentration $(100 \mu M)_{10}$-fold higher than required for potent cell killing (10 µM, FIG. 16A) is to account for potential shifts in potency of reversible inhibitors due to irreversible labeling kinetics of ATP acyl phosphate probe (Patricelli, 2011). Kinase targets of ritanserin were defined as those active site peptides that showed SILAC ratios ≥5. Based on this criterion, the most potent targets of ritanserin were FER, TLK2 and CRAF (FIG. 17). FER was identified as a potent target of ritanserin in previous chemical proteomic studies (Franks, 2017). Filtering by a three-fold change cutoff show BRAF inhibition by ritanserin. The combined inhibition of both RAF proteins suggests a mechanism for cancer cell cytotoxicity and presents the possibility of ritanserin treatment overcoming paradoxical CRAF activation in response to BRAF inhibition (Holderfield et al., 2013 Cancer Cell). It was confirmed that ritanserin was competing at ATP binding sites of target kinases by demonstrating potent competition at the same sites with free ATP.

Discovery that Ritanserin is a Direct Inhibitor of RAF1 Catalytic Activity

To further confirm that ritanserin is a CRAF inhibitor, a targeted parallel reaction monitoring method (PRM) was developed to evaluate compound activity against CRAF and other members of the RAF family (ARAF and BRAF). Targeted PRM was needed because of the low abundance of CRAF compared with ARAF and BRAF). Using the PRM approach, it was confirmed that ritanserin shows potent activity against CRAF with negligible activity against ARAF and BRAF in H82 proteomes (FIG. 17D). Ritanserin activity was also measured against RAF kinases in A549 proteomes using the targeted LC-MS method. It was found that one could not detect CRAF in A549 proteomes despite using a more sensitive LC-MS approach. The data further support previous findings that this RAF member is enriched in SCLC cells (REF). Collectively, it was confirmed that by using more sensitive LC-MS methods that ritanserin shows enhanced potency against CRAF among the RAF family of kinases.

Given the potential for indirect inhibitory effects in the competition studies in lysates, ritanserin activity was tested in a CRAF substrate assay. Ritanserin inhibition was measured against recombinant RAF1 using commercial substrate assays. These studies were validated the chemical proteomic findings by demonstrating that ritanserin could block RAF1 catalytic activity. RAF1 was overexpressed in HEK293T cells and measured recombinant RAF1 activity by comparing with non-transfected HEK293T (i.e. mock) proteomes. An increase was observed in RAF1-HEK293T compared with mock proteomes, which was specific because heat denaturation reduced activity back to mock levels. Pretreatment with ritanserin but not ketanserin resulted in concentrations dependent blockade of recombinant RAF1 activity. In summary, the results confirm agreement between chemical proteomics and biochemical substrate assays that ritanserin is a RAF1 inhibitor.

CONCLUSION

Ritanserin was tested in the clinic as a serotonin receptor (5-HT2R) antagonist but recently emerged as a novel kinase inhibitor with potential applications in cancer. Here, it is shown that ritanserin treatment induced apoptotic cell death of non-small cell lung cancer (NSCLC) and small cell lung cancer (SCLC) but not noncancerous cells. Treatment with a structurally analogous 5-HT2R antagonist ketanserin did not impact cell viability, supporting a ritanserin-specific and serotonin-independent effect. Chemical proteomics and quantitative mass spectrometry was used to identify putative kinase targets of ritanserin across the lung cancer kinome. Correlation of target engagement profiles with cytotoxicity resulted in discovery of CRAF as a putative target to explain enhanced sensitivity of SCLC cells to ritanserin treatment. Substrate assays using recombinant CRAF confirmed that ritanserin is a direct inhibitor of this oncogene. Thus, ritanserin has use as a drug repurposing in cancer. Novel activity of ritanserin in diverse lung cancer types segregated by type and mutation status has been shown. Provided herein is evidence that ritanserin functions as a kinase inhibitor with broad action against diverse lung cancer types. Ritanserin is identified as a novel inhibitor of RAF kinases with enhanced potency for RAF1.

Example 3

[A] Labeling HEK293T Cell Proteomes to Determine Target Proteins of JWB003 In Vitro
1. HEK293T cells were harvested in cold PBS.
    a. Cells were transferred to Eppendorf tube.
2. Cells were lysed via tip sonicator.
3. Cells were fractionated into membrane and soluble fraction.
    a. 100,000×G for 45 minutes at 4 degree.
    b. Supernatant was separated from cell pellet.
4. Dilute proteomes to 1 mg/mL in PBS and aliquot appropriate reaction volume (49 µL for probe only; 48 µL for competition+probe)
5. Cells were treated with 50× inhibitor.
    a. Incubated for 1 Hr at 37 degree.
6. Cells were treated with 50× Probe (JWB003).
    a. Incubated for 1 Hr at 37 degree.
7. Add 6 µL of master mix to each alkyne probe-labeled sample.
    a. 1 µL of 1.25 mM Rh—$N_3$
    b. 1 µL of fresh 50 mM TCEP
    c. 3 µL of 1.7 mM TBTA stock
    d. 1 µL of 50 mM $CuSO_4$
8. Vortex samples.
9. Incubate at room temperature for 1 hr
10. Quench with 17 µL of 4× SDS-PAGE loading buffer+ βME and vortex tubes.
11. Analyze 30 µL samples by SDS-PAGE immediately.
[B] Labeling HEK293T Cells to Determine Target Proteins of JWB003 in Live Cells (In Situ)
1. Complete media was removed from HEK293T cells and replaced with serum free media containing JWB003 at the appropriate final concentration
    a. Cells were placed in incubator for appropriate time at 37 degree 5% $CO_2$
2. Cells were washed
    a. 2× warm PBS
    b. 2× cold PBS
    c. Harvest cells in cold PBS
3. Cells were transferred to Eppendorf tube
4. Cells were lysed via tip sonicator
5. Cells were fractionated into membrane and soluble fraction
    a. 100,000×G for 45 minutes at 4 degrees
    b. Supernatant was separated from cell pellet.
6. Dilute proteomes to 1 mg/mL and aliquot appropriate reaction volume (50 µL)
7. Add 6 µL of master mix to each alkyne probe-labeled sample.
    a. 1µ L of 1.25 mM Rh—$N_3$
    b. 1 µL of fresh 50 mM TCEP
    c. 3 µL of 1.7 mM TBTA stock
    d. 1µ L of 50 mM $CuSO_4$
8. Vortex samples.
9. Incubate at room temperature for 1 hr.
10. Quench with 17 µL of 4× SDS-PAGE loading buffer+ βME and vortex tubes.
11. Analyze 30 µL samples by SDS-PAGE immediately.
[C] Screening Activity of Compounds Against Target Kinases Using a JWB003 Live Cell Labeling Assay
1. Complete media was removed from HEK293T cells and replaced with serum free media containing inhibitor or DMSO at the appropriate final concentration
    a. Cells were placed in incubator for 1 Hr at 37 degree 5% $CO_2$
2. Cells were treated with JWB003 (1000× stock)
    a. Cells were placed in incubator for 1 Hr at 37 degree 5% $CO_2$
3. Cells were washed
    a. 2× warm PBS
    b. 2× cold PBS
    c. Harvest cells in cold PBS
4. Cells were transferred to Eppendorf tube
5. Cells were lysed via tip sonicator
6. Cells were fractionated into membrane and soluble fraction
    a. 100,000×G for 45 minutes at 4 degrees
    b. Supernatant was separated from cell pellet.
7. Dilute proteomes to 1 mg/mL and aliquot appropriate reaction volume (50 µL)
8. Add 6 µL of master mix to each alkyne probe-labeled sample.
    a. 1 µL of 1.25 mM Rh—$N_3$
    b. 1µ L of fresh 50 mM TCEP
    c. 3 µL of 1.7 mM TBTA stock
    d. 1µ L of 50 mM $CuSO_4$
9. Vortex samples.
10. Incubate at room temperature for 1 hr.
11. Quench with 17 µL of 4× SDS-PAGE loading buffer+ βME and vortex tubes.
12. Analyze 30 µL samples by SDS-PAGE immediately.
[D] Labeling HEK293T Cell Proteomes to Determine Target Proteins of JWB017 In Vitro
1. HEK293T cells were harvested in cold PBS
    a. Cells were transferred to Eppendorf tube
2. Cells were lysed via tip sonicator
3. Cells were fractionated into membrane and soluble fraction
    a. 100,000×G for 45 minutes at 4 degree
    b. Supernatant was separated from cell pellet.

4. Dilute proteomes to 1 mg/mL and aliquot appropriate reaction volume (49 µL for probe only; 48 µL for competition+probe)
5. Cells were treated with 50× Probe (JWB003)
   a. Incubated for appropriate time point at 37 degree
6. Add 6 µL of master mix to each alkyne probe-labeled sample.
   a. 1 µL of 1.25 mM Rh—N₃
   b. 1 µL of fresh 50 mM TCEP
   c. 3 µL of 1.7 mM TBTA stock
   d. 1 µL of 50 mM CuSO₄
7. Vortex samples.
8. Incubate at room temperature for 1 hr.
9. Quench with 17 µL of 4× SDS-PAGE loading buffer+ βME and vortex tubes.
10. Analyze 30 µL samples by SDS-PAGE immediately.

[E] JWB017 Fluorescent Polarization Assay for High-Throughput Screening (HTS) of Purified Rat DGKα
1. Rat DGKα was diluted to 1 mg/ml in buffer (50 mM Tris 8.0, 150 mM NaCL, and 0.01% Pluronic F-127)
2. 9 µL of 4 µM of purified rat DGKα was aliquoted into 384 well plate (7 well)
3. 1 µL of DMSO or 10× probe was added to each well
4. Incubate at room temperature for appropriate time point
5. Read Fluorescence polarization Synthesis of RF001
tert-butyl 4-(bis(4-fluorophenyl) (hydroxy)methyl)piperidine-1-carboxylate

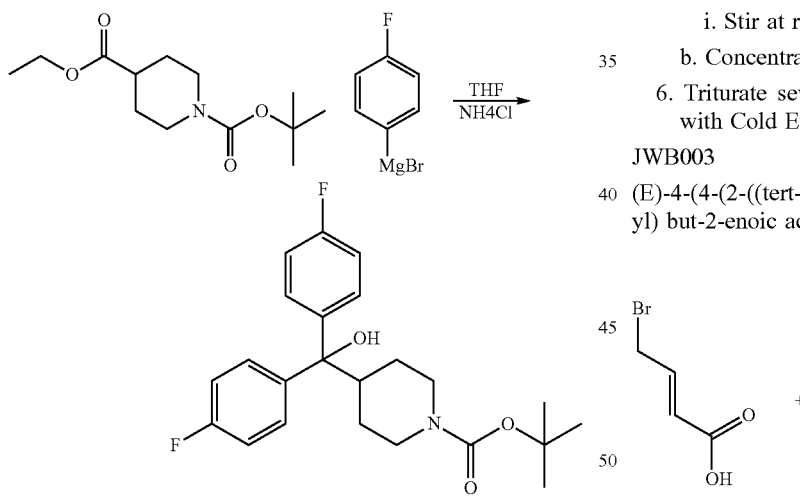

Molecular Weight: 403.4698

1. 1-Boc isonipecotic acid ester (1 eq) was dissolved in anhydrous THF and cold to 0 degree
   a. 4-fluorophenylmagnesium bromide (2.5 eq) was added dropwise via syringe
2. Flask allowed to warm to room temperature and stirred overnight
3. Reaction as quenched with saturated ammonium chloride a. Extract in EtOAC b. Wash with sodium bicarbonate c. Wash with brine
4. Concentrated on rotary evaporator:
5. Triturated several times with Cold EtOAC and hexanes
   a. Collected final product as white solid

RF001

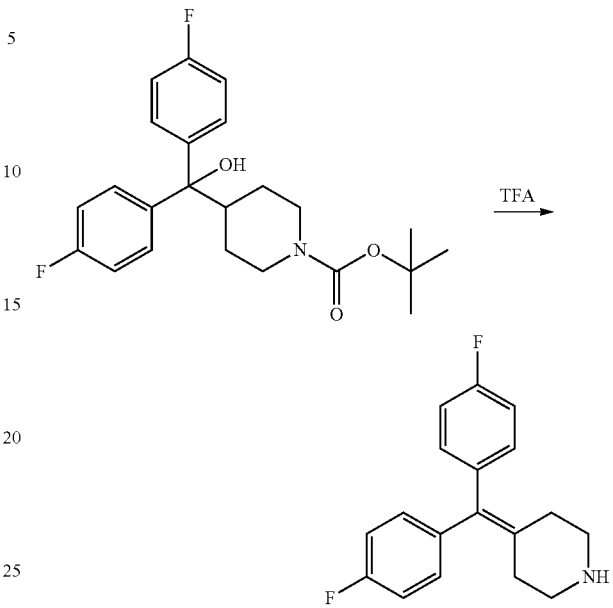

1. tert-butyl 4-(bis(4-fluorophenyl) (hydroxy)methyl)piperidine-1-carboxylate
   a. Dissolved in 1:1 mix of DCM and Trifluoroacetic acid
      i. Stir at room temperature for two hours
   b. Concentration on rotary evaporate
6. Triturate several times with Triturated several times with Cold EtOAC and hexane JWB003
(E)-4-(4-(2-((tert-butoxycarbonyl)amino)ethyl)piperazin-1-yl) but-2-enoic acid

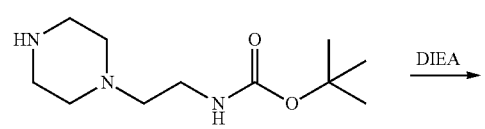

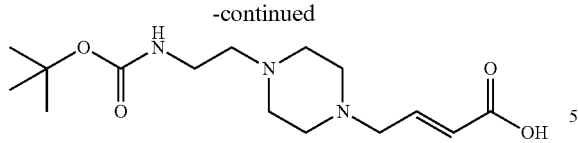

1. tert-butyl (2-(piperazin-1-yl)ethyl) carbamate (1.1 eq) was dissolved in THF a. Diisopropyl ethyl amine (eq) was added . . .
2. (E)-4-bromobut-2-enoic acid (1) was dissolved in THF and added to reaction flask
3. Flask was allowed to stir overnight;
4. Sample was concentrated via rotary evaporator and carried on to next step without further purification.

tert-butyl(E)-(2-(4-(4-(4-(bis(4-fluorophenyl)methylene) piperidin-1-yl)-4-oxobut-2-en-1-yl)piperazin-1-yl)ethyl) carbamate

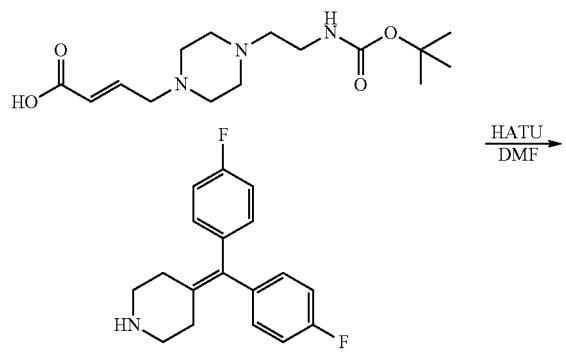

HATU / DMF

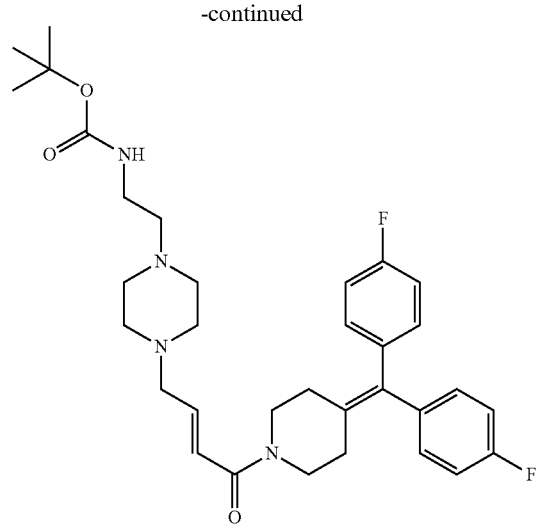

1. (E)-4-(4-(2-((tert-butoxycarbonyl)amino)ethyl)piperazin-1-yl) but-2-enoic acid (leq) was dissolved in 2 ml of anhydrous DMF.
2. HATU (2.2 eq) was added to the reaction flask and allowed to stir for one minute
3. RF001 (1.5 eq) and DIEA (3 eq) were dissolved in anhydrous DMF and added to the reaction flask
4. Reaction was allowed to stir overnight
5. Reaction was concentrated on rotary evaporator.
6. Purified via column chromatography 5-10% methanol in dichloromethane

JWB003

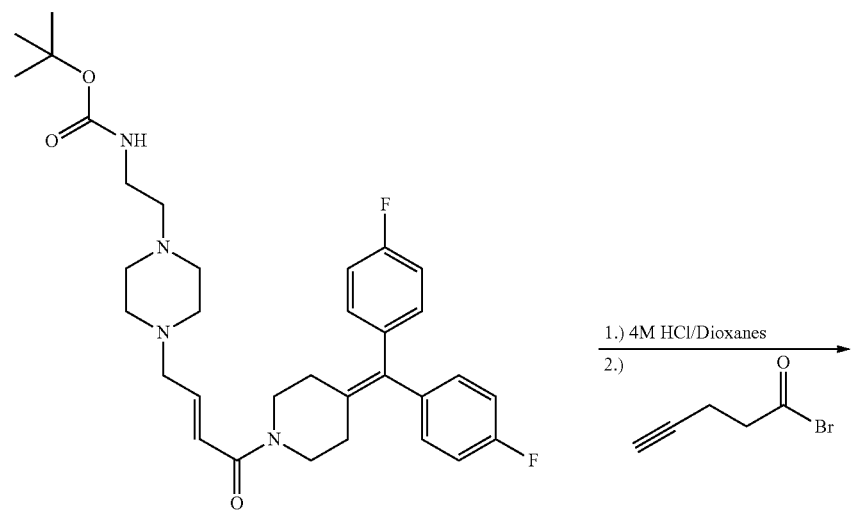

1.) 4M HCl/Dioxanes
2.)

-continued

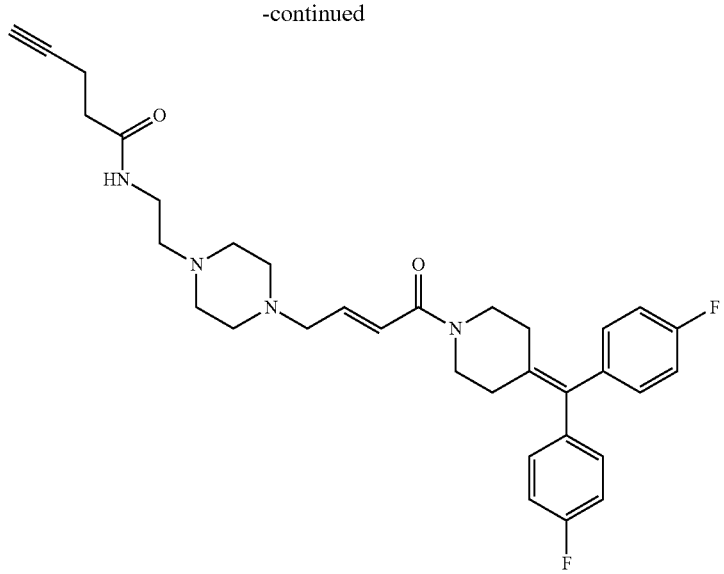

1. Reaction was dissolved in 4M HCl/dioxanes for two hours
2. Reaction was dried on rotary evaporator.
3. pent-4-ynoyl bromide (1.5 eq) was dissolved into THF with DIEA (3 eq)
4. Reaction was allowed to stir overnight
5. Reaction was washed quenched with sodium bicarbonate
   a. Extracted into ethyl acetate
   b. Washed with brine
6. Sample was dried over magnesium sulfate
7. Concentrated on rotary evaporator
8. Sample was purified via RP-HPLC JWB019
(2E)-4-Bromobut-2-enoic Acid Chloride

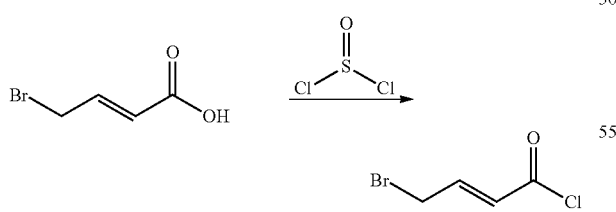

1. (2E)-4-Bromobut-2-enoic Acid (1 eq) was dissolved in anhydrous THF
2. Thionyl chloride (1.5 eq) was added dropwise to the reaction flask a. Catalytic drop of DMF was added to the reaction flask
3. Reaction stirred for 3 hour at RT
4. Concentration on rotary evaporation
5. Carry to next step without further purification

JWB018

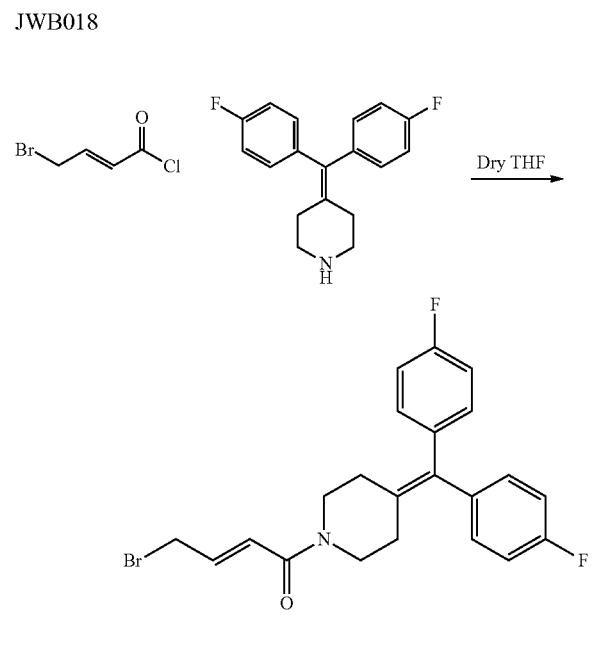

1. RF001 (1 eq) was dissolved in anhydrous THF
   a. Triethyl amine (3 eq) was added to flask
   b. Sample was cooled to −20 degree
2. (2E)-4-Bromobut-2-enoic Acid Chloride (1.3 eq) was dissolved in anhydrous THF:
   a. Add dropwise over 15 minutes
   b. Allowed to stir at −20 degree for 30 minutes 3. Reaction was quenched with sodium bicarbonate:
   a. Extracted in ethyl acetate ;
   b. Washed with brine
   c. Dried with magnesium sulfate
4. Concentrate on rotary evaporator
5. Purified via column chromatography (1:3 ethyl acetate: hexanes)

JWB019

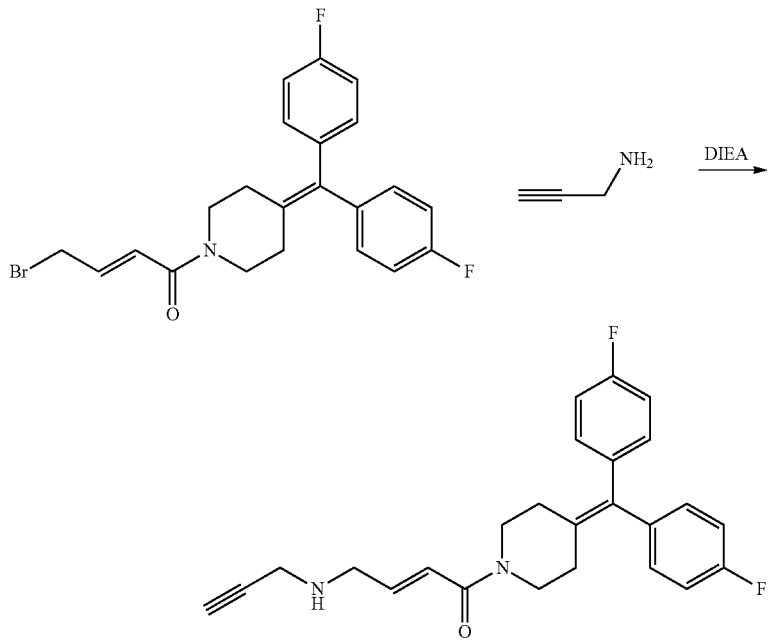

1. JWB018 (1 eq) was dissolved in THF
   a. Cooled on ice
2. Propargyl amine (1.5 eq) was dissolved In THF with DIEA (3 eq) and added to the reaction flask slowly.
3. Reaction was allowed to warm to room temperature and stirred overnight
4. Reaction was quenched with sodium bicarbonate
   a. Extracted in ethyl acetate
   b. Washed with brine
5. Concentrated on rotary evaporator
6. Purified via column chromatography (2% methanol in DCM)

PROBE UTILITY: For example, JWB003 is a cysteine reactive covalent probe that broadly targets C1-domain containing proteins and may be used to study the lipid response and activity of protein and lipid kinases. As another example, JWB017, a rhodamine analog of JWB003, can be used to discover new inhibitors of C1 domain proteins through fluorescent polarization high throughput screening (HTS) assays.

JWB003 covalently labels hDGKα in situ. Time dependent labeling of HEK293T cells transiently transfected with recombinant hDGKα shows time dependent labeling with JWB003 at 25 μM with prominent labeling in the membrane fraction of cell proteome. Probe labeling appears to saturate at 60 minutes.

Competition experiments to support JWB003 labeling of C1 domain cysteines of hDGKα in vitro. Probe labeling is inhibited by C1 domain inhibitors such as ritanserin and phorbol esters (PMA), but not catalytic domain inhibitors such as adenosine triphosphate (ATP). JWB003 labeling is inhibited by the general cysteine inhibitor iodoacetamide, giving evidence that the probe covalently modifies cysteine. The sensitivity to PMA and unique ability to label at the C1 domain of kinases allows JWB003 to probe lipid activation of lipid kinases including DGKs.

JWB003 labels all ten isoforms of recombinant DGKs in situ. HEK293T cells were transiently transfected to express distinct recombinant DGK isoforms (total of 10). JWB003 treatment shows effective labeling of all ten proteins in live cells. The ability to label all DGK isoforms expands the utility of the probe to study lipid recognition of all ten DGK isoforms.

JWB003 labels protein kinases that contain C1 domains. HEK293T cells were transiently transfected to express human PKCa (hPKCa). JWB003 treatment showed labeling of hPKCa in the membrane but not soluble fraction of the cell proteome. The significance of this finding is hPKCa is membrane localized after activation by lipid signals in cell signaling. Data shows that PMA (mimics DAG lipid secondary messengers) activation of hPKCa-HEK293T cells results in prominent hPKCa expression in the membrane, which can be detected by JWB003.

Gel-based activity based protein profiling analysis shows time dependent labeling of purified rat DGKα (rDGKα) using JWB017, a rhodamine analog of JWB003. Gel-based experiments were used to optimize JWB017 labeling conditions of purified rDGKα for fluorescence polarization assay. Data show that ~50% labeling of protein was achieved at 60 min.

JWB017 can be used to discover new inhibitors of C1 domain proteins through fluorescent polarization high throughput screening (HTS) assays. Fluorescent polarization assay (FluoPol Assay) showing time dependent labeling of pure rat DGKα (rDGKα). When excited with plane-polarized light, fluorophore emit light parallel to the plane of excitation unless it rotates in the excited-state. The speed of molecular rotation results in depolarization. When free in solution, the fluorophore emits depolarized light, but when bound by a protein, the fluorophore rotates much more slowly and emits highly polarized light. Using the parameters optimized in the in-gel assay above, pure rat DGKα was treated to determine if the probe could meet the necessary conditions for a fluorescence polarization assay: (1) probe labeling in the 50-100 nM range, (2) efficient labeling in a reasonable amount of time (0.5-2.0 hours) and (3) labeling of the protein at room temperature. It was determined that enzyme alone does not give appreciable background signals (JWB017 vs DMSO). The fluorescence polarization (FP) signal is observed to be 2-4× higher in JWB017+rDGKα samples when compared to JWB017 probe alone. Protein labeling was effectively seen with 100 nM of JWB017, optimal labeling is observed at the 60-minute time point, and FP signal is enzyme dependent. In a HTS assay, pretreatment with inhibitor libraries will identify compounds that bind at rDGKα C1 domain because they will outcompete JWB017 labeling, which results in lower FP signals.

BIBLIOGRAPHY

Agarwal A, et al. (2005) The AKT/I kappa B kinase pathway promotes angiogenic/metastatic gene expression in colorectal cancer by activating nuclear factor-kappa B and beta-catenin. Oncogene 24 (6): 1021-1031.

Barone J A, et al. (1986) Safety evaluation of ritanserin-- an investigational serotonin antagonist. Drug Intell Clin Pharm 20 (10): 770-775.

Bartling B, et al. (2004) RasGTPase-activating protein is a target of caspases in spontaneous apoptosis of lung carcinoma cells and in response to etoposide. Carcinogenesis 25 (6): 909-921.

Blackford AN and Jackson SP (2017) ATM, ATR, and DNA-PK: The Trinity at the Heart of the DNA Damage Response. Mol Cell 66 (6): 801-817.

Boroda S, et al. (2017) Dual activities of ritanserin and R59022 as DGKalpha inhibitors and serotonin receptor antagonists. Biochem Pharmacol 123:29-39.

Castellano et al. (2013) Requirement for interaction of PI3-kinase p 110alpha with RAS in lung tumor maintenance. Cancer cell 24 (5): 617-630.

Chang J W, et al. (2015) Selective inhibitor of platelet-activating factor acetylhydrolases 1b2 and 1b3 that impairs cancer cell survival. ACS Chem Biol 10 (4): 925-932.

Cheng et al. (2016) eEF-2 kinase is a critical regulator of Warburg effect through controlling PP2A-A synthesis. Oncogene 35 (49): 6293-6308.

Dominguez C L, et al. (2013) Diacylglycerol kinase alpha is a critical signaling node and novel therapeutic target in glioblastoma and other cancers. Cancer Discov 3 (7): 782-797.

Edgar RC(2004) MUSCLE: a multiple sequence alignment method with reduced time and space complexity. BMC bioinformatics 5:113.

Franks C E, et al. (2017) The Ligand Binding Landscape of Diacylglycerol Kinases. Cell Chem Biol 24 (7): 870-880 e875.

Graziano S L, et al. (1991) Involvement of the RAF1 locus, at band 3p 25, in the 3p deletion of small-cell lung cancer. Genes Chromosomes Cancer 3 (4): 283-293.

Greer P (2002) Closing in on the biological functions of Fps/Fes and Fer. Nat Rev Mol Cell Biol 3 (4): 278-289.

Hsu K L, et al. (2013) Development and optimization of piperidyl-1,2,3-triazole ureas as selective chemical probes of endocannabinoid biosynthesis. J Med Chem 56 (21): 8257-8269.

Kepp O, et al. (2011) Cell death assays for drug discovery. Nat Rev Drug Discov 10 (3): 221-237.

Kim J A, et al. (2016) Amplification of TLK2 Induces Genomic Instability via Impairing the G2-M Checkpoint. Mol Cancer Res 14 (10): 920-927.

Knight Z A, et al. (2010) Targeting the cancer kinome through polypharmacology. Nat Rev Cancer 10 (2): 130-137.

McCloud R L, et al. (2018) Deconstructing Lipid Kinase Inhibitors by Chemical Proteomics. Biochemistry 57 (2): 231-236.

Morrow A A, et al. (2014) The lipid kinase PI4KIIIbeta is highly expressed in breast tumors and activates Akt in cooperation with Rablla. Mol Cancer Res 12 (10): 1492-1508.

Nagano J M, et al. (2013) Selective inhibitors and tailored activity probes for lipoprotein-associated phospholipase A (2). Bioorg Med Chem Lett 23 (3): 839-843.

Olmez I, et al. (2017) Targeting the mesenchymal subtype in glioblastoma and other cancers via inhibition of diacylglycerol kinase alpha. Neuro Oncol.

Patricelli Matthew P, et al. (2011) In Situ Kinase Profiling Reveals Functionally Relevant Properties of Native Kinases. Chemistry & Biology 18 (6): 699-710.

Patricelli M P, et al. (2007) Functional interrogation of the kinome using nucleotide acyl phosphates. Biochemistry 46 (2): 350-358.

Peng Y, et al. (2018) 5-HT2C Receptor Structures Reveal the Structural Basis of GPCR Polypharmacology. Cell 172 (4): 719-730 e714.

Purow B (2015) Molecular Pathways: Targeting Diacylglycerol Kinase Alpha in Cancer. Clinical Cancer Research 21 (22): 5008-5012.

Rice P, et al. (2000) EMBOSS: the European Molecular Biology Open Software Suite. Trends Genet 16 (6): 276-277.

Sakane F, et al. (2007) Diacylglycerol kinases: why so many of them? Biochim Biophys Acta 1771 (7): 793-806.

Sanclemente M, et al. (2018) c-RAF Ablation Induces Regression of Advanced Kras/Trp53 Mutant Lung Adenocarcinomas by a Mechanism Independent of MAPK Signaling. Cancer cell 33 (2): 217-228 e214.

Shin M, et al. (2018) Isoform-selective activity-based profiling of ERK signaling. Chemical Science 9 (9): 2419-2431.

Sonino N, et al. (2000) Effect of the serotonin antagonists ritanserin and ketanserin in Cushing's disease. Pituitary 3 (2): 55-59.

Wang Y, et al. (2009) Effect of staurosporine on the mobility and invasiveness of lung adenocarcinoma A549 cells: an in vitro study. BMC cancer 9:174.

Ye J, et al. (2010) The GCN2-ATF4 pathway is critical for tumour cell survival and proliferation in response to nutrient deprivation. EMBO J 29 (12): 2082-2096.

Example 4

The compounds of the various embodiments can be synthesized as described in the following examples.

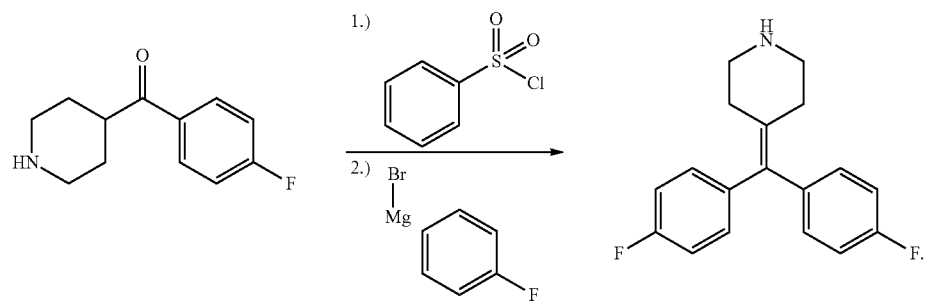
RF001
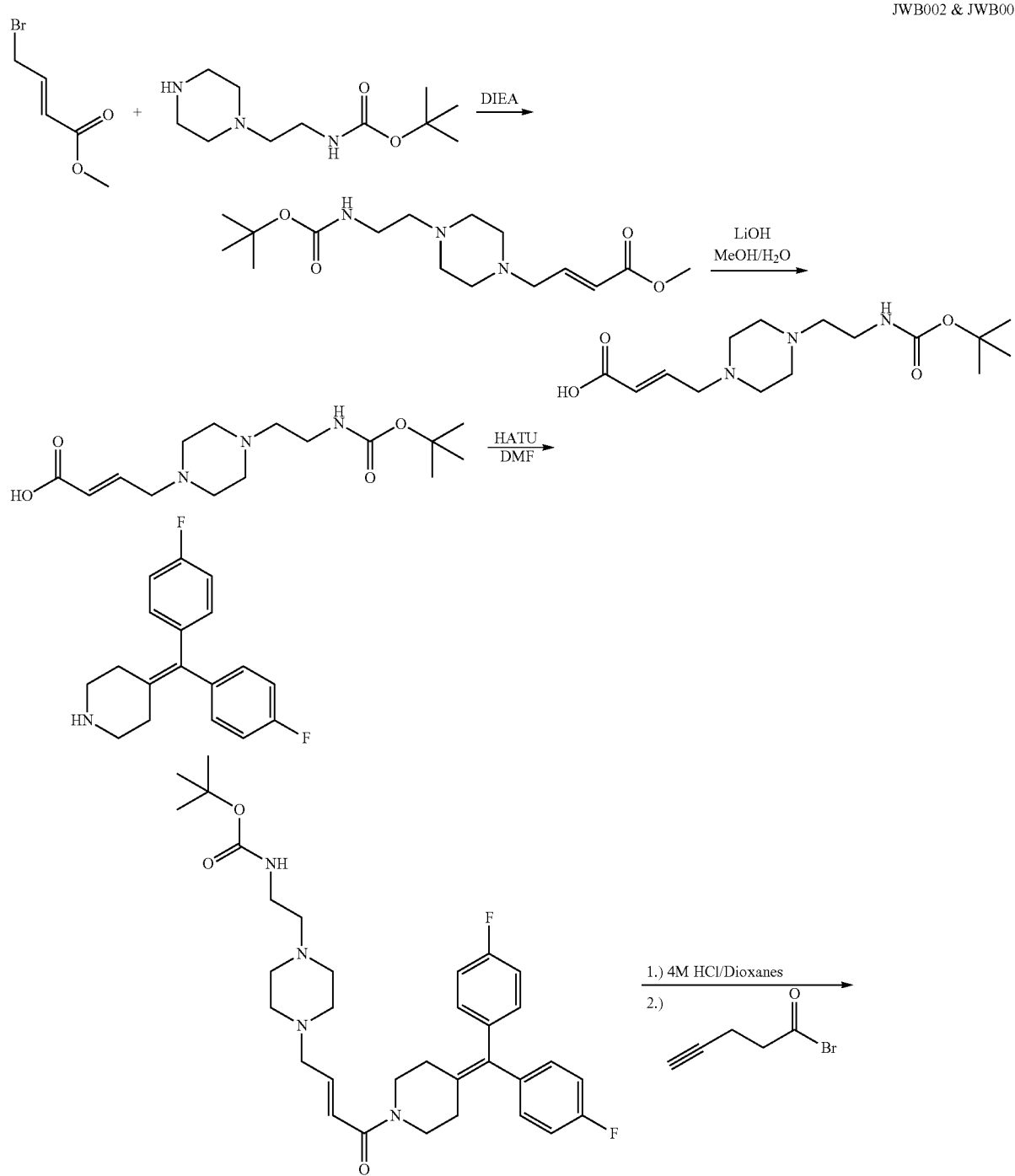
JWB002 & JWB003

-continued
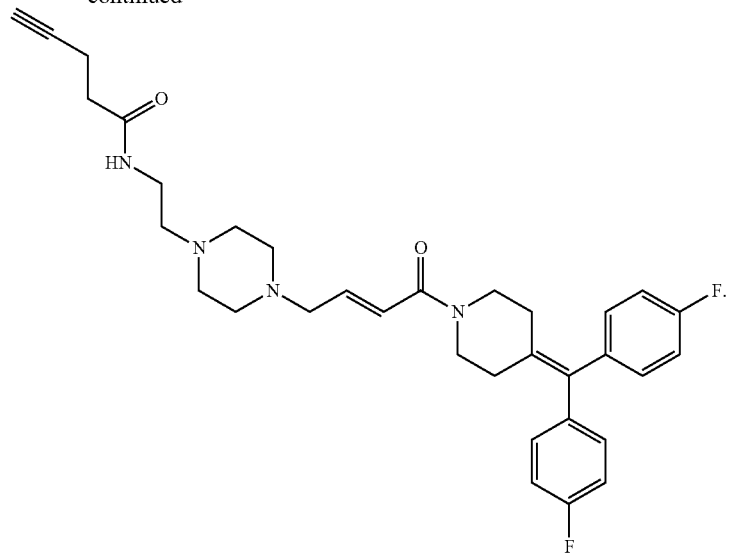
JWB006
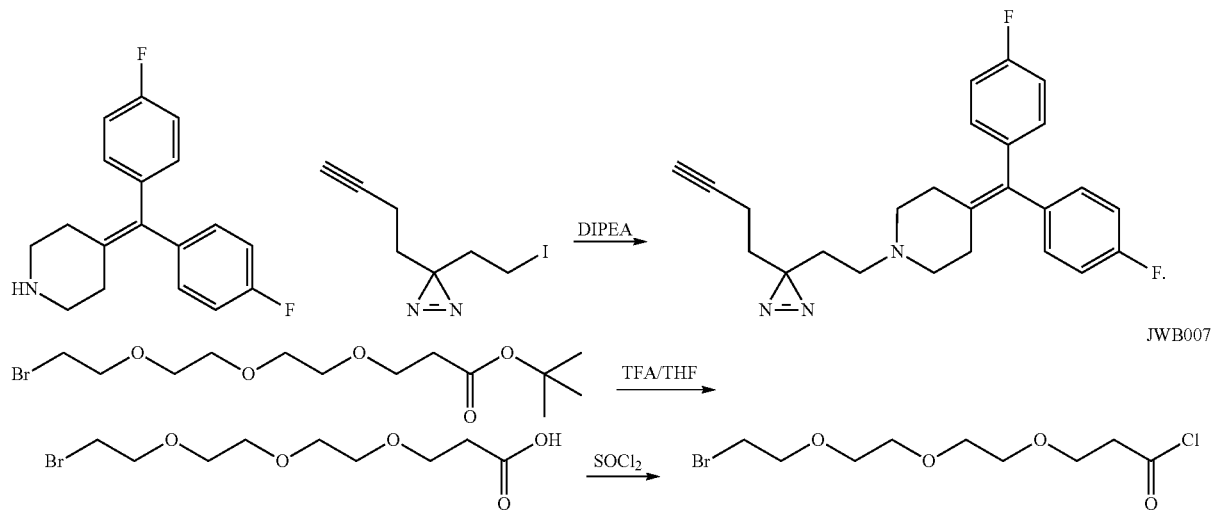
JWB007
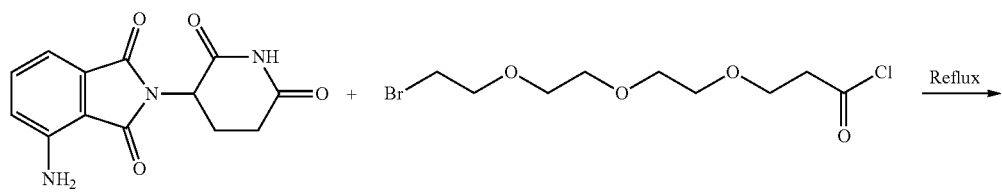
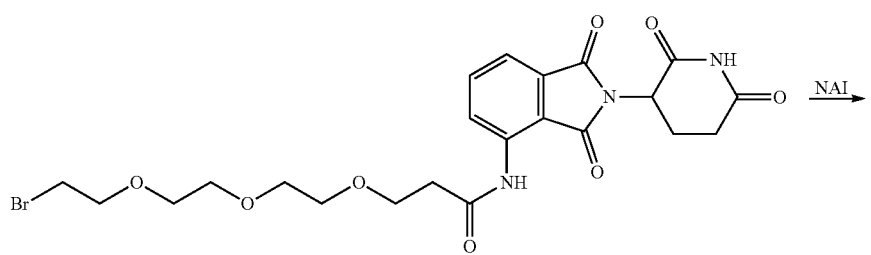

121 122
-continued
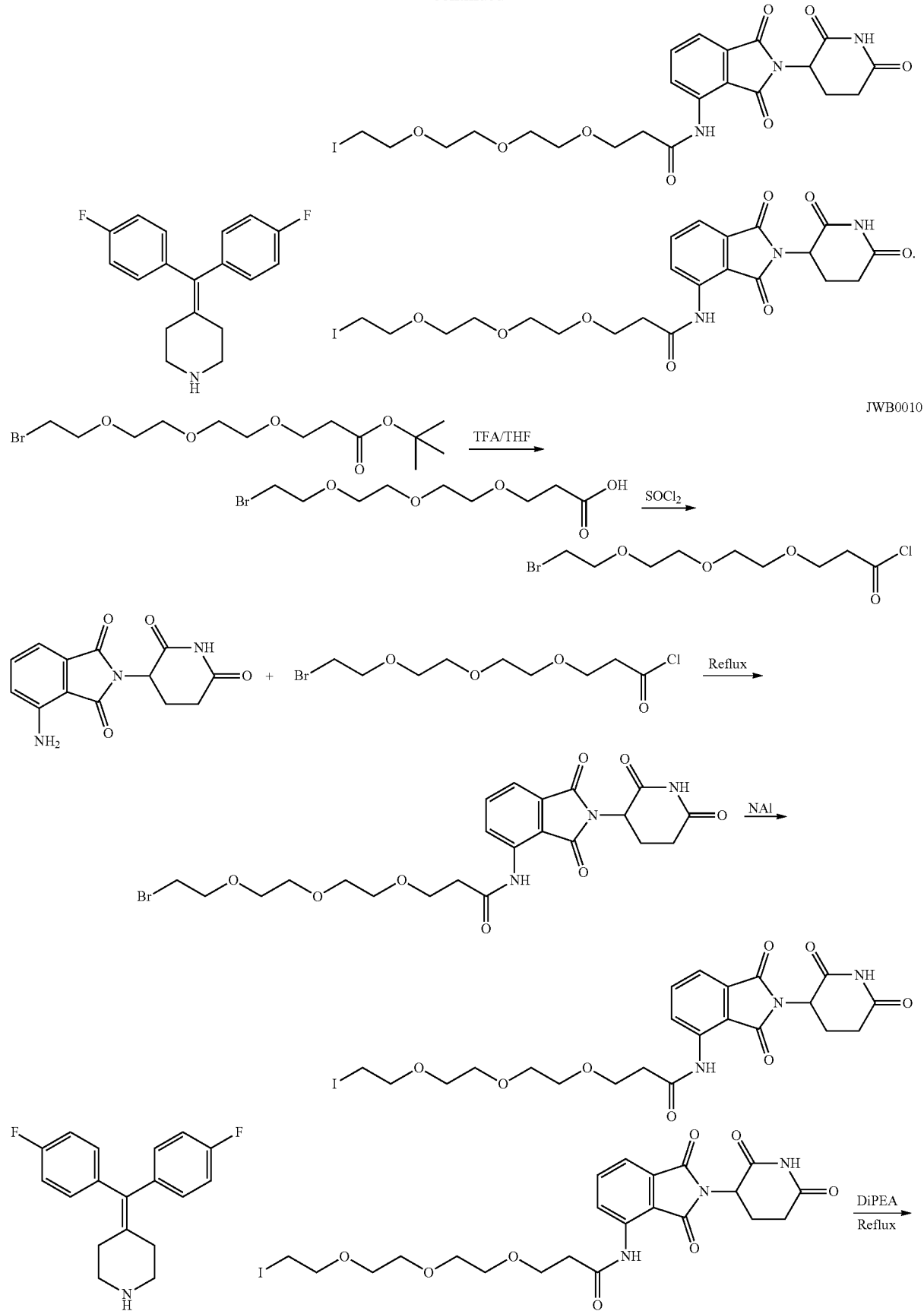
JWB0010

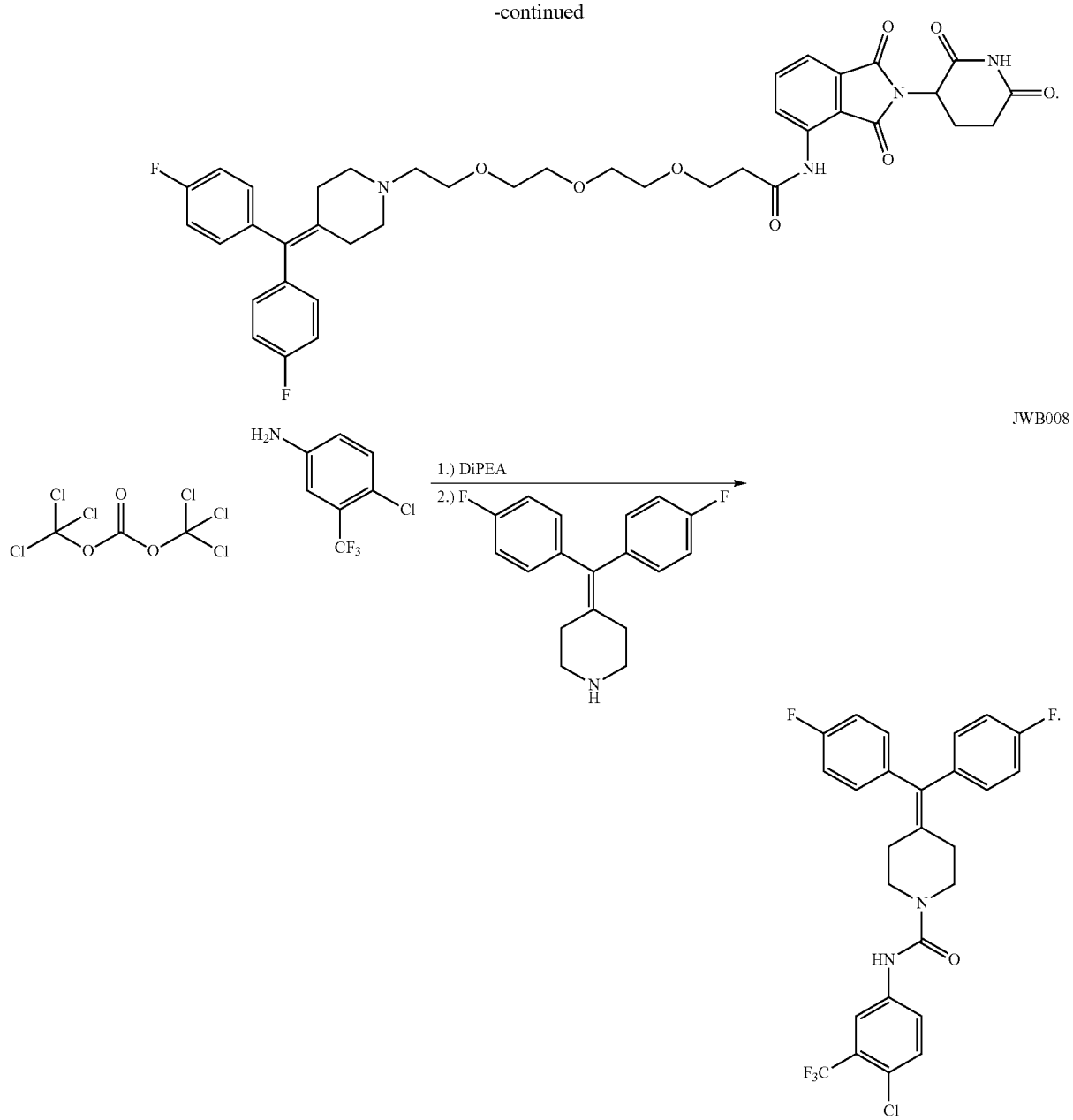

Figure 20:
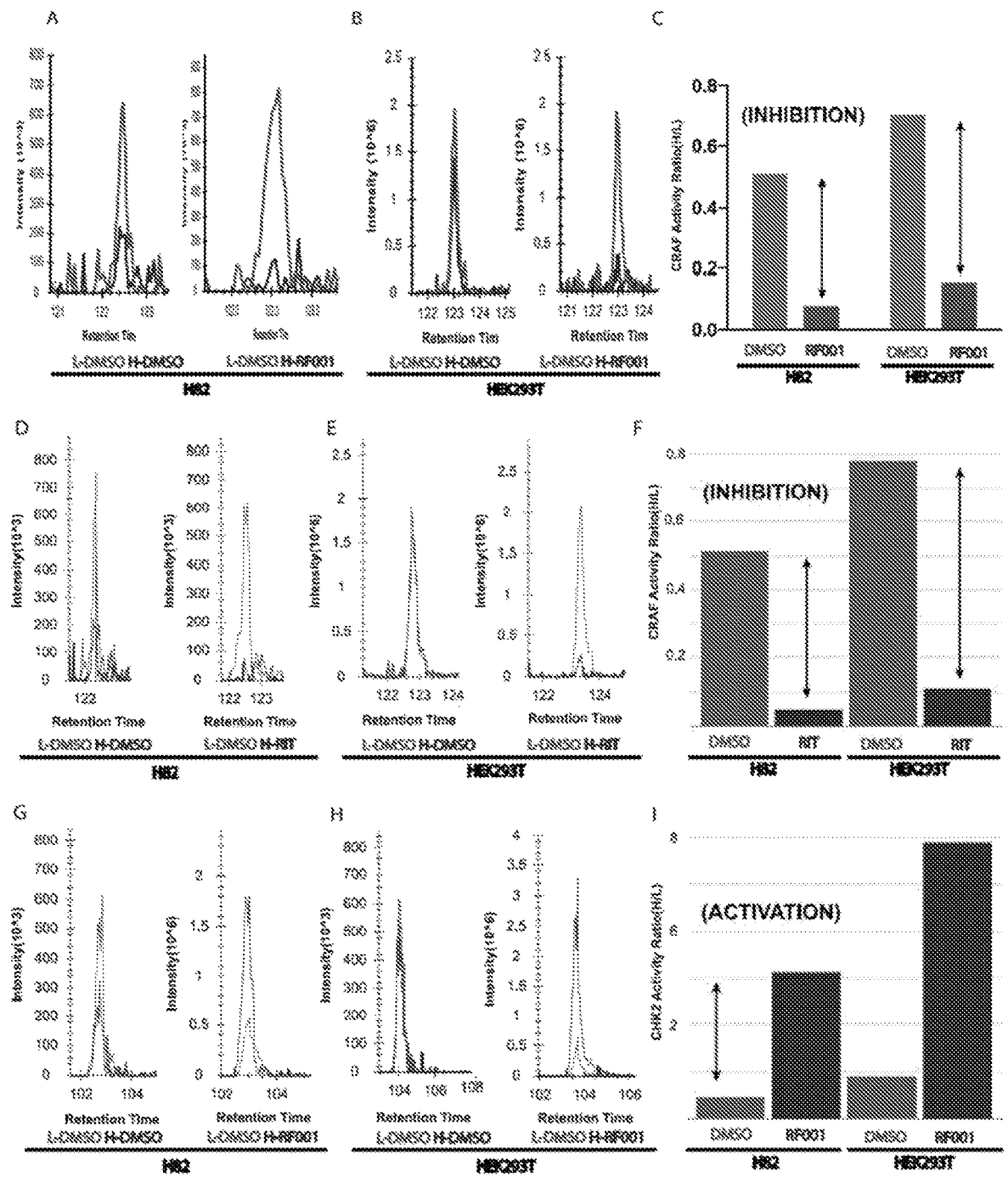

The disclosure provides for the following additional embodiments and clauses, the numbering of which is not to be construed as designating levels of importance:

Embodiment 1: A bifunctional inhibitor that incorporates RF001 into its structure to mediate selective blockade of target kinases that contain both a regulatory domain (e.g. C1) and kinase domain in the same protein:

- ritanserin inactivates DGKA through binding of C1 and DAGKc site of kinase domain (Franks et al. Cell Chemical Biology 2017)
- ritanserin inactivates FER through binding of kinase domain and a potential additional domain (Franks et al. Cell Chemical Biology 2017)
- ritanserin inactivates CRAF, which contains a C1 and kinase domain (FIG. 20)
- RF001 inactivates DGKA through binding of C1 and DAGKc site of kinase domain (Franks et al. Cell Chemical Biology 2017)
- RF001 inactivates CRAF, which contains a C1 and kinase domain (FIG. 20).

Embodiment 2: RF001 serves as an activator of CHK2 through binding of a protein domain.

Embodiment 3: Ritanserin, RF001, and RF001 analogs are novel anticancer agents for treatment of small cell and non-small cell lung cancer cells.

Embodiment 4: RF001 is a CRAF (Uniprot P04049) inhibitor through proposed bifunctional inhibitor mechanism.

125
CLAUSES

Clause 1. A compound according to formula (I), formula (II), formula (III), formula (IV), or formula (V):

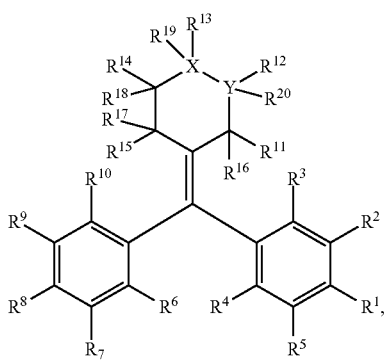
(I)

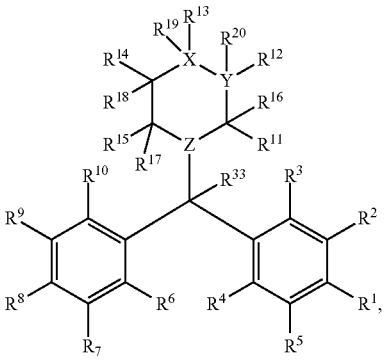
(II)

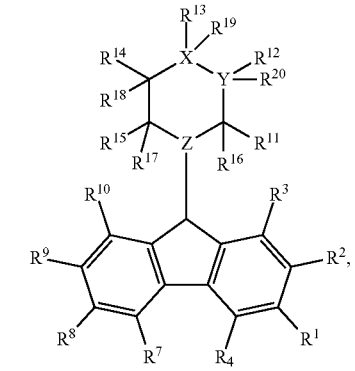
(III)

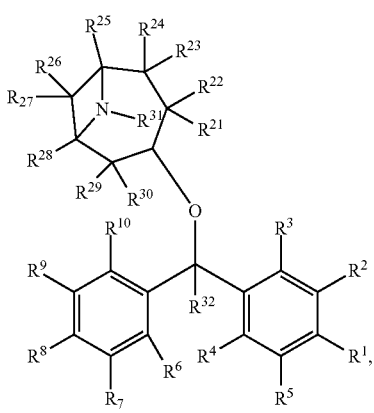
(IV)

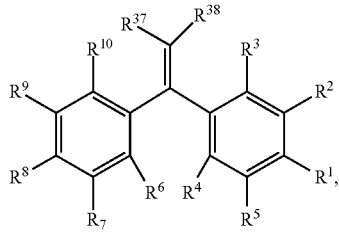
(V)

or a pharmaceutically acceptable salt, polymorph, prodrug, or solvate thereof;

wherein:

X is selected from the group consisting of: —$CR^{19}R^{13}$—, —$NR^{35}$—; Y is selected from the group consisting of: —$CR^{12}R^{20}$—, —$NR^{36}$—;

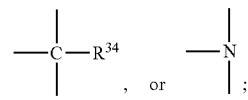

and X is selected from the group consisting of:
$R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{22}$, $R^{23}$, $R^{24}$, $R^{25}$, $R^{26}$, $R^{27}$, $R^{28}$, $R^{29}$, $R^{30}$, $R^{31}$, $R^{32}$, $R^{33}$, $R^{34}$, $R^{35}$, $R^{36}$, $R^{37}$, and $R^{38}$, independently, are selected from the group consisting of —H, —F, —Cl, —Br and substituted or unsubstituted ($C_1$-$C_{100}$) hydrocarbyl.

Clause 2. The compound of clause 1, wherein $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{22}$, $R^{23}$, $R^{24}$, $R^{25}$, $R^{26}$, $R^{27}$, $R^{28}$, $R^{29}$, $R^{30}$, $R^{31}$, $R^{32}$, $R^{33}$ and $R^{34}$, independently, are selected from the group consisting of: substituted or unsubstituted ($C_1$-$C_{100}$)alkyl, ($C_1$-$C_{100}$)alkenyl, ($C_1$-$C_{100}$)alkynyl, ($C_1$-$C_{10}$)acyl, ($C_1$-$C_{20}$) cycloalkyl, ($C_1$-$C_{20}$)aryl, ($C_1$-$C_{20}$)aralkyl, ($C_1$-$C_{100}$)alkoxy, an amine, or ($C_1$-$C_{100}$)haloalkyl.

Clause 3. The compound of clause 1 or 2, wherein $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{22}$, $R^{23}$, $R^{24}$, $R^{25}$, $R^{26}$, $R^{27}$, $R^{28}$, $R^{29}$, $R^{30}$, $R^{31}$, $R^{32}$, $R^{33}$ and $R^{34}$, independently, are selected from the group consisting of: substituted or unsubstituted ($C_1$-$C_{40}$)alkyl, ($C_1$-$C_{40}$)alkenyl, ($C_1$-$C_{10}$)alkynyl, ($C_1$-$C_{40}$)acyl, ($C_1$-$C_{10}$) cycloalkyl, ($C_1$-$C_{10}$)aryl, ($C_1$-$C_{10}$) aralkly, ($C_1$-$C_{40}$)alkoxy, an amine, or ($C_1$-$C_{40}$)haloalkyl.

Clause 4. The compound of any one of clauses 1-3, wherein $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{22}$, $R^{23}$, $R^{24}$, $R^{25}$, $R^{26}$, $R^{27}$, $R^{28}$, $R^{29}$, $R^{30}$, $R^{31}$, $R^{32}$, $R^{33}$ and $R^{34}$, independently, are selected from the group consisting of: —F, —Cl, —Br, —$CH_3$, —$CF_3$, —$OCF_3$, —$OCH_3$, —$CH_2F$, —$NH_2$, —$NHSO_2CH_2CH_2CH_3$, —$CONHCH_3$, —$C(CH_3)_3$, —$NHCH(CH_3)_2$, —$CH_2OH$, —$COC_5H_{11}N$, —COOH, —OH, 127
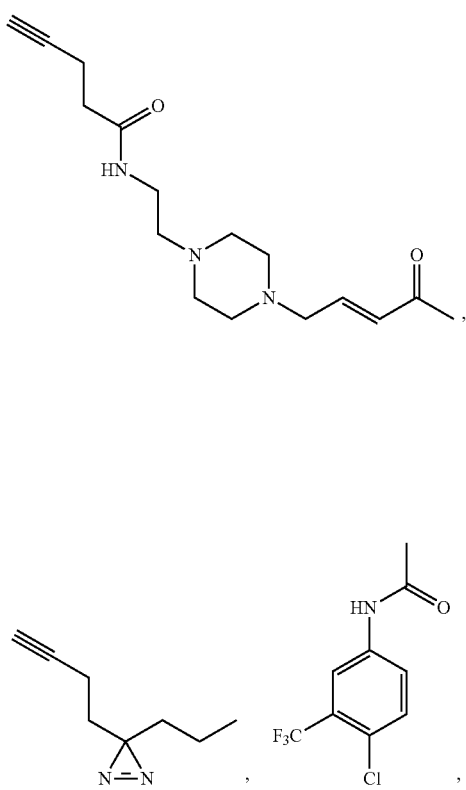
128
-continued
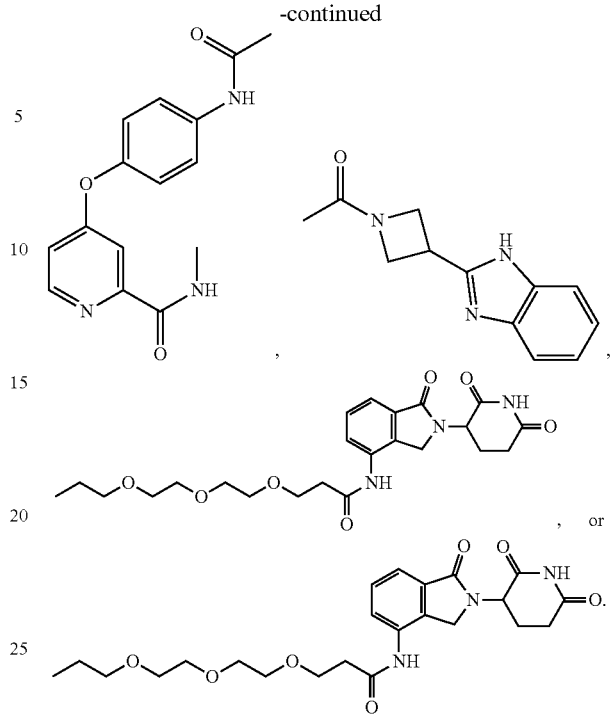
Clause 5. The compound of any one of clauses 1-4, wherein the structure according to formula (I) is selected from the group consisting of:
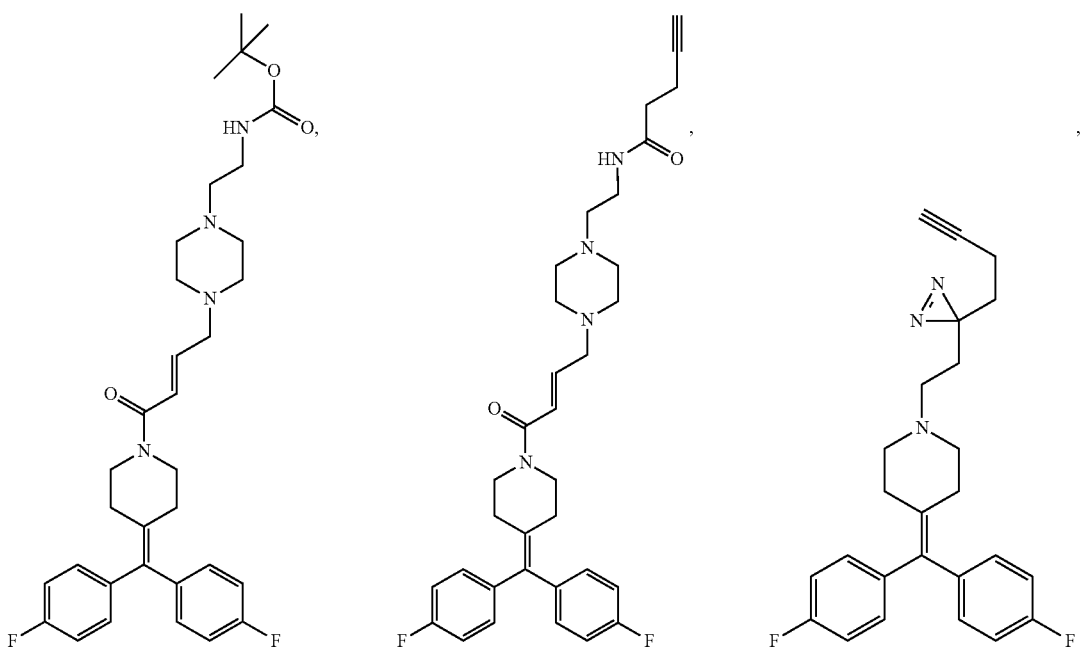

-continued
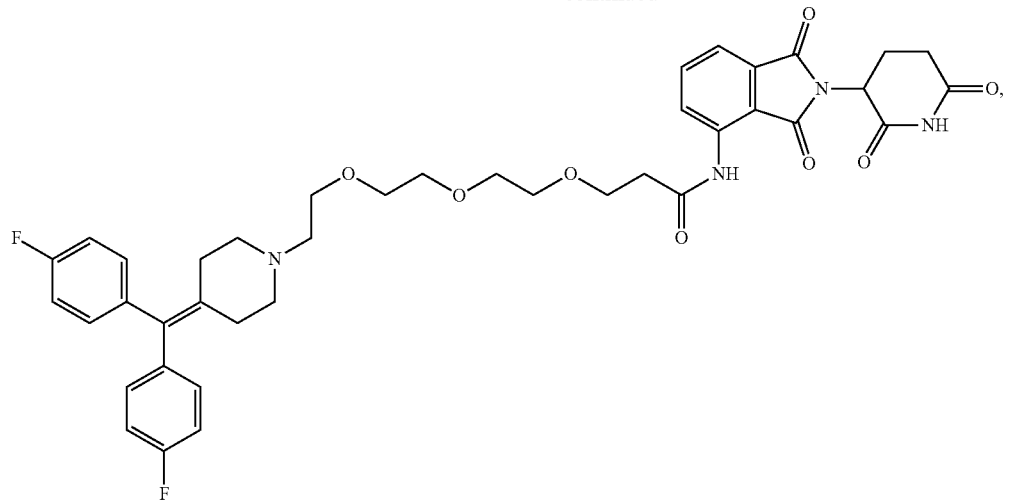
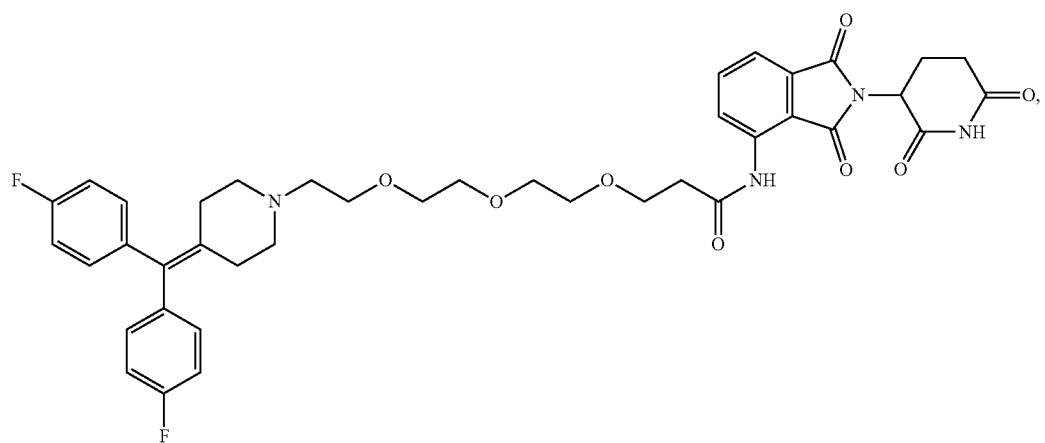
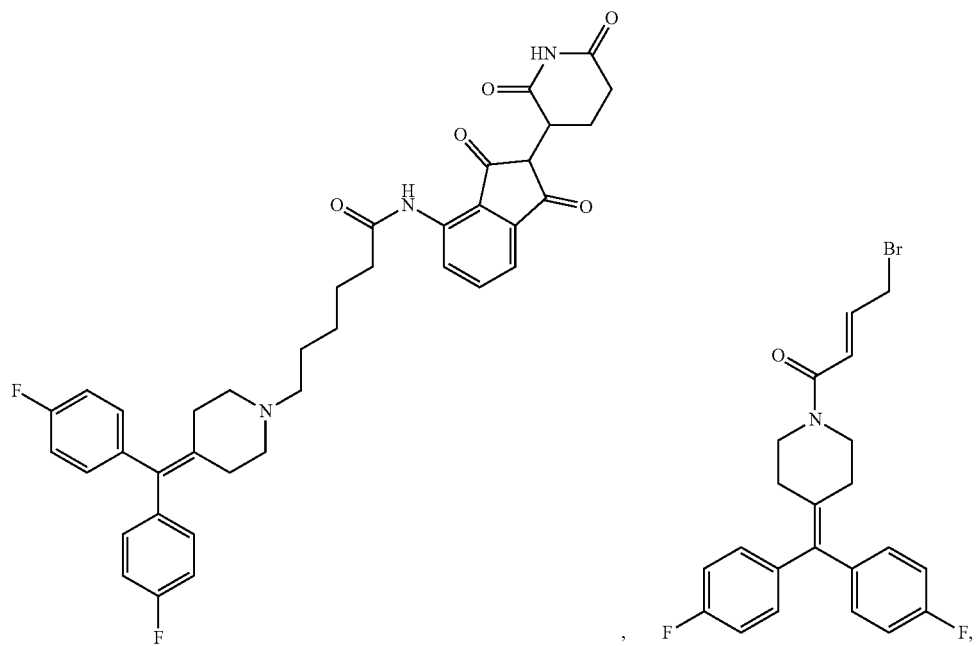

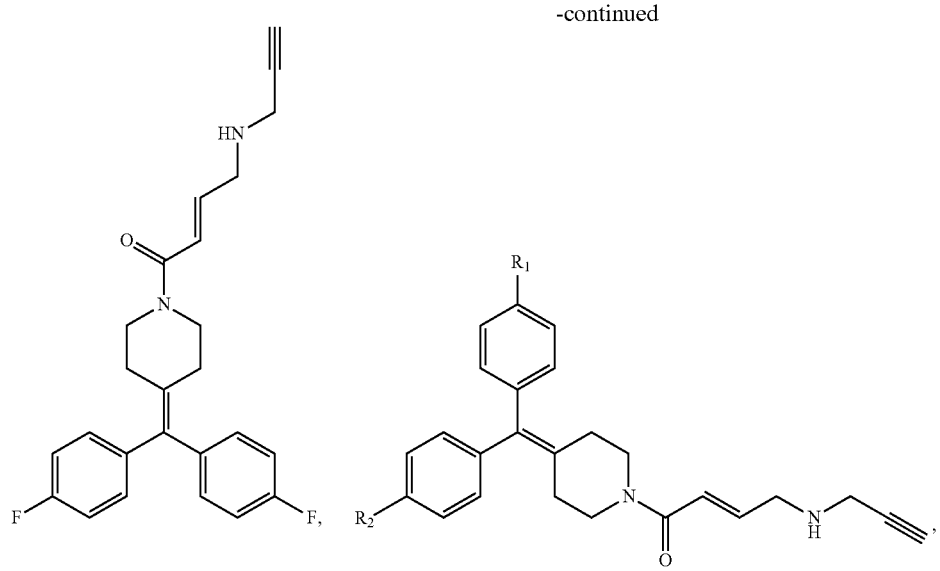
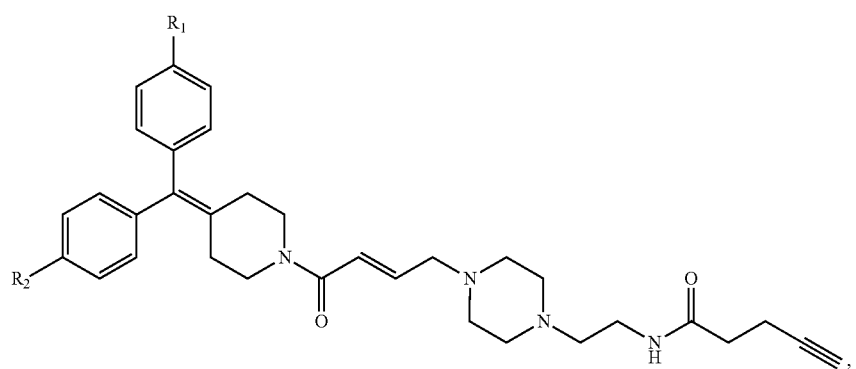
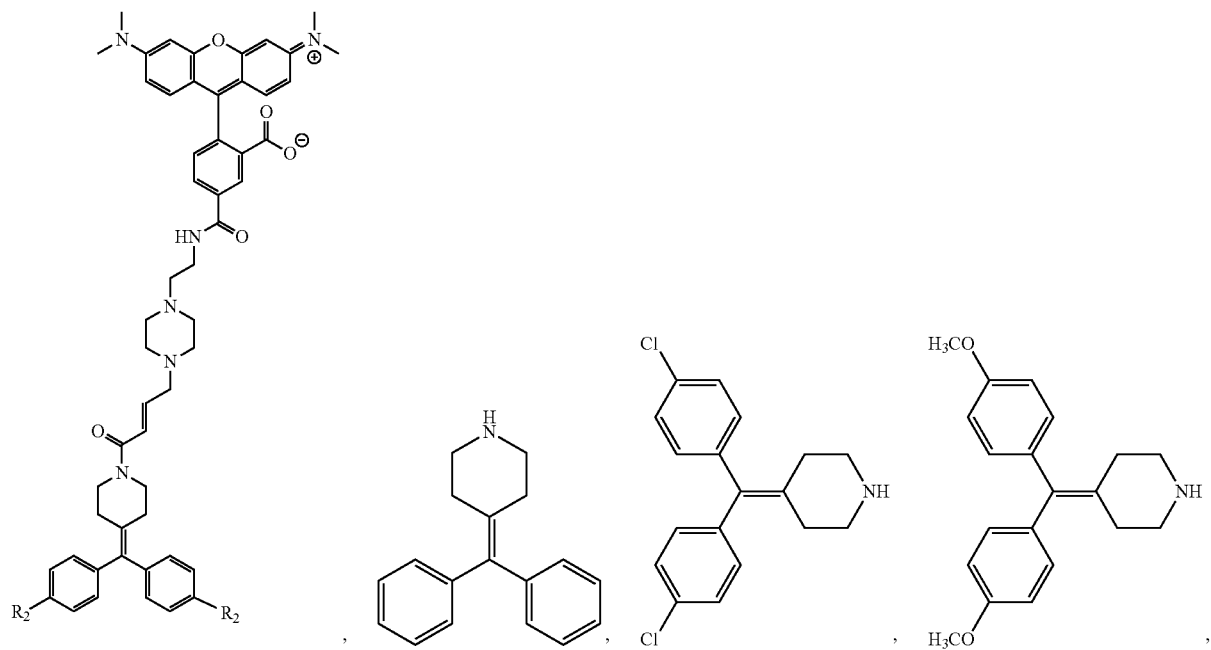

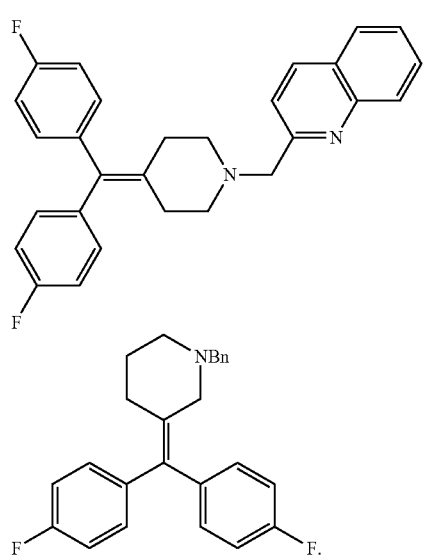 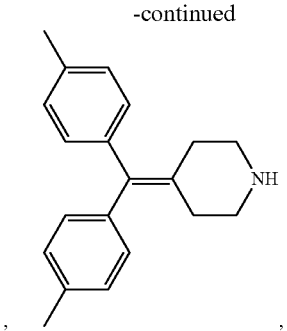 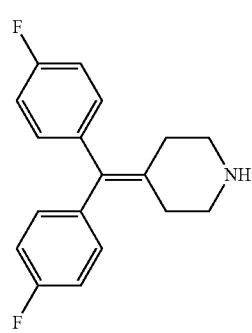
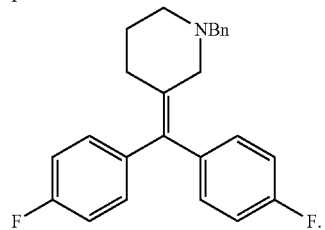
Clause 6. The compound of any one of clauses 1-5, wherein the structure according to formula (II) is selected from the group consisting of:
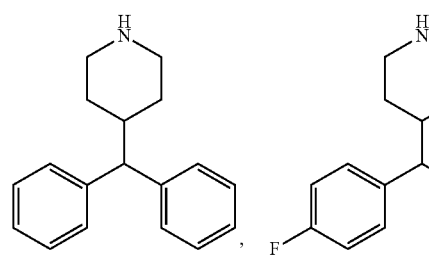
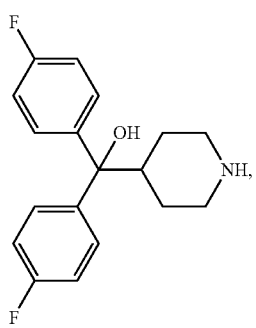
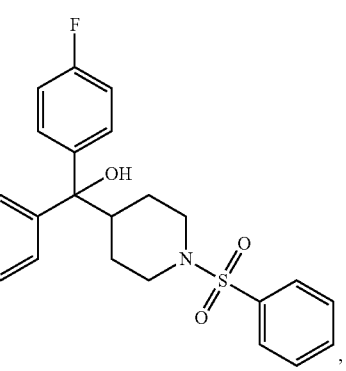
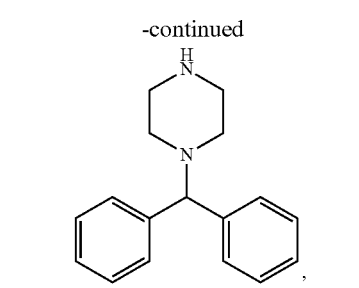
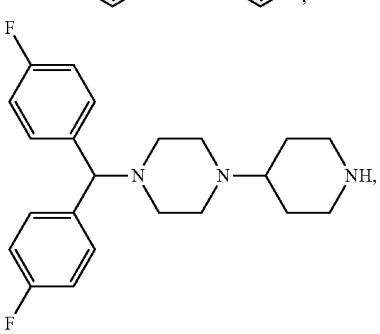
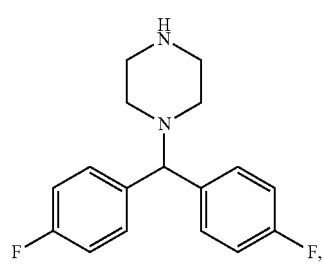
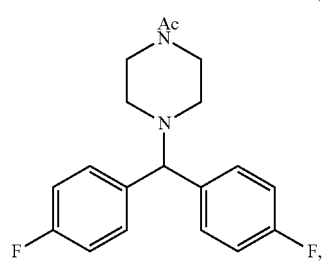

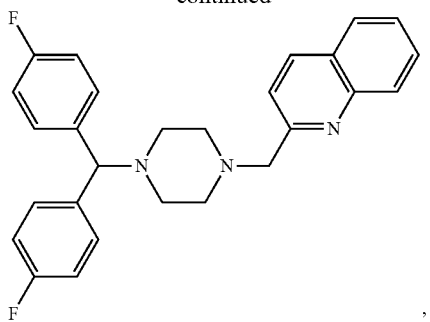
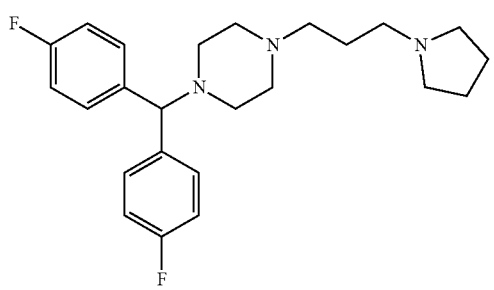
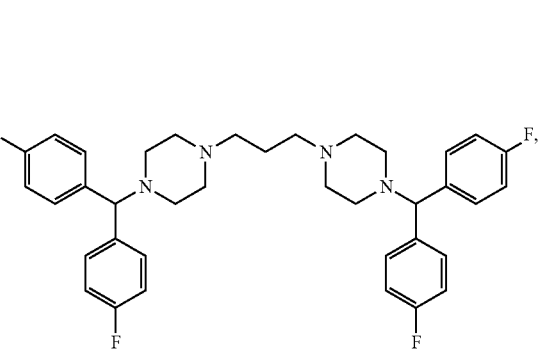
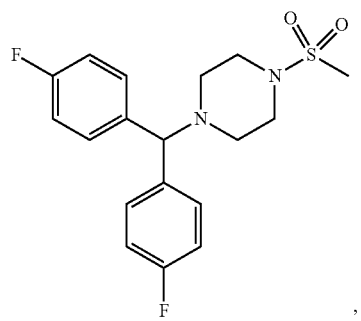
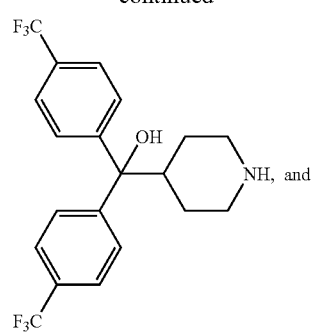
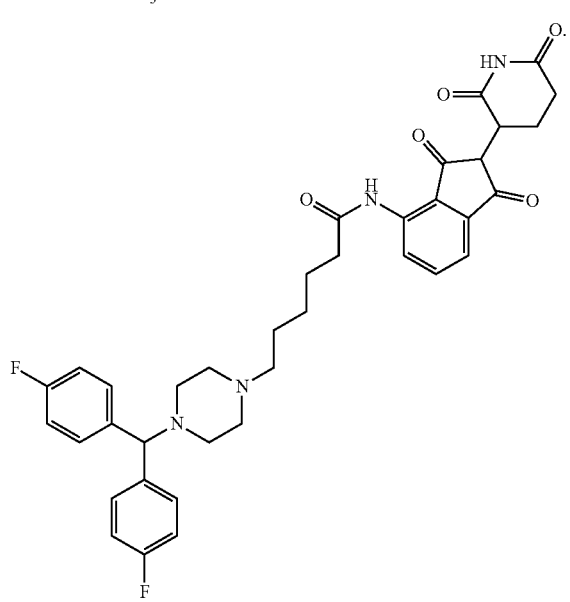
Clause 7. The compound of any one of clauses 1-5, wherein the structure according to formula (III) is
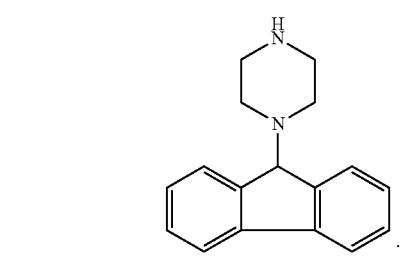 [SMILES: c1ccc2c(c1)-c1ccccc1C2N1CCNCC1]
Clause 8. The compound of any one of clauses 1-5, wherein the structure according to formula (IV) is
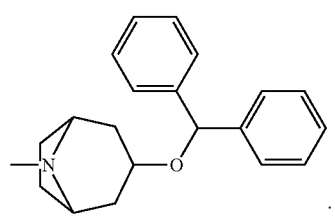 [SMILES: CN1C2CCC1CC(OC(c1ccccc1)c1ccccc1)C2]

Clause 9. The compound of any one of clauses 1-5, wherein the structure according to formula (V) is

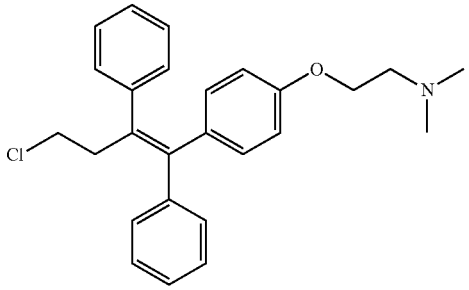

Clause 14. A pharmaceutical composition comprising a compound of any one of clauses 1-9 and a pharmaceutically acceptable excipient.

Clause 15. A method for treating cancer comprising administering an effective amount of at least one compound of formula (I), (II), (III), (IV), or (V) according to any one of clauses 1-13 or the pharmaceutical composition of clause 14 to a subject in need thereof.

Clause 16. The method of clause 15, wherein the cancer is selected from the group consisting of liver cancer, lung cancer, intestinal cancer, kidney cancer, brain cancer, prostate cancer, testes cancer, ovarian cancer, breast cancer, pancreatic cancer, melanoma, lymphoma, leukemia, B-cell cancer or a combination thereof.

Clause 17. The method of clause 16, wherein the lung cancer is small-cell lung or non-small cell lung cancer.

Clause 18. A method for treating a neuropsychiatric disorder comprising administering an effective amount of at least one compound of formula (I), (II), (III), (IV), or (V) according to any one of clauses 1-13 or the pharmaceutical composition of clause 14 to a subject in need thereof.

Clause 19. The method of clause 18, wherein the neuropsychiatric disorder is selected from bipolar disorder, depression, schizophrenia and obsessive-compulsive disorder.

Clause 20. A method to active T-cells comprising contacting an inactive T-cell with an effective amount of at least one compound of formula (I), (II), (III), (IV), or (V) according to any one of clauses 1-13 or the pharmaceutical composition of clause 14.

Clause 21. A method to selectively inhibit a kinase comprising contacting the kinase with an effective amount of at least one compound of formula (I), (II), (III), (IV), or (V) according to any one of clauses 1-13 or the pharmaceutical composition of clause 14.

Clause 22. The method of clause 21, wherein the kinase comprises a regulatory domain and a kinase domain in the same protein.

Clause 23. The method or clause 22, wherein the regulatory domain is a $C_1$ domain. Clause 24. A method to method to screen for inhibitors of kinase activity comprising:
a) contacting a kinase with a putative inhibitor;
b) contacting the kinase and putative inhibitor of a) with at least one fluorescently labeled compound of formula (I), (II), (III), (IV), or (V) according to any of clauses 1-13; and
c) remove any unbound fluorescently labeled compound and then measure fluorescent signals:
wherein a lower fluorescent signal indicates that the putative inhibitor is an inhibitor of kinase activity.

Clause 25. The method of clause 24, wherein the kinase has a $C_1$ domain.

What is claimed is:
1. A compound selected from the group consisting of:
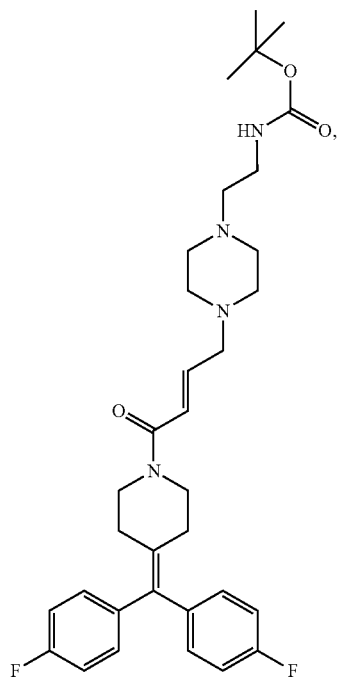
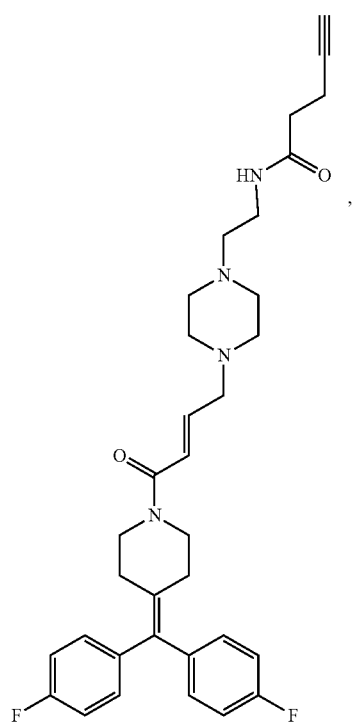
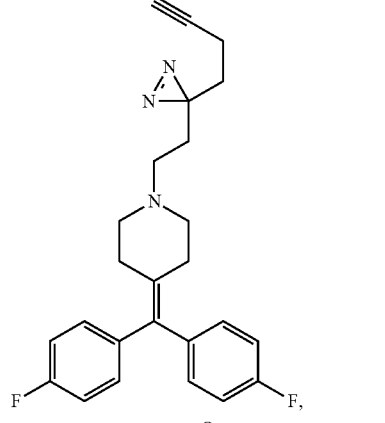
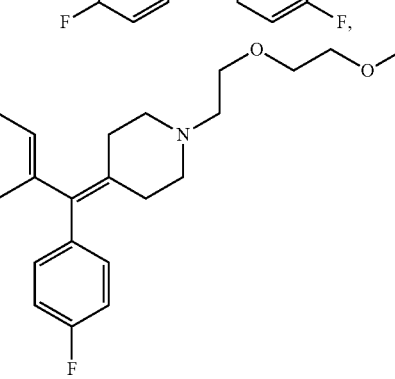
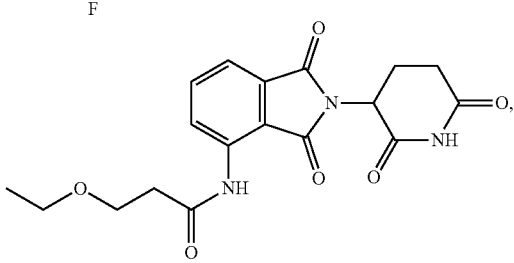
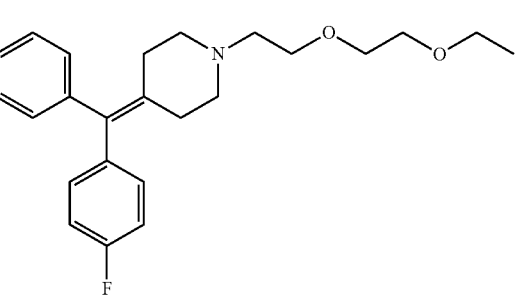
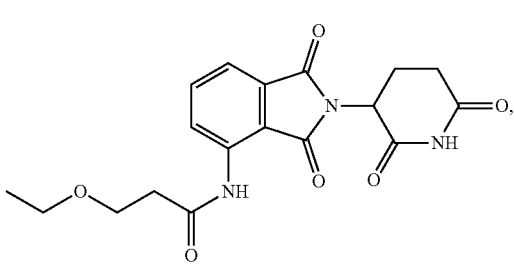

169
-continued
170
-continued
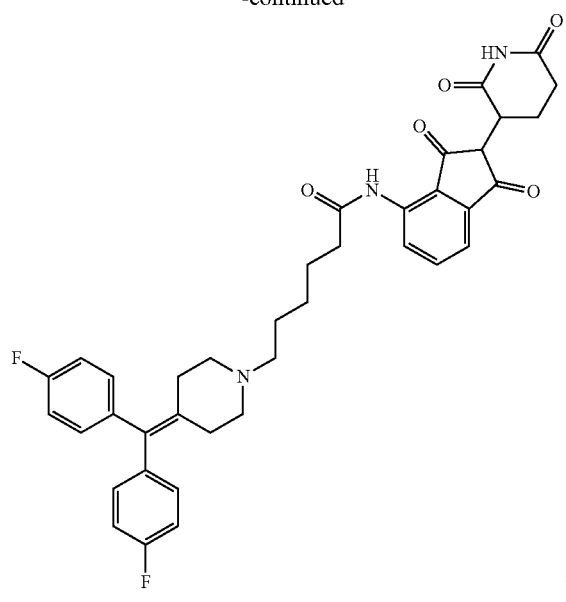
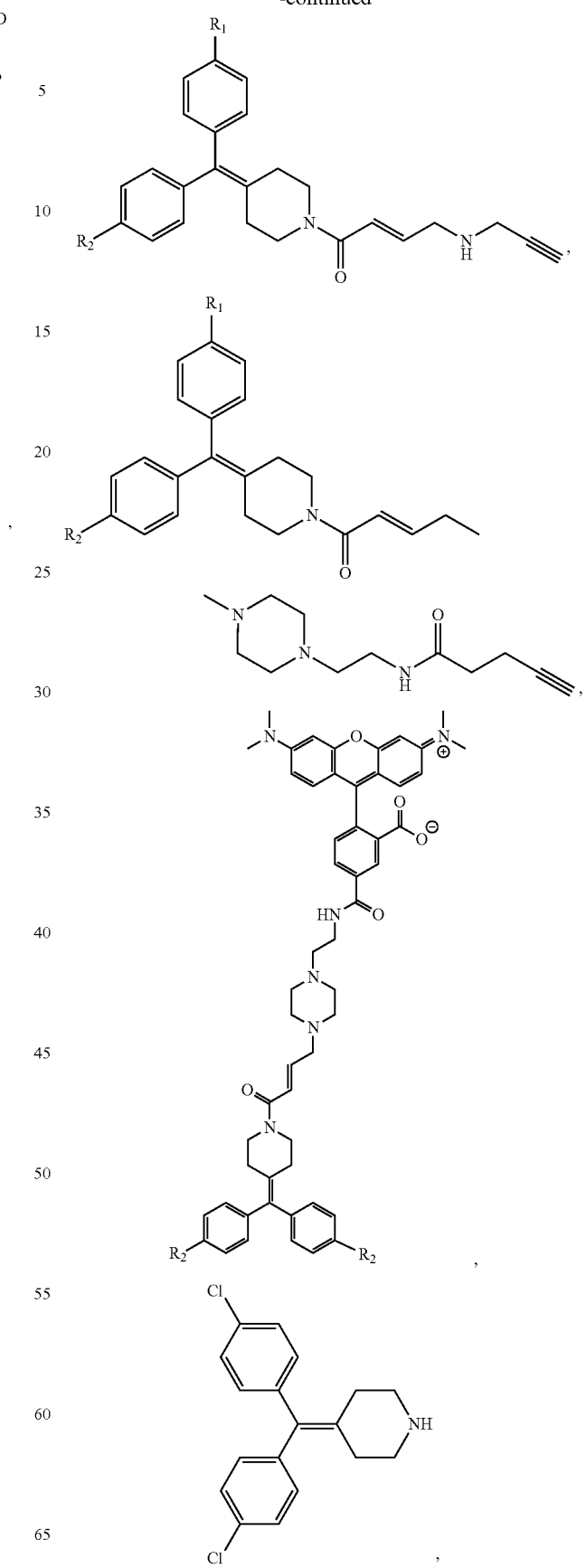

-continued
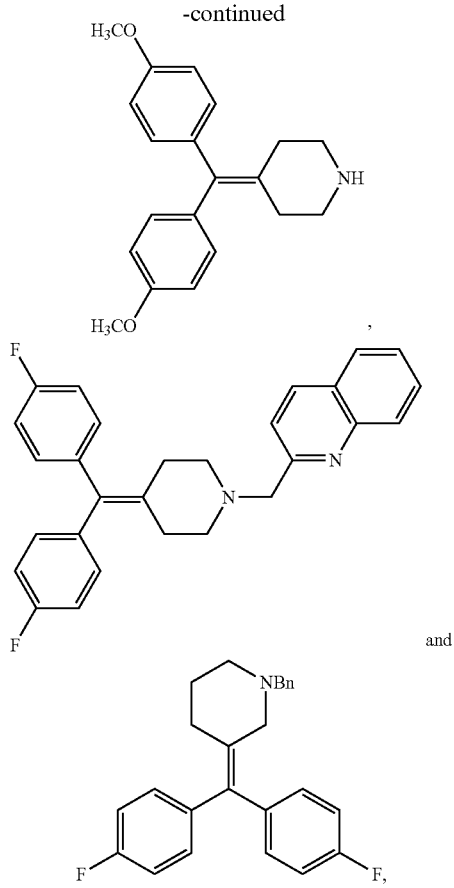
2. A pharmaceutical composition comprising a compound of claim 1 and a pharmaceutically acceptable excipient.
3. The compound of structure
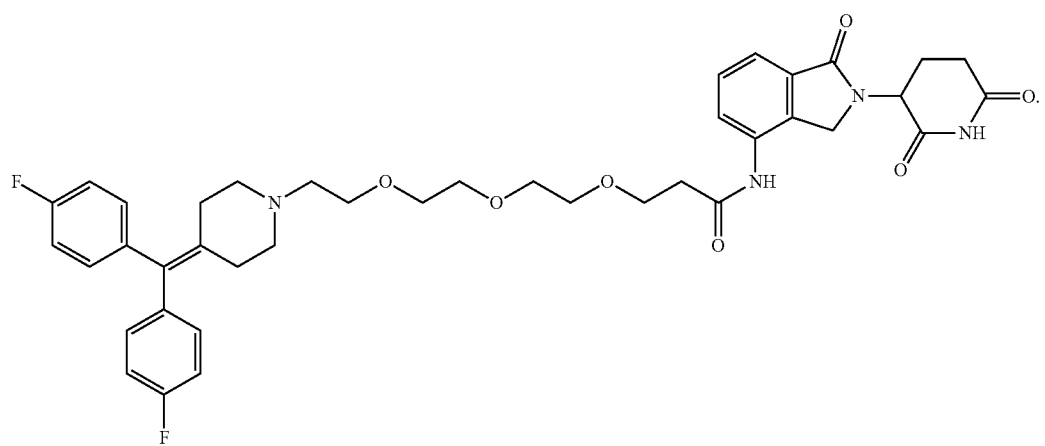 [SMILES: O=C1CCC(N2Cc3c(NC(=O)CCOCCOCCOCCN4CCC(=C(c5ccc(F)cc5)c5ccc(F)cc5)CC4)cccc3C2=O)C(=O)N1]
* * * * *